United States Patent
Cronin et al.

(10) Patent No.: US 11,286,532 B2
(45) Date of Patent: *Mar. 29, 2022

(54) ESTROGEN RECEPTOR MUTATIONS AND USES THEREOF

(71) Applicant: FOUNDATION MEDICINE, INC., Cambridge, MA (US)

(72) Inventors: Maureen T. Cronin, Boston, MA (US); Garrett Michael Frampton, Somerville, MA (US); Doron Lipson, Cambridge, MA (US); Vincent A. Miller, West Orange, NJ (US); Gary Palmer, Waltham, MA (US); Jeffrey S. Ross, Lebanon Springs, NY (US); Philip James Stephens, Lexington, MA (US); Roman Yelensky, Newton, MA (US)

(73) Assignee: FOUNDATION MEDICINE, INC., Cambridge, MA (US)

(*) Notice: Subject to any disclaimer, the term of this patent is extended or adjusted under 35 U.S.C. 154(b) by 35 days.

This patent is subject to a terminal disclaimer.

(21) Appl. No.: 15/877,035

(22) Filed: Jan. 22, 2018

(65) Prior Publication Data

US 2018/0320238 A1    Nov. 8, 2018

Related U.S. Application Data

(63) Continuation of application No. 15/018,640, filed on Feb. 8, 2016, now abandoned, which is a continuation of application No. 14/753,397, filed on Jun. 29, 2015, now Pat. No. 10,093,983, which is a continuation of application No. 14/251,856, filed on Apr. 14, 2014, now abandoned, which is a continuation of application No. PCT/US2012/060133, filed on Oct. 12, 2012.

(60) Provisional application No. 61/615,821, filed on Mar. 26, 2012, provisional application No. 61/547,471, filed on Oct. 14, 2011.

(51) Int. Cl.
| | |
|---|---|
| *C12Q 1/6886* | (2018.01) |
| *A61K 31/565* | (2006.01) |
| *A61K 31/4196* | (2006.01) |
| *A61K 31/675* | (2006.01) |
| *A61K 31/439* | (2006.01) |
| *A61K 31/567* | (2006.01) |
| *A61K 31/416* | (2006.01) |
| *A61K 31/423* | (2006.01) |
| *A61K 31/428* | (2006.01) |
| *A61K 31/437* | (2006.01) |
| *A61K 31/4439* | (2006.01) |
| *A61K 31/472* | (2006.01) |
| *A61K 31/536* | (2006.01) |
| *A61K 31/5415* | (2006.01) |
| *A61K 45/06* | (2006.01) |
| *C07K 14/72* | (2006.01) |
| *C07K 16/28* | (2006.01) |
| *A61K 31/436* | (2006.01) |

(52) U.S. Cl.
CPC .......... *C12Q 1/6886* (2013.01); *A61K 31/416* (2013.01); *A61K 31/4196* (2013.01); *A61K 31/423* (2013.01); *A61K 31/428* (2013.01); *A61K 31/436* (2013.01); *A61K 31/437* (2013.01); *A61K 31/439* (2013.01); *A61K 31/4439* (2013.01); *A61K 31/472* (2013.01); *A61K 31/536* (2013.01); *A61K 31/5415* (2013.01); *A61K 31/565* (2013.01); *A61K 31/567* (2013.01); *A61K 31/675* (2013.01); *A61K 45/06* (2013.01); *C07K 14/72* (2013.01); *C07K 16/2869* (2013.01); *C07K 2317/34* (2013.01); *C12Q 2600/106* (2013.01); *C12Q 2600/118* (2013.01); *C12Q 2600/156* (2013.01)

(58) Field of Classification Search
CPC .................................................. C12Q 1/6886
USPC ........................................................ 514/182
See application file for complete search history.

(56) References Cited

U.S. PATENT DOCUMENTS

| | | | |
|---|---|---|---|
| 2006/0100168 A1 | 5/2006 | Ravid et al. | |
| 2010/0029498 A1 | 2/2010 | Gnirke et al. | |
| 2010/0120039 A1 | 5/2010 | Fuqua | |
| 2012/0007135 A1 | 1/2012 | Yao et al. | |
| 2014/0221329 A1 | 8/2014 | Cronin et al. | |
| 2016/0145691 A1 | 5/2016 | Cronin et al. | |
| 2016/0201135 A1 | 7/2016 | Cronin et al. | |
| 2017/0016073 A1 | 1/2017 | Cronin et al. | |

FOREIGN PATENT DOCUMENTS

| | | |
|---|---|---|
| WO | 2011156518 A2 | 12/2011 |
| WO | 2011159769 A2 | 12/2011 |
| WO | 2012037410 A2 | 3/2012 |
| WO | 2012037411 A2 | 3/2012 |
| WO | 2013056178 A2 | 4/2013 |

OTHER PUBLICATIONS

Zhang et al (Cancer Research, 1997, 57: 1244-1249).*
Herynk, Matthew H. et al., "Estrogen Receptor Mutations in Human Disease", Endocrine Reviews, 25(6):869-898.
International Search Report dated Mar. 22, 2013 from International Application No. PCT/US12/60133.

(Continued)

*Primary Examiner* — Sean E Aeder
(74) *Attorney, Agent, or Firm* — Morrison & Foerster LLP

(57) ABSTRACT

Novel mutant ESR1 molecules and uses are disclosed.

15 Claims, 6 Drawing Sheets
Specification includes a Sequence Listing.

(56) References Cited

OTHER PUBLICATIONS

Mahfoudi, A. et al. "Specific Mutations in the Estrogen Receptor Change the Properties of Antiestrogens to Full Agonists", Proc. Nat'l Acad Sci., USA, May 1995, vol. 92, pp. 4206-4210.
Mohseni, et al., "PIK3CA and KRAS mutations predict for response to everolimus therapy: now that's RAD001" The Journal of Clinical Investigation, 120(8):2655-2658 (2010).
Okubo, et al., "Additive antitumour effect of the epidermal growth factor receptor tyrosine kinase inhibitor gefitinib (Iressa, ZD 1839) and the antioestrogen fulvestrant (Faslodex, ICI 182,780) in breast cancer cells", British Journal of Cancer, 90:236-244 (2004).
Robertson, et al., "ICI 182,780 (Fulvestrant)—the first oestrogen receptor down-regulator—current clinical data", British Journal of Cancer, 85(2):11-14 (2001).
Sabine, et al., "Gene expression profiling of response to mTOR inhibitor everolimus in pre-operatively treated post-menopausal women with oestrogen receptor-positive breast cancer", Breast Cancer Res. Treat, 122:419-428 (2010).
Tremblay, et al., "Ligand-independent Activation of the Estrogen Receptors alpha and beta by Mutations of a Conserved Tyrosine Can Be Abolished by Antiestrogens", Cancer Research, 58:887-881 (1998).
Written Opinion for PCT/US 12/60133 dated Mar. 22, 2013.
Beer et al., (2010). "Preparation and Evaluation of Carborane Analogues of Tamoxifen," J Med Chem, 53:8012-8020.
Riggins et al., (2007). "Pathways to tamoxifen resistance," Cancer Letters, 256:1-24.

\* cited by examiner

FIG. 2A

```
atg acc atg acc ctc cac acc aaa gca tct ggg atg gcc cta ctg cat cag atc caa ggg  60
 M   T   M   T   L   H   T   K   A   S   G   M   A   L   L   H   Q   I   Q   G   20 aac gag ctg gag ccc ctg aac cgt ccg cag ctc aag atc ccc ctg gag cgg ccc ctg ggc 120
 N   E   L   E   P   L   N   R   P   Q   L   K   I   P   L   E   R   P   L   G   40 gag gtg tac ctg gac agc agc aag ccc gcc gtg tac aac tac ccc gag ggc gcc gcc tac 180
 E   V   Y   L   D   S   S   K   P   A   V   Y   N   Y   P   E   G   A   A   Y   60 gag ttc aac gcc gcg gcc gcc gcc aac gcg cag gtc tac ggt cag acc ggc ctc ccc tac 240
 E   F   N   A   A   A   A   N   A   Q   V   Y   G   Q   T   G   L   P   Y   80 ggc ccc ggg tct gag gct gcg gcg ttc ggc tcc aac ggc ctg ggg ggt ttc ccc cca ctc 300
 G   P   G   S   E   A   A   A   F   G   S   N   G   L   G   G   F   P   P   L   100 aac agc gtg tct ccg agc ccg ctg atg cta ctg cac ccg ccg ccg cag ctg tcg cct ttc 360
 N   S   V   S   P   S   P   L   M   L   L   H   P   P   P   Q   L   S   P   F   120 ctg cag ccc cac ggc cag cag gtg ccc tac tac ctg gag aac gag ccc agc ggc tac acg 420
 L   Q   P   H   G   Q   Q   V   P   Y   Y   L   E   N   E   P   S   G   Y   T   140 gtg cgc gag gcc ggc ccg ccg gca ttc tac agg cca aat tca gat aat cga cgc cag ggt 480
 V   R   E   A   G   P   P   A   F   Y   R   P   N   S   D   N   R   R   Q   G   160 ggc aga gaa aga ttg gcc agt acc aat gac aag gga agt atg gct atg gaa tct gcc aag 540
 G   R   E   R   L   A   S   T   N   D   K   G   S   M   A   M   E   S   A   K   180 gag act cgc tac tgt gca gtg tgc aat gac tat gct tca ggc tac cat tat gga gtc tgg 600
 E   T   R   Y   C   A   V   C   N   D   Y   A   S   G   Y   H   Y   G   V   W   200 tcc tgt gag ggc tgc aag gcc ttc ttc aag aga agt att caa gga cat aac gac tat atg 660
 S   C   E   G   C   K   A   F   F   K   R   S   I   Q   G   H   N   D   Y   M   220 tgt cca gcc acc aac cag tgc acc att gat aaa aac agg agg aag agc tgc cag gcc tgc 720
 C   P   A   T   N   Q   C   T   I   D   K   N   R   R   K   S   C   Q   A   C   240 cgg ctc cgc aaa tgc tac gaa gtg gga atg atg aaa ggt ggg ata cga aaa gac cga aga 780
 R   L   R   K   C   Y   E   V   G   M   M   K   G   G   I   R   K   D   R   R   260 gga ggg aga atg ttg aaa cac aag cgc cag aga gat gat ggg gag ggc agg ggt gaa gtg 840
 G   G   R   M   L   K   H   K   R   Q   R   D   D   G   E   G   R   G   E   V   280 ggg tct gct gga gac atg aga gct gcc aac ctt tgg cca agc ccg ctc atg atc aaa cgc 900
 G   S   A   G   D   M   R   A   A   N   L   W   P   S   P   L   M   I   K   R   300
```

FIG. 2B

```
tct aag aag aac agc ctg gcc ttg tcc ctg acg gcc gac cag atg gtc agt gcc ttg ttg 960
 S   K   K   N   S   L   A   L   S   L   T   A   D   Q   M   V   S   A   L   L  320 gat gct gag ccc ccc ata ctc tat tcc gag tat gat cct acc aga ccc ttc agt gaa gct 1020
 D   A   E   P   P   I   L   Y   S   E   Y   D   P   T   R   P   F   S   E   A  340 tcg atg atg ggc tta ctg acc aac ctg gca gac agg gag ctg gtt cac atg atc aac tgg 1080
 S   M   M   G   L   L   T   N   L   A   D   R   E   L   V   H   M   I   N   W  360 gcg aag agg gtg cca ggc ttt gtg gat ttg acc ctc cat gat cag gtc cac ctt cta gaa 1140
 A   K   R   V   P   G   F   V   D   L   T   L   H   D   Q   V   H   L   L   E  380 tgt gcc tgg cta gag atc ctg atg att ggt ctc gtc tgg cgc tcc atg gag cac cca gtg 1200
 C   A   W   L   E   I   L   M   I   G   L   V   W   R   S   M   E   H   P   V  400 aag cta ctg ttt gct cct aac ttg ctc ttg gac agg aac cag gga aaa tgt gta gag ggc 1260
 K   L   L   F   A   P   N   L   L   L   D   R   N   Q   G   K   C   V   E   G  420 atg gtg gag atc ttc gac atg ctg ctg gct aca tca tct cgg ttc cgc atg atg aat ctg 1320
 M   V   E   I   F   D   M   L   L   A   T   S   S   R   F   R   M   M   N   L  440 cag gga gag gag ttt gtg tgc ctc aaa tct att att ttg ctt aat tct gga gtg tac aca 1380
 Q   G   E   E   F   V   C   L   K   S   I   I   L   L   N   S   G   V   Y   T  460 ttt ctg tcc agc acc ctg aag tct ctg gaa gag aag gac cat atc cac cga gtc ctg gac 1440
 F   L   S   S   T   L   K   S   L   E   E   K   D   H   I   H   R   V   L   D  480 aag atc aca gac act ttg atc cac ctg atg gcc aag gca ggc ctg acc ctg cag cag cag 1500
 K   I   T   D   T   L   I   H   L   M   A   K   A   G   L   T   L   Q   Q   Q  500 cac cag cgg ctg gcc cag ctc ctc ctc atc ctc tcc cac atc agg cac atg agt aac aaa 1560
 H   Q   R   L   A   Q   L   L   L   I   L   S   H   I   R   H   M   S   N   K  520 ggc atg gag cat ctg tac agc atg aag tgc aag aac gtg gtg ccc ctc tat gac ctg ctg 1620
 G   M   E   H   L   Y   S   M   K   C   K   N   V   V   P   L   Y   D   L   L  540 ctg gag atg ctg gac gcc cac cgc cta cat gcg ccc act agc cgt gga ggg gca tcc gtg 1680
 L   E   M   L   D   A   H   R   L   H   A   P   T   S   R   G   G   A   S   V  560 gag gag acg gac caa agc cac ttg gcc act gcg ggc tct act tca tcg cat tcc ttg caa 1740
 E   E   T   D   Q   S   H   L   A   T   A   G   S   T   S   S   H   S   L   Q  580 aag tat tac atc acg ggg gag gca gag ggt ttc cct gcc aca gtc tga    1788  SEQ ID NO:1
 K   Y   Y   I   T   G   E   A   E   G   F   P   A   T   V   *      596  SEQ ID NO:2
```

FIG. 4A

```
atg acc atg acc ctc cac acc aaa gca tct ggg atg gcc cta ctg cat cag atc caa ggg  60
 M   T   M   T   L   H   T   K   A   S   G   M   A   L   L   H   Q   I   Q   G   20 aac gag ctg gag ccc ctg aac cgt ccg cag ctc aag atc ccc ctg gag cgg ccc ctg ggc 120
 N   E   L   E   P   L   N   R   P   Q   L   K   I   P   L   E   R   P   L   G   40 gag gtg tac ctg gac agc agc aag ccc gcc gtg tac aac tac ccc gag ggc gcc gcc tac 180
 E   V   Y   L   D   S   S   K   P   A   V   Y   N   Y   P   E   G   A   A   Y   60 gag ttc aac gcc gcg gcc gcc gcc aac gcg cag gtc tac ggt cag acc ggc ctc ccc tac 240
 E   F   N   A   A   A   A   N   A   Q   V   Y   G   Q   T   G   L   P   Y   80 ggc ccc ggg tct gag gct gcg gcg ttc ggc tcc aac ggc ctg ggg ggt ttc ccc cca ctc 300
 G   P   G   S   E   A   A   A   F   G   S   N   G   L   G   G   F   P   P   L  100 aac agc gtg tct ccg agc ccg ctg atg cta ctg cac ccg ccg ccg cag ctg tcg cct ttc 360
 N   S   V   S   P   S   P   L   M   L   L   H   P   P   P   Q   L   S   P   F  120 ctg cag ccc cac ggc cag cag gtg ccc tac tac ctg gag aac gag ccc agc ggc tac acg 420
 L   Q   P   H   G   Q   Q   V   P   Y   Y   L   E   N   E   P   S   G   Y   T  140 gtg cgc gag gcc ggc ccg ccg gca ttc tac agg cca aat tca gat aat cga cgc cag ggt 480
 V   R   E   A   G   P   P   A   F   Y   R   P   N   S   D   N   R   Q   G  160 ggc aga gaa aga ttg gcc agt acc aat gac aag gga agt atg gct atg gaa tct gcc aag 540
 G   R   E   R   L   A   S   T   N   D   K   G   S   M   A   M   E   S   A   K  180 gag act cgc tac tgt gca gtg tgc aat gac tat gct tca ggc tac cat tat gga gtc tgg 600
 E   T   R   Y   C   A   V   C   N   D   Y   A   S   G   Y   H   Y   G   V   W  200 tcc tgt gag ggc tgc aag gcc ttc ttc aag aga agt att caa gga cat aac gac tat atg 660
 S   C   E   G   C   K   A   F   F   K   R   S   I   Q   G   H   N   D   Y   M  220 tgt cca gcc acc aac cag tgc acc att gat aaa aac agg agg aag agc tgc cag gcc tgc 720
 C   P   A   T   N   Q   C   T   I   D   K   N   R   R   K   S   C   Q   A   C  240 cgg ctc cgc aaa tgc tac gaa gtg gga atg atg aaa ggt ggg ata cga aaa gac cga aga 780
 R   L   R   K   C   Y   E   V   G   M   M   K   G   G   I   R   K   D   R   R  260 gga ggg aga atg ttg aaa cac aag cgc cag aga gat gat ggg gag ggc agg ggt gaa gtg 840
 G   G   R   M   L   K   H   K   R   Q   R   D   D   G   E   G   R   G   E   V  280 ggg tct gct gga gac atg aga gct gcc aac ctt tgg cca agc ccg ctc atg atc aaa cgc 900
 G   S   A   G   D   M   R   A   A   N   L   W   P   S   P   L   M   I   K   R  300
```

FIG. 4B

```
tct aag aag aac agc ctg gcc ttg tcc ctg acg gcc gac cag atg gtc agt gcc ttg ttg  960
 S   K   K   N   S   L   A   L   S   L   T   A   D   Q   M   V   S   A   L   L  320 gat gct gag ccc ccc ata ctc tat tcc gag tat gat cct acc aga ccc ttc agt gaa gct 1020
 D   A   E   P   P   I   L   Y   S   E   Y   D   P   T   R   P   F   S   E   A  340 tcg atg atg ggc tta ctg acc aac c|ac agg gag ctg gtt cac atg atc aac tgg gcg aag 1080
 S   M   M   G   L   L   T   N   H   R   E   L   V   H   M   I   N   W   A   K  360 agg gtg cca ggc ttt gtg gat ttg acc ctc cat gat cag gtc cac ctt cta gaa tgt gcc 1140
 R   V   P   G   F   V   D   L   T   L   H   D   Q   V   H   L   L   E   C   A  380 tgg cta gag atc ctg atg att ggt ctc gtc tgg cgc tcc atg gag cac cca gtg aag cta 1200
 W   L   E   I   L   M   I   G   L   V   W   R   S   M   E   H   P   V   K   L  400 ctg ttt gct cct aac ttg ctc ttg gac agg aac cag gga aaa tgt gta gag ggc atg gtg 1260
 L   F   A   P   N   L   L   L   D   R   N   Q   G   K   C   V   E   G   M   V  420 gag atc ttc gac atg ctg ctg gct aca tca tct cgg ttc cgc atg atg aat ctg cag gga 1320
 E   I   F   D   M   L   L   A   T   S   S   R   F   R   M   M   N   L   Q   G  440 gag gag ttt gtg tgc ctc aaa tct att att ttg ctt aat tct gga gtg tac aca ttt ctg 1380
 E   E   F   V   C   L   K   S   I   I   L   L   N   S   G   V   Y   T   F   L  460 tcc agc acc ctg aag tct ctg gaa gag aag gac cat atc cac cga gtc ctg gac aag atc 1440
 S   S   T   L   K   S   L   E   E   K   D   H   I   H   R   V   L   D   K   I  480 aca gac act ttg atc cac ctg atg gcc aag gca ggc ctg acc ctg cag cag cag cac cag 1500
 T   D   T   L   I   H   L   M   A   K   A   G   L   T   L   Q   Q   Q   H   Q  500 cgg ctg gcc cag ctc ctc ctc atc ctc tcc cac atc agg cac atg agt aac aaa ggc atg 1560
 R   L   A   Q   L   L   L   I   L   S   H   I   R   H   M   S   N   K   G   M  520 gag cat ctg tac agc atg aag tgc aag aac gtg gtg ccc ctc tat gac ctg ctg ctg gag 1620
 E   H   L   Y   S   M   K   C   K   N   V   V   P   L   Y   D   L   L   L   E  540 atg ctg gac gcc cac cgc cta cat gcg ccc act agc cgt gga ggg gca tcc gtg gag gag 1680
 M   L   D   A   H   R   L   H   A   P   T   S   R   G   G   A   S   V   E   E  560 acg gac caa agc cac ttg gcc act gcg ggc tct act tca tcg cat tcc ttg caa aag tat 1740
 T   D   Q   S   H   L   A   T   A   G   S   T   S   S   H   S   L   Q   K   Y  580 tac atc acg ggg gag gca gag ggt ttc cct gcc aca gtc tga     1782   SEQ ID NO:3
 Y   I   T   G   E   A   E   G   F   P   A   T   V   *      594    SEQ ID NO:4
```

ESTROGEN RECEPTOR MUTATIONS AND USES THEREOF

RELATED APPLICATIONS

This application is a continuation of U.S. application Ser. No. 15/018,640, filed Feb. 8, 2016, now abandoned, which is a continuation of U.S. application Ser. No. 14/753,397, filed Jun. 29, 2015, now allowed, which is continuation of U.S. application Ser. No. 14/251,856, filed Apr. 14, 2014, now abandoned, which is a continuation of PCT/US2012/060133, filed Oct. 12, 2012, which claims the benefit of U.S. Provisional Application No. 61/547,471, filed Oct. 14, 2011, and U.S. Provisional Application No. 61/615,821, filed Mar. 26, 2012. The contents of each these prior applications are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 8, 2016, is named F2036-703423_SL.txt and is 30,651 bytes in size.

BACKGROUND

Cancer represents the phenotypic end-point of multiple genetic lesions that endow cells with a full range of biological properties required for tumorigenesis. Indeed, a hallmark genomic feature of many cancers, including, for example, breast cancer, prostate cancer, ovarian cancer, endometrial cancer, and colon cancer, is the presence of numerous complex chromosome structural aberrations, including translocations, intra-chromosomal inversions, point mutations, deletions, gene copy number changes, gene expression level changes, and germline mutations, among others.

The need still exists for identifying novel genetic lesions associated with cancer. Such genetic lesions can be an effective approach to develop compositions, methods and assays for evaluating and treating cancer patients.

SUMMARY

The invention is based, at least in part, on the discovery of novel mutations in the Estrogen Receptor 1 (ESR1) gene in a cancer, e.g., a breast, a colorectal, or a lung, cancer. In one embodiment, the mutation is a deletion in the ligand binding domain of the ESR1 gene, e.g., the human ESR1 gene. In other embodiments, the mutation is a missense mutation in the hinge domain or the ligand binding domain of the ESR1 gene, e.g., the human ESR1 gene.

In one embodiment, a mutant ESR1 (e.g., a mutant ESR1 nucleic acid or polypeptide) includes a mutation in the hinge domain and/or the ligand binding domain, e.g., a missense mutation or an in-frame deletion of 3 or more nucleotides, in one or more of ESR1 exons, e.g., exons 8-12 of ESR1 (FIG. 1). For example, an ESR1 mutation includes a 6 nucleotide deletion of nucleotides 1046-1051 (TGGCAG) according to SEQ ID NO:1, which results in the deletion of amino acids 349-351 (LAD) and an insertion of H at amino acid position 349 (FIG. 4B). In other embodiments, an ESR1 mutation includes a mutation, e.g., a missense mutation, shown in Table 3, e.g., one or more of mutations at position 311, 341, 350, 394, 414, 433, 503, 537 or 538 of the amino acid sequence of SEQ ID NO:2 (FIGS. 2A-2B); or one or more mutations at positions 932, 1022, 1049, 1181, 1240, 1297, 1507, 1609, 1610 or 1613 of the nucleotide sequence of SEQ ID NO:1 (FIGS. 2A-2B). In one embodiment, the ESR1 mutation includes a missense mutation at amino acid 538 of SEQ ID NO:2, or nucleotide 1613 of SEQ ID NO:1. In one embodiment, the missense mutation is chosen from one or more of: a threonine to methionine substitution at position 311 (a T311M); a serine to leucine substitution at position 341 (a S341L); an alanine to glutamate substitution at position 350 (a A350E); an arginine to histidine substitution at position 394 (a R394H); a glutamine substitution at position 414, e.g., an insertion to a stop codon (a Q414*); a serine to proline substitution at position 433 (a S433P); an arginine to tryptophan substitution at position 503 (a R503W); a tyrosine to asparagine substitution at position 537 (a Y537N); a tyrosine to cysteine substitution at position 537 (a Y537C); or an aspartate to glycine substitution at position 538 (a D538G), of SEQ ID NO:2. In one embodiment, the mutation is an aspartate to glycine substitution at position 538 (a D538G), of SEQ ID NO:2. In other embodiments, the mutation is a nucleotide mutation chosen from one or more of: a C to T replacement at nucleotide 932; a C to T replacement at nucleotide 1022; a C to A replacement at nucleotide 1049; a G to A replacement at nucleotide 1181A; a C to T replacement at nucleotide 1240; a T to C replacement at nucleotide 1297; a T to A replacement at nucleotide 1609; an A to G replacement at nucleotide 1610; or an A to G replacement at nucleotide 1613, of SEQ ID NO:1. In one embodiment, the mutation is an A to G replacement at nucleotide 1613, of SEQ ID NO:1. In one embodiment, the mutation is an insertion of a C between amino acids G344 and L345 of SEQ ID NO:2; an insertion of nucleotides GCT between nucleotides 1032 and 1033 of SEQ ID NO:1.

In one embodiment, a mutant ESR1 includes a mutation in the hinge region, e.g., a mutation that causes an amino acid substitution at position 311 of SEQ ID NO:2, e.g., a T311M mutation. In one embodiment, the mutation features a C932T substitution according to the sequence of SEQ ID NO:1.

In one embodiment, a mutant ESR1 includes a mutation in the ligand binding domain, e.g., a mutation that causes an amino acid substitution at position 341 of SEQ ID NO:2, e.g., a S341L mutation. In one embodiment, the mutation features a C1022T substitution according to the sequence of SEQ ID NO:1.

In one embodiment, a mutant ESR1 includes a mutation in the ligand binding domain, e.g., a mutation that causes an amino acid insertion between amino acids G344 and L345 of SEQ ID NO:2, e.g., an insertion of a C amino acid. In one embodiment, the mutation features an insertion of nucleotides GCT between nucleotides 1032 and 1033 of SEQ ID NO:1.

In one embodiment, a mutant ESR1 includes a mutation in the ligand binding domain, e.g., a mutation that causes an amino acid substitution at position 350 of SEQ ID NO:2, e.g., an A350E mutation. In one embodiment, the mutation features a C1049A substitution according to the sequence of SEQ ID NO:1.

In one embodiment, a mutant ESR1 includes a mutation in the ligand binding domain, e.g., a mutation that causes an amino acid substitution at position 394 of SEQ ID NO:2, e.g., an R394H mutation. In one embodiment, the mutation features a G1181A substitution according to the sequence of SEQ ID NO:1.

In one embodiment, a mutant ESR1 includes a mutation in the ligand binding domain, e.g., a mutation that results in a truncated protein that ends at position 413 of SEQ ID NO:2, e.g., a Q414* mutation, due to a mutation in the nucleotide sequence that introduces a stop codon, e.g., a C1240T substitution according to the sequence of SEQ ID NO:1.

In one embodiment, a mutant ESR1 includes a mutation in the ligand binding domain, e.g., a mutation that causes an amino acid substitution at position 433 of SEQ ID NO:2, e.g., an S433P mutation. In one embodiment, the mutation features a T1297C substitution according to the sequence of SEQ ID NO:1.

In one embodiment, a mutant ESR1 includes a mutation in the ligand binding domain, e.g., a mutation that causes an amino acid substitution at position 503 of SEQ ID NO:2, e.g., an R503W mutation. In one embodiment, the mutation features a C1507T substitution according to the sequence of SEQ ID NO:1.

In one embodiment, a mutant ESR1 includes a mutation in the ligand binding domain, e.g., a mutation that causes an amino acid substitution at position 537 of SEQ ID NO:2, e.g., an Y537N mutation or a Y537C. In one embodiment, the mutation features a Y537N mutation according to the sequence of SEQ ID NO:2, and a corresponding T1609A substitution according to the sequence of SEQ ID NO:1. In another embodiment, the mutation features a Y537C mutation according to the sequence of SEQ ID NO:2, and a corresponding A1610G substitution according to the sequence of SEQ ID NO:1.

In one embodiment, a mutant ESR1 includes a mutation in the ligand binding domain, e.g., a mutation that causes an amino acid substitution at position 538 of SEQ ID NO:2, e.g., an D538G mutation. In one embodiment, the mutation features a A1613G substitution according to the sequence of SEQ ID NO:1.

A mutant polypeptide encoded by a mutant ESR1 nucleic acid is sometimes referred to herein as a "mutant ESR1 polypeptide." In an embodiment, the mutant ESR1 polypeptide can have an alteration in one or more of the following activities: a ligand binding activity (e.g., an aleration in its ability to bind to estrogen or an estrogen mimetic), a DNA binding activity, an interaction with a co-repressor, an interaction with a co-activator (e.g., to activate transcription). In one embodiment, the mutant ESR1 polypeptide has an altered ligand binding activity, an altered dimerization activity, an altered translocation activity, an altered AF-2 function, and/or impaired ER signaling, e.g., compared to an ESR1 polypeptide that does not have the mutation, e.g., a wild type ESR1 polypeptide. In other embodiments, the mutant ESR1 polypeptide is constitutively active, e.g., has a constitutively active transcriptional activity, compared to an ESR1 polypeptide that does not have the mutation, e.g., a wild type ESR1 polypeptide. In certain embodiments, the mutant ESR1 polypeptide has at least one activity that is not substantially affected by an ESR1 agonist or antagonist (e.g., estradiol, tamoxifen or other anti-estrogen agent or "Selective Estrogen Receptor Modulator" (SERM)). In other embodiment, the mutant ESR1 polypeptide has altered (e.g., reduced) phosphorylation at position 537 of SEQ ID NO:2. In some embodiments, a mutant ESR1 is activated, or has enhanced activity when contacted with a SERM, such as tamoxifen, as compared to the activity of an ESR1 polypeptide that does not carry the mutation. An enhanced activity of a mutant ESR1 can exhibit constitutive or enhanced activity, e.g., in a cell of a cancer referred to herein (e.g., a breast cancer (e.g., a SERM-resistant breast cancer), a colorectal cancer, or a lung cancer). The constitutive or enhanced activity can be enhanced transcriptional activation as compared to an ESR1 that does not carry the mutation. A cell of a cancer can carry an ESR1 nucleic acid and polypeptide that contains a mutation in the ligand binding domain described herein, e.g., a 6 nucleotide deletion in the ligand binding domain, an insertion or missense mutation, and can also carry an ESR1 nucleic acid and polypeptide that does not carry the mutation.

In one embodiment, the mutant ESR1 comprises at least 1, 2, 3, 4, 5, 6, 7, 8, 9, 10, 11 or 12 exons from ESR1. In another embodiment, the mutant ESR1 polypeptide includes an activation function domain-1 (AF-1), a DNA binding domain, a hinge domain, and a ligand binding domain containing an activation function 2 (AF-2) domain, or a functional fragment thereof. In another embodiment, the mutant ESR1 polypeptide includes a DNA binding domain, a hinge domain, and a ligand binding domain containing an activation function 2 (AF-2) domain, or a functional fragment thereof.

In certain embodiments, the mutant ESR1 is identified in a subject, e.g., a patient who is positive for an estrogen receptor (e.g., an ER positive (ER+) subject as detected, e.g., by immunohistochemistry). In other embodiments, the subject is identified, or has been previously identified, as having a cancer with an ER+ status (e.g., a cancer that grows in response to an estrogen). In certain embodiments, the subject has a localized cancer, e.g., a localized breast cancer. In other embodiments, the subject has a metastatic cancer. In certain embodiment, the subject has a late stage or advanced breast cancer, e.g., a late state progressive metastatic cancer. In other embodiments, the subject has an ER positive, late stage or advance breast cancer, e.g., an ER positive, metastatic breast cancer. In one embodiment, the subject is an ER+ breast cancer patient with late stage, progressive metastatic cancer.

In certain embodiments, the subject is currently undergoing treatment with a SERM (e.g., tamoxifen) or other anti-estrogen. In other embodiments, the subject is currently undergoing treatment with an aromatase inhibitor. In yet other embodiments, the subject is undergoing treatment with chemotherapy. In other embodiment, the subject is undergoing treatment with a Her 2 inhibitor, e.g., an anti-Her 2 antibody (e.g., HERCEPTIN). In certain embodiments, the subject (e.g., an ER+ subject) shows a decrease response or is non-responsive (or resistant) to a treatment with one or more of SERM, an aromatase inhibitor, a chemotherapy, or a Her 2 inhibitor. In certain embodiment, the subject is further evaluated for the presence of one or more of the mutations disclosed herein. In one embodiment, the treatment of the subject, e.g., the treatment with one or more of the SERM, the aromatase inhibitor, the chemotherapy, or the Her 2 inhibitor is modified, e.g., decreased, discontinued, or otherwise altered, in response to the detection of one or more of the mutations described herein. In one embodiment, the treatment modified is a treatment with the SERM.

In one embodiment, identification of a mutation in the ligand binding domain of ESR1 is indicative that the cancer is less responsive to hormone therapy (e.g., the cancer is hormone-resistant). In certain embodiment, the presence of an ESR mutant is indicative of disease progression. In certain embodiments, the mutation is not identified in the primary cancer. In other embodiments, the mutation is identified in metastatic cancer. In certain embodiment, the mutation is identified in a late stage or advanced breast cancer, e.g., a late state progressive metastatic cancer. In other embodiments, the mutation is identified in an ER positive, late stage or advance breast cancer, e.g., an ER positive, metastatic breast cancer. In one embodiment, the mutation is identified in an ER+ breast cancer patient with late stage, progressive metastatic cancer.

In certain embodiments, a cancer patient having a mutation in the ligand binding domain of ESR1 can be administered an anti-cancer therapy that is not a SERM. In one embodiment, the other anti-cancer therapy is an aromatase inhibitor. In other embodiments, the other therapy is an mTOR (mammalian Target of Rapamycin) pathway inhibitor, for example, RAD001 (everolimus), CCI-799 (tensirolimus), and AP23573 (ARIAD). For example, in one embodiment, the subject is a post-menopausal female, and identification of a mutation in the ligand binding domain of ESR1, indicates that a cancer patient can be administered an estrogen inhibitor, such as an aromatase inhibitor or fulvestrant, alone or in combination with an mTOR pathway inhibitor. In another embodiment, the subject is a premenopausal female, and the identification of a mutation in the ligand binding domain of ESR1 indicates that the patient can be administered an estrogen receptor blocking agent or should have an oophorectomy (ovary removal). In one embodiment, identification of a mutation in the ligand binding domain of ESR1 indicates that a cancer patient should not be administered a SERM, such as tamoxifen or raloxifene. In yet other embodiments, a post-menopausal female or a premenopausal female identified as carrying a mutation in the ligand binding domain of ESR continues to receive treatment with a SERM (e.g., at the same or a reduced dose of the SERM). In other embodiments, the anti-cancer therapy includes an aromatase inhibitor (e.g., examestane), alone or in combination with an mTOR pathway inhibitor, for example, RAD001 (everolimus).

In one embodiment, a subject, e.g., a cancer patient is already receiving therapy with a SERM, e.g., tamoxifen, and the identification of a mutation in ESR1 indicates that the patient can receive an alternate therapy, e.g., the patient should stop receiving treatment with a SERM, or reduce the dose of a SERM, and/or begin therapy with an alternative therapy.

In one embodiment, the alternative therapy includes an aromatase inhibitor (e.g., anastrozole), a Selective Estrogen Receptor Downregulator (SERD) or anti-estrogen (e.g., fulvestrant), or an mTOR pathway inhibitor, or a combination thereof.

In another embodiment, the alternate therapy reduces or inhibits the constitutive activation of an ESR1, e.g., a mutant ESR1 as described herein. In one embodiment, the alternative therapy reduces or inhibits one or more of: a ligand binding activity, receptor translocation, DNA binding activity, receptor dimerization, or an interaction with a co-activator (e.g., to activate transcription).

In other embodiments, the alternative therapy reduces the level of an ESR1, e.g., a mutant ESR1 as described herein (e.g., a constitutively active ESR1). For example, the alternative therapy reduces the expression or the stability of an ESR1 gene product; and/or increases ESR1 degradation. In one embodiment, the alternative therapy includes administration a Selective Estrogen Receptor Downregulator (SERD). In one embodiment, the alternative therapy is a non-steroidal ERα antagonist that induces ERα degradation. In other embodiments, the alternative therapy inhibits or reduces ERα transcriptional activity and/or steady state levels. Exemplary estrogen receptor modulators that can be used as an alternative therapy are described in, e.g., WO 2012/037411, WO 2012/037410, WO 2011/159769, WO 2011/156518 and US 2012/0071535, the contents of all of which are hereby incorporated by reference.

In yet other embodiments, the alternative therapy is a tamoxifen analogue.

In another embodiment, the alternate therapy is a reduction in the dose of SERM therapy, and/or the addition of an anti-cancer therapy that is not a SERM. For example, an aromatase inhibitor can be administered in addition to the lower dose of the SERM therapy. Typically, a subject who is a candidate to receive treatment with an aromatase inhibitor is a post-menopausal female. A premenopausal female is typically not a candidate to receive treatment with an aromatase inhibitor.

In another embodiment, alternative therapies can include administration of an inhibitor of other steroid receptors, such as inhibitors of retinoic acid receptors. Retinoic acid receptors (including retinoid X receptors) are known to interact with estrogen receptors. Alternative therapeutic therapies include inhibition of retinoic acid receptor activity. Therapeutic strategies based on RXR and RAR modulators for cancer treatment are reviewed in Altucci, L. et al. (2007) *Nature Reviews Drug Discovery* 6:793-810.

In one embodiment, a patient, such as a breast cancer patient, receiving therapy with a SERM (e.g., tamoxifen), can be monitored, e.g., monthly, every two months, or every 3, 4, 5, 6, 7, 8, 9 or 10 months, or yearly for the presence of an ESR1 mutation (e.g., an ESR mutation described herein). In one embodiment, the subject is positive for an estrogen receptor (e.g., an ER positive subject as detected, e.g., by immunohistochemistry). If during the course of treatment with a SERM, the patient develops a mutation in the ESR1 domain described herein, e.g., in the vicinity of T311, 5341, A350, G344, D351, R394, Q414, 5433, R503, Y537, and/or D538, the patient can stop treatment with the SERM. In some embodiments, the patient will not stop treatment with the SERM or will be administered a lower dose of the SERM, and optionally, the patient will receive enhanced monitoring (e.g., more frequent monitoring) for signs of increased cancer symptoms, e.g., increased tumor size, metastasis, or spread of the tumor to other organs or tissues.

In one embodiment, the subject, e.g., patient, who develops a mutation in the ESR1 domain, e.g., in the vicinity of T311, 5341, G344, A350, D351, R394, Q414, S433, R503, Y537, and/or D538, is a post-menopausal female who will stop treatment with the SERM, and who and will begin treatment with an aromatase inhibitor, an anti-estrogen, a SERD, an estrogen receptor modulator as described herein, fulvestrant (Faslodex®) and/or an mTOR pathway inhibitor.

In yet other embodiments, the subject has one or more mutations in addition to the mutation of the ESR1 domain. Examples of such mutations can be found in Table 3, and include a HER2 mutation (e.g., HER2 amplification), a p53 mutation, BRCA, NF1, EGFR/myc gains, PIK3CA, CCND1 and CDH1. Thus, the subjects can receive a therapy that target the ESR1 mutation, alone or in combination with a therapy that targets another mutation identified as part of the cancer, e.g., a drug that targets mutant HER2 mutation (e.g., HER2 amplification), a p53 mutation, BRCA, NF1, EGFR/myc gains, PIK3CA, CCND1 and/or CDH1.

The invention provides methods of identifying, assessing or detecting a mutant ESR1; methods of identifying, assessing, evaluating, and/or treating a subject having a cancer, e.g., a cancer having a mutant ESR1; isolated mutant ESR1 nucleic acid molecules, nucleic acid constructs, and host cells containing the nucleic acid molecules; purified mutant ESR1 polypeptides and binding agents; detection reagents (e.g., probes, primers, antibodies, kits, e.g., capable of specific detection of a mutant ESR1 nucleic acid or protein); screening assays for identifying molecules that interact with, e.g., inhibit, mutant ESR1, e.g., novel estrogen receptor inhibitors; as well as assays and kits for evaluating, identifying, assessing and/or treating a subject having a cancer, e.g., a cancer having a mutant ESR1, e.g., an ESR1 carrying a mutation in the ligand binding domain. The compositions and methods identified herein can be used, for example, to identify new estrogen receptor inhibitors; to evaluate, identify or select a subject, e.g., a patient, having a cancer; and to treat or prevent a cancer.

Mutant ESR1 Nucleic Acid Molecules

In one aspect, the invention features a nucleic acid molecule (e.g., an isolated or purified) nucleic acid molecule that includes a fragment of an ESR1 gene, including the ligand binding domain (also called the hormone binding domain or the AF-2 domain). In embodiments, the fragment also includes a DNA binding domain and a hinge domain. In some embodiments, the fragment also includes an AF-1 domain (see FIG. 1). In one embodiment, the nucleic acid molecule includes an exon of ESR1 (e.g., one or more exons encoding a ligand binding domain, a DNA binding domain, a hinge domain and an AF-1 domain).

In an embodiment, the mutant ESR1 nucleic acid molecule comprises sufficient ESR1 sequence such that the encoded ESR1 polypeptide has transcriptional activation activity or DNA binding activity, e.g., has elevated activity, as compared with a reference ESR1, e.g., a wildtype ESR1, e.g., in a cell of a cancer referred to herein. In an embodiment the encoded mutant ESR1 comprises at least 1, 2, 3, 4, 5, 6, 7, 8, 9, 10, 11, or 12 exons from ESR1. The exons are numbered according to RefSeq NM_001122742 (Oct. 2, 2011). In one embodiment, the encoded mutant ESR1 polypeptide, or functional fragment thereof, includes a ligand binding domain, a hinge domain, a DNA binding domain, and an AF-1 domain.

In one embodiment, the nucleic acid molecule includes a nucleotide sequence that has an in-frame deletion in exon 8 of ESR1. In other embodiments, the nucleic acid molecule includes a nucleotide sequence in the region of 152,265,390 to 152,265,600 of chromosome 6. In another embodiment, the nucleic acid molecule includes a nucleotide sequence that includes a breakpoint, e.g., a breakpoint identified in FIGS. 1 and 4B. For example, the nucleic acid molecule includes a nucleotide sequence that includes the fusion junction created by the deletion of 6 nucleotides in exon 8 of ESR1, e.g., a nucleotide sequence that includes a portion of SEQ ID NO:3 (e.g., a nucleotide sequence within exons 1-12 of an ESR1 gene) (e.g., a portion of SEQ ID NO:3 comprising nucleotides 1021-1081, 1033-1071, or 1036-1060 of SEQ ID NO:3 (see FIG. 4B)).

In one embodiment, the nucleic acid molecule includes the nucleotide sequence of nucleotides 1-1782 of SEQ ID NO:3 (corresponding to exons 5b (in part) to 12 (in part) of the ESR1 gene), or a fragment thereof, or a sequence substantially identical thereto. In another embodiment, the nucleic acid molecule includes the nucleotide sequence of nucleotides 553-1782 of SEQ ID NO:3 (e.g., corresponding to exons 6 (in part) to 12 (in part) of the ESR1 gene), or a fragment thereof, or a sequence substantially identical thereto. In yet other embodiments, the nucleic acid molecule includes the nucleotide sequence shown in FIGS. 4A to 4B (e.g., SEQ ID NO:3) or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:3 or a fragment thereof. In yet other embodiments, the nucleic acid molecule hybridizes to a nucleotide sequence that is complementary to at least a portion of a nucleotide sequence disclosed herein, e.g., is capable of hybridizing under a stringency condition described herein to a nucleotide sequence complementary to SEQ ID NO:3 or a fragment thereof. The nucleotide sequence of a cDNA encoding an exemplary mutant ESR1 is shown in SEQ ID NO:3, and the amino acid sequence is shown in SEQ ID NO:4.

In one embodiment the nucleic acid molecule includes the nucleotide sequence of nucleotides 1 to 1788 of SEQ ID NO:1, and further comprising one or more of the point mutations in Table 3. In other embodiments, the mutation is a nucleotide mutation chosen from one or more of: a C to T replacement at nucleotide 932; a C to T replacement at nucleotide 1022; a C to A replacement at nucleotide 1049; a G to A replacement at nucleotide 1181A; a C to T replacement at nucleotide 1240; a T to C replacement at nucleotide 1297; a T to A replacement at nucleotide 1609; an A to G replacement at nucleotide 1610; or an A to G replacement at nucleotide 1613, of SEQ ID NO:1. In one embodiment, the mutation is an A to G replacement at nucleotide 1613, of SEQ ID NO:1.

In other embodiments, the nucleic acid molecule includes a nucleotide sequence encoding a mutant ESR1 polypeptide that includes a fragment of a mutant ESR1 gene. In one embodiment, the nucleotide sequence encodes a mutant ESR1 gene that includes a ligand binding domain or a functional fragment thereof. In another embodiment, the nucleotide sequence encodes a fragment of the mutant ESR1 polypeptide including the amino acid sequence of amino acids 1-593 of SEQ ID NO:4 or a fragment thereof, or a sequence substantially identical thereto. For example, the nucleic acid molecule can include a nucleotide sequence encoding a ligand binding domain of an ESR1 polypeptide that includes amino acids 312-544 of SEQ ID NO:4 or a fragment thereof.

In a related aspect, the invention features nucleic acid constructs that include the mutant ESR1 nucleic acid molecules described herein. In certain embodiments, the nucleic acid molecules are operatively linked to a native or a heterologous regulatory sequence. Also included are vectors and host cells that include the ESR1 nucleic acid molecules described herein, e.g., vectors and host cells suitable for producing the nucleic acid molecules and polypeptides described herein.

In a related aspect, methods of producing the nucleic acid molecules and polypeptides described herein are also described.

In another aspect, the invention features nucleic acid molecules that reduce or inhibit the expression of a nucleic acid molecule that encodes a mutant ESR1 described herein. Examples of such nucleic acid molecules include, for example, antisense molecules, ribozymes, RNAi, triple helix molecules that hybridize to a nucleic acid encoding a mutant ESR1, or a transcription regulatory region of mutant ESR1, and blocks or reduces mRNA expression of mutant ESR1.

In one aspect, the invention features a nucleic acid molecule (e.g., an isolated or purified) that includes a mutation identified in Table 1 or Table 2.

Nucleic Acid Detection and Capturing Reagents

The invention also features a nucleic acid molecule, e.g., nucleic acid fragment, suitable as probe, primer, bait or library member that includes, flanks, hybridizes to, and which are useful for identifying, or are otherwise based on, the ESR1 mutants described herein. In certain embodiments, the probe, primer or bait molecule is an oligonucleotide that allows capture, detection or isolation of a mutant ESR1 nucleic acid molecule described herein. The oligonucleotide can include a nucleotide sequence substantially complementary to a fragment of an ESR1 nucleic acid molecule described herein. The sequence identity between the nucleic acid fragment, e.g., the oligonucleotide, and the target mutant ESR1 sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in lenth.

In one embodiment, the nucleic acid fragment can be used to identify or capture, e.g., by hybridization, a mutant ESR1. For example, the nucleic acid fragment can be a probe, a primer, or a bait, for use in identifying or capturing, e.g., by hybridization, a mutant ESR1 described herein. In one embodiment, the nucleic acid fragment can be useful for identifying or capturing an ESR1 breakpoint, e.g., as identified in FIG. 1 and in FIG. 4B. In one embodiment, the nucleic acid fragment hybridizes to a nucleotide sequence within a chromosomal deletion of three nucleotides or more that creates an in-frame fusion of nucleotides within exon 8 of ESR1 (e.g., a sequence within chromosome 6, at exon 8 of ESR1). In one embodiment, the nucleic acid fragment hybridizes to a nucleotide sequence in the region of 152,265,590-152,265,600 of chromosome 6. In one embodiment, the nucleic acid fragment hybridizes to a nucleotide sequence that includes a breakpoint, e.g., a breakpoint as identified in FIGS. 1 and 4B. For example, the nucleic acid fragment can hybridize to a nucleotide sequence that includes the fusion junction created by the deletion of 6 nucleotides in exon 8 of ESR1, e.g., a nucleotide sequence that includes a portion of SEQ ID NO:3 (e.g., a nucleotide sequence within exons 1-12 of an ESR1 gene) (e.g., a portion of SEQ ID NO:3 comprising nucleotides 1021-1081, 1033-1071, or 1036-1060 of SEQ ID NO:3 (see FIG. 4B)).

The probes or primers described herein can be used, for example, for FISH detection or PCR amplification. In one exemplary embodiment where detection is based on PCR, amplification of an ESR1 mutation, such as a deletion junction in the ligand binding domain, can be performed using a primer or a primer pair, e.g., for amplifying a sequence flanking the ESR1 deletion junction described herein. In one embodiment, a pair of isolated oligonucleotide primers can amplify a region containing or adjacent to an ESR1 mutation. For example, forward primers can be designed to hybridize to a nucleotide sequence within ESR1 genomic or mRNA sequence (e.g., a nucleotide sequence within exons 1-8 of an ESR1 gene, or nucleotides 1-1053 of SEQ ID NO:3), and the reverse primers can be designed to hybridize to a nucleotide sequence within ESR1 (e.g., a nucleotide sequence within exons 8-12 of ESR1, or nucleotides 1036-1782 of SEQ ID NO:3).

In another embodiment, the nucleic acid fragments can be used to identify, e.g., by hybridization, a mutant ESR1. In one embodiment, the nucleic acid fragment hybridizes to a nucleotide sequence that includes a fusion junction created by a deletion in exon 8 of an ESR1 transcript, e.g., a nucleotide sequence within SEQ ID NO:3 (e.g., a sequence comprising nucleotides 1021-1081, 1033-1071, or 1036-1060 of SEQ ID NO:3 (see FIG. 4B)). In other embodiments, the nucleic acid fragment detects (e.g., hybridizes to) a nucleotide mutation chosen from one or more of: a C to T replacement at nucleotide 932; a C to T replacement at nucleotide 1022; a C to A replacement at nucleotide 1049; a G to A replacement at nucleotide 1181A; a C to T replacement at nucleotide 1240; a T to C replacement at nucleotide 1297; a T to A replacement at nucleotide 1609; an A to G replacement at nucleotide 1610; or an A to G replacement at nucleotide 1613, of SEQ ID NO:1. In one embodiment, the mutation is an A to G replacement at nucleotide 1613, of SEQ ID NO:1.

In other embodiments, the nucleic acid fragment includes a bait that comprises a nucleotide sequence that hybridizes to a mutant ESR1 nucleic acid molecule described herein, and thereby allows the capture or isolation of said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a mutant ESR1 nucleic acid molecule described herein. In one embodiment, the library member includes a non-frameshift deletion in the ligand binding domain of ESR1.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

Mutant ESR1 Polypeptides

In another aspect, the invention features a mutant ESR1 polypeptide (e.g., a purified mutant ESR1 polypeptide), a biologically active or antigenic fragment thereof, as well as reagents (e.g., antibody molecules that bind to a mutant ESR1 polypeptide), methods for modulating a mutant ESR1 polypeptide activity and detection of a mutant ESR1 polypeptide. In one embodiment, the mutant ESR1 polypeptide has at least one biological activity, e.g., a ligand binding activity, transcriptional activation activity and/or a DNA binding activity. These activities can include interaction with the ESR1 mutant polypeptide with coactivators such as Tif2, Src-1, and Grip1. In one embodiment, at least one biological activity of a mutant ESR1 polypeptide is reduced or inhibited by an anti-cancer drug, e.g., estrogen inhibitor, such as a SERM or an aromatase inhibitor, a SERD or an estrogen receptor modulator as described herein.

In other embodiments, the mutant ESR1 polypeptide includes a fragment of a mutant ESR1 polypeptide containing a mutation in the ligand binding domain. In one embodiment, the mutant ESR1 polypeptide includes amino acids 340-360 of SEQ ID NO:4 or a fragment thereof (e.g., amino acids 1-593 of SEQ ID NO:4 or a fragment thereof). In yet other embodiments, the mutant ESR1 polypeptide includes an amino acid sequence substantially identical to a non-frameshift deletion of amino acids 349-351 of SEQ ID NO:2 or a fragment thereof. In other embodiments, the mutation is a missense mutation. In one embodiment, the missense mutation is chosen from one or more of: a threonine to methionine substitution at position 311 (a T311M); a serine to leucine substitution at position 341 (a S341L); an alanine to glutamate substitution at position 350 (a A350E); an arginine to histidine substitution at position 394 (a R394H); a glutamine substitution at position 414, e.g., an insertion to a stop codon (a Q414*); a serine to proline substitution at position 433 (a S433P); an arginine to tryptophan substitution at position 503 (a R503W); a tyrosine to asparagine substitution at position 537 (a Y537N); a tyrosine to cysteine substitution at position 537 (a Y537C); or an aspartate to glycine substitution at position 538 (a D538G), of SEQ ID NO:2. In other embodiment, the mutation is an insertion mutation, e.g., an amino acid insertion between amino acids G344 and L345 of SEQ ID NO:2, e.g., an insertion of a C amino acid.

In other embodiments, the mutant ESR1 polypeptide includes a ligand binding domain or a fragment thereof, a hinge region or a fragment thereof, a DNA binding domain or fragment thereof, and an AF-1 domain or fragment thereof. In another embodiment, the mutant ESR1 polypeptide includes the amino acid sequence of amino acids 1-593 of SEQ ID NO:4 or a fragment thereof, or a sequence substantially identical thereto. For example, the mutant ESR1 polypeptide can include a ligand binding domain of ESR1 that includes amino acids 312-544 of SEQ ID NO:4 or a fragment thereof. In other embodiments, the mutant ESR1 polypeptide includes the amino acid sequence of amino acids 185-593 of SEQ ID NO:4 or a fragment thereof, or a sequence substantially identical thereto.

In yet other embodiments, the mutant ESR1 polypeptide is encoded by a nucleic acid molecule described herein. In one embodiment, the mutant ESR1 polypeptide is encoded by nucleic acid having a non-frameshift deletion in exon 8 of ESR1, or a missense mutation as described herein. In other embodiments, the mutant ESR1 polypeptide is encoded by a nucleotide sequence in the region of 152,265,560-152,265,630 of chromosome 6. In another embodiment, the mutant ESR1 polypeptide includes an amino acid sequence encoded by a nucleotide sequence comprising a fusion junction created by a deletion in the ligand binding domain of ESR1 transcript, e.g., a nucleotide sequence that includes a portion of SEQ ID NO:3 (e.g., a nucleotide sequence within exons 1-12 of an ESR1 gene) (e.g., a portion of SEQ ID NO:3 comprising nucleotides 1021-1081, 1033-1071, or 1036-1060 of SEQ ID NO:3 (see FIG. 4B)). In other embodiment, the mutant ESR1 polypeptide is encoded by a nucleic acid that includes a nucleotide mutation chosen from one or more of: a C to T replacement at nucleotide 932; a C to T replacement at nucleotide 1022; a C to A replacement at nucleotide 1049; a G to A replacement at nucleotide 1181A; a C to T replacement at nucleotide 1240; a T to C replacement at nucleotide 1297; a T to A replacement at nucleotide 1609; an A to G replacement at nucleotide 1610; or an A to G replacement at nucleotide 1613, of SEQ ID NO:1. In one embodiment, the mutation is an A to G replacement at nucleotide 1613, of SEQ ID NO:1. In yet other embodiments, the mutant ESR1 polypeptide is encoded by a nucleic acid that includes an insertion of nucleotides GCT between nucleotides 1032 and 1033 of SEQ ID NO:1.

In an embodiment, the mutant ESR1 polypeptide comprises sufficient ESR1 sequence such that it has ligand binding activity, e.g., has elevated or constitutive activity. In one embodiment, the mutant ESR1 polypeptide binds estrogen with a higher affinity, as compared with wildtype ESR1 e.g., in a cell of a cancer referred to herein. In an embodiment, the mutant ESR1 polypeptide comprises at least 1, 2, 3, 4, 5, 6, 7, 8 9, 10, 11 or 12 exons, e.g., exons 5b, 6, 7, 8, 9, 10, 11 and 12, of a mutant ESR1 transcript. In one embodiment, the mutant ESR1 polypeptide, or a functional fragment thereof, includes a ligand binding domain or a functional fragment thereof, a hinge domain or a functional fragment thereof, a DNA binding domain or a functional fragment thereof and an AF-1 domain or a functional fragment thereof. In a related aspect, the invention features a mutant ESR1 polypeptide or fragments operatively linked to heterologous polypeptides to form fusion proteins.

In another embodiment, the mutant ESR1 polypeptide or fragment thereof is a peptide, e.g., an immunogenic peptide or protein that contains a fusion junction created by a deletion mutant, or a missense mutation described herein. Such immunogenic peptides or proteins can be used to raise antibodies specific to the mutant protein. In other embodiments, such immunogenic peptides or proteins can be used for vaccine preparation. The vaccine preparation can include other components, e.g., an adjuvant.

In another aspect, the invention features antibody molecules that bind to a mutant ESR1 polypeptide or fragment described herein. In embodiments the antibody can distinguish wild-type ESR1 from mutant ESR1.

In one aspect, the invention features a polypeptide comprising a mutation identified in Table 1 or Table 2 or Table 3.

Methods for Detecting Mutant ESR1

In another aspect, the invention features a method of determining the presence of a mutant ESR1, e.g., a mutant ESR1 as described herein. In one embodiment, the mutant ESR1 is detected in a nucleic acid molecule or a polypeptide. The method includes detecting whether a mutant ESR1 nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In one embodiment, the sample is, or has been, classified as non-malignant using other diagnostic techniques, e.g., immunohistochemistry.

In one embodiment, the sample is, or has been, classified as malignant using other diagnostic techniques, e.g., immunohistochemistry. In one embodiment, the sample is ER-positive.

In one embodiment, the sample is acquired from a subject (e.g., a subject, e.g., a patient, having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In embodiments, the tumor is from a cancer described herein, e.g., is chosen from a breast cancer, a prostate cancer, an ovarian cancer, an endometrial cancer or a colon cancer or a combination thereof.

In one embodiment, the ESR1 is detected in a patient whose cancer has recurred, such as after a period of remission. In another embodiment, the mutant ESR1 is detected in a metastasis. For example, a breast cancer patient receiving, or having previously received, an anti-cancer treatment such as a SERM, e.g., tamoxifen, can have a cancer, e.g. a breast cancer, that recurs or that has metastasized (e.g., an ER+ breast cancer patient with late stage, progressive metastatic cancer). The mutant ESR1 can be detected in a circulating tumor cell, or in a metastasis, such as in a metastasis from a tissue other than the tissue of the primary tumor (e.g., in a tissue other than breast tissue, such as from blood, bone, lung or liver tissue). The patient can continue to be administered the SERM, or can receive a lower dose of a SERM after a mutation in the ligand binding domain of ESR1 is detected. Alternatively, the patient can be administered an anti-cancer agent that is not a SERM. For example, in one embodiment, the patient is a post-menopausal female who is not administered a SERM, and who is administered an aromatase inhibitor, a SERD, a fulvestrant, or other estrogen receptor modulator described herein.

In one embodiment, the subject is at risk of having, or has a cancer (e.g., a patient with a cancer described herein).

In other embodiments, the mutant ESR1 is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the mutant ESR1 nucleic acid molecule. The method can, optionally, include enriching a sample for the gene or gene product.

In a related aspect, a method for determining the presence of a mutant ESR1 nucleic acid molecule is provided. The method includes: acquiring a sequence for a position in a nucleic acid molecule, e.g., by sequencing at least one nucleotide of the nucleic acid molecule (e.g., sequencing at least one nucleotide in the nucleic acid molecule that comprises the mutant ESR1), thereby determining that the mutant ESR1 is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a tumor), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a tumor or cancer sample, from a subject (e.g., a patient). In certain embodiments, the cancer is chosen from a breast cancer, prostate cancer, ovarian cancer, endometrial cancer, or colon cancer.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes a mutant ESR1 described herein. In one embodiment the invention features a method of analyzing a metastasis, e.g., in a tissue separate from the site of the primary tumor.

In yet other embodiments, a mutant ESR1 polypeptide is detected. The method includes: contacting a protein sample with a reagent which specifically binds to a mutant ESR1 polypeptide; and detecting the formation of a complex of the mutant ESR1 polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

In yet another embodiment, the level (e.g., expression level) or activity of the mutant ESR1 is evaluated. For example, the level (e.g., expression level) or activity of the mutant ESR1 (e.g., mRNA or polypeptide) is detected and (optionally) compared to a pre-determined value, e.g., a reference value (e.g., a control sample).

In yet another embodiment, the mutant ESR1 is detected prior to initiating, during, or after, a treatment in a subject, e.g., a treatment with an estrogen inhibitor, e.g., a SERM, an aromatase inhibitor, a SERD, or other estrogen receptor modulator disclosed herein. In one embodiment, the mutant ESR1 is detected at the time of diagnosis with a cancer. In other embodiments, the mutant ESR1 is detected at a pre-determined interval, e.g., a first point in time and at least at a subsequent point in time.

In certain embodiments, responsive to a determination of the presence of the mutant ESR1, the method further includes one or more of:

(1) stratifying a patient population (e.g., assigning a subject, e.g., a patient, to a group or class);

(2) identifying or selecting the subject as likely or unlikely to respond to a treatment, e.g., a SERM inhibitor treatment as described herein;

(3) selecting a treatment option, e.g., administering or not administering a preselected therapeutic agent, e.g., a SERM or an aromatase inhibitor as described herein; or (4) prognosticating the time course of the disease in the subject (e.g., evaluating the likelihood of increased or decreased patient survival).

In certain embodiments, the estrogen inhibitor is an aromatase inhibitor or a SERM. In one embodiment, the aromatase inhibitor is chosen from aminoglutethimide, testolactone (Teslac®), anastrozole (Arimidex®), letrozole (Femara®), exemestane (Aromasin®), vorozole (Rivizor), formestane (Lentaron®), fadrozole (Afema); 4-hydroxyandrostenedione, 1,4,6-androstatrien-3, 17-dione (ATD), and 4-Androstene-3,6,17-trione ("6-OXO"). In other embodiments, a SERM is chosen from raloxifene (Evista®), EM652, GW7604, keoxifene, toremifene (Fareston®), tamoxifen (Nolvadex®), lasofoxifene, levormeloxifene, bazedoxifene, or arzoxifene. In another embodiment the anti-estrogen agent is the estrogen antagonist is fulvestrant (ICI 182, 780; Faslodex®). In other embodiment, the anti-estrogen agent is a SERD. In yet other embodiments, the anti-estrogen agent is described in, e.g., WO 2012/037411, WO 2012/037410, WO 2011/159769, WO 2011/156518 and US 2012/0071535.

In one embodiment, the mTOR pathway inhibitor is chosen from rapamycin, temsirolimus (TORISEL®), everolimus (RAD001, AFINITOR®), ridaforolimus, AP23573, AZD8055, BEZ235, BGT226, XL765, PF-4691502, GDC0980, SF1126, OSI-027, GSK1059615, KU-0063794, WYE-354, INK128, temsirolimus (CCI-779), Palomid 529 (P529), PF-04691502, or PKI-587.

In certain embodiments, responsive to the determination of the presence of the mutant ESR1, the subject is classified as a candidate to receive treatment with an anti-cancer agent that is not a SERM. For example, the subject is a post-menopausal female classified as a candidate to receive treatment with an aromatase inhibitor. In one embodiment, the subject is a pre-menopausal female classified as a candidate to receive treatment with an estrogen receptor blocking agent, or to receive an oophorectomy. In another embodiment, the subject is classified as a candidate to continue receiving treatment with the SERM, and optionally, to receive more frequent monitoring for worsening cancer symptoms, e.g., increased tumor size, metastasis, or appearance of the cancer in additional tissues.

In one embodiment, responsive to the determination of the presence of the mutant ESR1, the subject, e.g., a patient, can further be assigned to a particular class if a mutant ESR1 is identified in a sample of the patient. For example, a post-menopausal female patient identified as having a mutant ESR1 can be classified as a candidate to receive treatment with an aromatase inhibitor, e.g., an aromatase inhibitor, a SERD, an estrogen receptor modulator, or an mTOR pathway inhibitor, as described herein. In one embodiment, the subject, e.g., a patient, is assigned to a second class if the mutation is not present. For example, a patient who has a breast cancer that does not contain a mutant ESR1, may be determined to be a candidate to receive a SERM, or to continue receiving a SERM, such as tamoxifen, alone or in combination with other agents, e.g., an aromatase inhibitor, a SERD, an estrogen receptor modulator, or an mTOR pathway inhibitor.

In another embodiment, responsive to the determination of the presence of the mutant ESR1, the subject is identified as likely to respond to a treatment that comprises an aromatase inhibitor e.g., an aromatase inhibitor, a SERD, an estrogen receptor modulator, or an mTOR pathway inhibitor, as described herein. Typically, a subject identified as being likely to respond to the treatment is a post-menopausal female.

In yet another embodiment, responsive to the determination of the presence of the mutant ESR1, the method includes administering an aromatase inhibitor, a SERD, an estrogen receptor modulator, or an mTOR pathway inhibitor, as described herein, to the subject.

In one embodiment, a subject who is determined not to carry a mutant ESR1 is reevaluated at intervals, such as every month, every two months, every six months or every year, or more or less frequently, to monitor the patient for the development of a mutation in ESR1, e.g., in the ligand binding domain of ESR1. For example, if a patient is determined not to carry a mutant ESR1, then the patient can be determined to be a candidate for treatment with a SERM. If the patient is subsequently determined to have a mutant ESR1, administration of the SERM to the patient can be stopped, and the patient can be administered an anti-cancer agent that is not a SERM. For example, the patient may be a post-menopausal female who is administered an aromatase inhibitor or an mTOR pathway inhibitor, or the patient may be a pre-menopausal female who is administered an alternative estrogen receptor blocking agent or who is administered an oophorectomy. In some embodiments, the patient continues to receive treatment with the SERM (e.g., tamoxifen), and optionally, the patient can receive more frequent monitoring for a worsening of cancer symptoms.

In one embodiment, a patient determined to have a mutant ESR1, e.g., a mutation in the ligand binding domain of ESR1, is administered a lower dose of the SERM, and optionally, a second anti-cancer agent, such as an aromatase inhibitor, a SERD, an estrogen receptor modulator, or an mTOR pathway inhibitor.

Detection Reagents and Detection of Mutations

In another aspect, the invention features a detection reagent, e.g., a purified or isolated preparation thereof. Detection reagents can distinguish a nucleic acid, or protein sequence, having a mutation, e.g., a missense, or in-frame insertion or deletion, in ESR1, e.g., in the ligand binding or hinge region of ESR1, from a reference sequence. In an embodiment, the mutation is a mutation described herein, e.g., any of: a 6 nucleotide deletion of nucleotides 1046-1051 (TGGCAG) according to SEQ ID NO:1 or other deletion, e.g., an in-frame deletion, that includes one or more of nucleotides 1046-1051; a mutation at a position identified as mutated in Table 3, e.g., any of the mutations described in Table 3; or, an associated mutation. Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid derived from a tumor cell, e.g., an $ER^+$ tumor cell. Detection reagents, e.g., antibody-based detection reagents, can be used to identify mutations in a target protein, e.g., in a sample, e.g., a sample of protein derived from, or produced by, a tumor cell.

Nucleic Acid-based Detection Reagents

In an embodiment, the detection reagent comprises a nucleic acid molecule, e.g., a DNA, RNA or mixed DNA/RNA molecule, comprising sequence which is complementary with a nucleic acid sequence on a target nucleic acid (the sequence on the target nucleic acid that is bound by the detection reagent is referred to herein as the "detection reagent binding site" and the portion of the detection reagent that corresponds to the detection reagent binding site is referred to as the "target binding site"). In an embodiment the detection reagent binding site is disposed in relationship to the interrogation position such that binding (or in embodiments, lack of binding) of the detection reagent to the detection reagent binding site allows differentiation of mutant and reference sequences for a mutant described herein. The detection reagent can be modified, e.g., with a label or other moiety, e.g., a moiety that allows capture.

In an embodiment, the detection reagent comprises a nucleic acid molecule, e.g., a DNA, RNA or mixed DNA/RNA molecule, which, e.g., in its target binding site, includes the interrogation position and which can distinguish (e.g., by affinity of binding of the detection reagent to a target nucleic acid or the ability for a reaction, e.g., a ligation or extension reaction with the detection reagent) between a mutation, e.g., a mutation described herein, and a reference sequence. In embodiments, the interrogation position can correspond to a terminal, e.g., to a 3' or 5' terminal nucleotide, a nucleotide immediately adjacent to a 3' or 5' terminal nucleotide, or to another internal nucleotide, of the detection reagent or target binding site.

In embodiments, the difference in the affinity of the detection reagent for a target nucleic acid comprising the mutant and that for a target nucleic acid comprising the reference sequence allows determination of the presence or absence of the mutation (or reference) sequence. Typically such detection reagents, under assay conditions, will exhibit substantially higher levels of binding only to the mutant or only to the reference sequence, e.g., will exhibit substantial levels of binding only to the mutant or only to the reference sequence.

In embodiments, binding allows (or inhibits) a subsequent reaction, e.g., a subsequent reaction involving the detection reagent or the target nucleic acid. E.g., binding can allow ligation, or the addition of one or more nucleotides to a nucleic acid, e.g., the detection reagent, e.g., by DNA polymerase, which can be detected and used to distinguish mutant from reference. In embodiments, the interrogation position is located at the terminus, or sufficiently close to the terminus, of the detection reagent or its target binding site, such that hybridization, or a chemical reaction, e.g., the addition of one or more nucleotides to the detection reagent, e.g., by DNA polymerase, only occurs, or occurs at a substantially higher rate, when there is a perfect match between the detection reagent and the target nucleic acid at the interrogation position or at a nucleotide position within 1, 2, or 3 nucleotides of the interrogation position.

In an embodiment, the detection reagent comprises a nucleic acid, e.g., a DNA, RNA or mixed DNA/RNA molecule wherein the molecule, or its target binding site, is adjacent (or flanks), e.g., directly adjacent, to the interrogation position, and which can distinguish between a mutation, e.g., a mutation described herein, and a reference sequence, in a target nucleic acid.

In embodiments the detection reagent binding site is adjacent to the interrogation position, e.g., the 5' or 3' terminal nucleotide of the detection reagent, or its target binding site, is adjacent, e.g., between 0 (directly adjacent) and 1,000, 500, 400, 200, 100, 50, 10, 5, 4, 3, 2, or 1 nucleotides from the interrogation position. In embodiments, the outcome of a reaction will vary with the identity of the nucleotide at the interrogation position allowing one to distinguish between mutant and reference sequences. E.g., in the presence of a first nucleotide at the interrogation position a first reaction will be favored over a second reaction. E.g., in a ligation or primer extension reaction, the product will differ, e.g., in charge, sequence, size, or susceptibility to a further reaction (e.g., restriction cleavage) depending on the identity of the nucleotide at the interrogation position. In embodiments the detection reagent comprises paired molecules (e.g., forward and reverse primers), allowing for amplification, e.g., by PCR amplification, of a duplex containing the interrogation position. In such embodiments, the presence of the mutation can be determined by a difference in the property of the amplification product, e.g., size, sequence, charge, or susceptibility to a reaction, resulting from a sequence comprising the interrogation position and a corresponding sequence having a reference nucleotide at the interrogation positions. In embodiments, the presence or absence of a characteristic amplification product is indicative of the identity of the nucleotide at the interrogation site and thus allows detection of the mutation.

In embodiments the detection reagent, or its target binding site, is directly adjacent to the interrogation position, e.g., the 5' or 3'terminal nucleotide of the detection reagent is directly adjacent to the interrogation position. In embodiments, the identity of the nucleotide at the interrogation position will determine the nature of a reaction, e.g., a reaction involving the detection reagent, e.g., the modification of one end of the detection reagent. E.g., in the presence of a first nucleotide at the interrogation position a first reaction will be favored over a second reaction. By way of example, the presence of a first nucleotide at the interrogation position, e.g., a nucleotide associated with a mutation, can promote a first reaction, e.g., the addition of a complementary nucleotide to the detection reagent. By way of example, the presence of an A at the interrogation position will cause the incorporation of a T, having e.g., a first colorometric label, while the presence of a G and the interrogation position will cause the incorporation for a C, having, e.g., a second colorometric label. In an embodiment the presence of a first nucleotide at the nucleotide will result in ligation of the detection reagent to a second nucleic acid. E.g., a third nucleic acid can be hybridized to the target nucleic acid sufficiently close to the interrogation site that if the third nucleic acid has an exact match at the interrogation site it will be ligated to the detection reagent. Detection of the ligation product, or its absence, is indicative of the identity of the nucleotide at the interrogation site and thus allows detection of the mutation.

A variety of readouts can be employed. E.g., binding of the detection reagent to the mutant or reference sequence can be followed by a moiety, e.g., a label, associated with the detection reagent, e.g., a radioactive or enzymatic label. In embodiments the label comprises a quenching agent and a signaling agent and hybridization results in altering the distance between those two elements, e.g., increasing the distance and unquenching the signaling agent. In embodiments the detection reagent can include a moiety that allows separation from other components of a reaction mixture. In embodiments binding allows cleavage of the bound detection reagent, e.g., by an enzyme, e.g., by the nuclease activity of the DNA polymerase or by a restriction enzyme. The cleavage can be detected by the appearance or disappearance of a nucleic acid or by the separation of a quenching agent and a signaling agent associated with the detection reagent. In embodiments binding protects, or renders the target susceptible, to further chemical reaction, e.g., labeling or degradation, e.g., by restriction enzymes. In embodiments binding with the detection reagent allows capture separation or physical manipulation of the target nucleic acid to thereby allow for identification. In embodiments binding can result in a detectable localization of the detection reagent or target, e.g., binding could capture the target nucleic acid or displace a third nucleic acid. Binding can allow for determination of the presence of mutant or reference sequences with FISH, particularly in the case of rearrangements. Binding can allow for the extension or other size change in a component, e.g., the detection reagent, allowing distinction between mutant and reference sequences. Binding can allow for the production, e.g., by PCR, of an amplicon that distinguishes mutant from reference sequence.

In an embodiment the detection reagent, or the target binding site, is between 5 and 500, 5 and 300, 5 and 250, 5 and 200, 5 and 150, 5 and 100, 5 and 50, 5 and 25, 5 and 20, 5 and 15, or 5 and 10 nucleotides in length. In an embodiment the detection reagent, or the target binding site, is between 10 and 500, 10 and 300, 10 and 250, 10 and 200, 10 and 150, 10 and 100, 10 and 50, 10 and 25,10 and 20, or 10 and 15, nucleotides in length. In an embodiment the detection reagent, or the target binding site, is between 20 and 500, 20 and 300, 20 and 250, 20 and 200, 20 and 150, 20 and 100, 20 and 50, or 20 and 25 nucleotides in length. In an embodiment the detection reagent, or the target binding site, is sufficiently long to distinguish between mutant and reference sequences and is less than 100, 200, 300, 400, or 500 nucleotides in length.

Preparations of Mutant Nucleic Acid and Uses Thereof

In another aspect the invention features, purified or isolated preparations of a an ER+ tumor cell nucleic acid, e.g., an ESR1 nucleic acid, e.g., DNA, e.g., genomic DNA or cDNA, or RNA, containing an interrogation position described herein, useful for determining if a mutation disclosed herein is present. The nucleic acid includes the interrogation position, and typically additional ER1 sequence on one or both sides of the interrogation position. In addition the nucleic acid can contain heterologous sequences, e.g., adaptor or priming sequences, typically attached to one or both terminus of the nucleic acid. The nucleic acid also includes a label or other moiety, e.g., a moiety that allows separation or localization.

In embodiments, the nucleic acid is between 20 and 1,000, 30 and 900, 40 and 800, 50 and 700, 60 and 600, 70 and 500, 80 and 400, 90 and 300, or 100 and 200 nucleotides in length (with or without heterologous sequences). In embodiment the nucleic acid is between 40 and 1,000, 50 and 900, 60 and 800, 70 and 700, 80 and 600, 90 and 500, 100 and 400, 110 and 300, or 120 and 200 nucleotides in length (with or without heterologous sequences). In embodiment the nucleic acid is between 50 and 1,000, 50 and 900, 50 and 800, 50 and 700, 50 and 600, 50 and 500, 50 and 400, 50 and 300, or 50 and 200 nucleotides in length (with or without heterologous sequences). In embodiments the nucleic acid is of sufficient length to allow sequencing (e.g., by chemical sequencing or by determining a difference in $T_m$ between mutant and reference preparations) but is optionally less than 100, 200, 300, 400, or 500 nucleotides in length (with or without heterologous sequences).

Such preparations can be used to sequence nucleic acid from a sample, e.g., a tumor sample. In an embodiment the purified preparation is provided by in situ amplification of a nucleic acid provided on a substrate. In embodiments the purified preparation is spatially distinct from other nucleic acids, e.g., other amplified nucleic acids, on a substrate.

In an embodiment the purified or isolated preparation of nucleic acid is derived from a tumor of a type described herein, e.g., an $ER^+$ cancer, or a breast cancer, e.g., a breast cancer, e.g., a breast cancer that is one, two or all of $ER^+$, malignant, or resistant to treatment, e.g., treatment with a first or second line therapy, e.g., a SERM, e.g., a SERM described herein, e.g., tamoxifen. In an embodiment the ESR1 nucleic acid is derived from a breast cancer that is $ER^+$ and resistant to treatment, e.g., treatment with a first or second line therapy, e.g., a SERM, e.g., a SERM described herein, e.g., tamoxifen.

Such preparations can be used to determine if a sample comprises mutant sequence.

In another aspect, the invention features, a method of determining the sequence of an interrogation position for a mutation described herein, comprising:

providing a purified or isolated preparations of an $ER^+$ tumor cell nucleic acid or ESR1 nucleic acid, e.g., DNA, e.g., genomic DNA or cDNA, or RNA, containing an interrogation position described herein, sequencing, by a method that breaks or forms a chemical bond, e.g., a covalent or non-covalent chemical bond, e.g., in a detection reagent or a target sequence, the nucleic acid so as to determine the identity of the nucleotide at an interrogation position. The method allows determining if a mutation described herein is present.

In an embodiment, sequencing comprises contacting the ESR1 nucleic acid with a detection reagent described herein.

In an embodiment, sequencing comprises determining a physical property, e.g., stability of a duplex form of the ESR1 nucleic acid, e.g., $T_m$, that can distinguish mutant from reference sequence.

In an embodiment, the ESR1 nucleic acid is derived from a tumor of a type described herein, e.g., a breast cancer, e.g., a breast cancer, e.g., a breast cancer that is one, two or all of $ER^+$, malignant, or resistant to treatment, e.g., treatment with a first or second line therapy, e.g., a SERM, e.g., a SERM described herein, e.g., tamoxifen. In an embodiment the ESR1 nucleic acid is derived from an $ER^+$ cancer, e.g., a breast cancer that is $ER^+$ and resistant to treatment, e.g., treatment with a first or second line therapy, e.g., a SERM, e.g., a SERM described herein, e.g., tamoxifen.

Reaction Mixtures and Devices

In another aspect, the invention features, purified or isolated preparations of a ESR1 nucleic acid, e.g., DNA, e.g., genomic DNA or cDNA, or RNA, containing an interrogation position described herein, useful for determining if a mutation disclosed herein is present, disposed in sequencing device, or a sample holder for use in such a device. In an embodiment the ESR1 nucleic acid is derived from a tumor of a type described herein, e.g., a breast cancer, e.g., a breast cancer that is one, two or all of $ER^+$, malignant, or resistant to treatment, e.g., treatment with a first or second line therapy, e.g., a SERM, e.g., a SERM described herein, e.g., tamoxifen. In an embodiment the ESR1 nucleic acid is derived from an $ER^+$ cancer, e.g., a breast cancer that is $ER^+$ and resistant to treatment, e.g., treatment with a first or second line therapy, e.g., a SERM, e.g., a SERM described herein, e.g., tamoxifen.

In another aspect, the invention features, purified or isolated preparations of a ESR1 nucleic acid, e.g., DNA, e.g., genomic DNA or cDNA, or RNA, containing an interrogation position described herein, useful for determining if a mutation disclosed herein is present, disposed in a device for determining a physical or chemical property, e.g., stability of a duplex, e.g., $T_m$ or a sample holder for use in such a device. In an embodiment the device is a calorimeter. In an embodiment the ESR1 nucleic acid is derived from a tumor of a type described herein, e.g., an $ER^+$ cancer or a breast cancer, e.g., a breast cancer that is one, two or all of $ER^+$, malignant, or resistant to treatment, e.g., treatment with a first or second line therapy, e.g., a SERM, e.g., a SERM described herein, e.g., tamoxifen. In an embodiment the ESR1 nucleic acid is derived from a breast cancer that is $ER^+$ and resistant to treatment, e.g., treatment with a first or second line therapy, e.g., a SERM, e.g., a SERM described herein, e.g., tamoxifen.

The detection reagents described herein can be used to determine if a mutation described herein is present in a sample. In embodiments the sample comprises a nucleic acid that is derived from a tumor cell. The tumor cell can be from a tumor sample, e.g., a biopsy taken from the tumor, or from circulating tumor cells, e.g., from peripheral blood. In an embodiment the ESR1 nucleic acid is derived from a tumor of a type described herein, e.g., an $ER^+$ cancer or a breast cancer, e.g., a breast cancer that is one, two or all of $ER^+$, malignant, or resistant to treatment, e.g., treatment with a first or second line therapy, e.g., a SERM, e.g., a SERM described herein, e.g., tamoxifen. In an embodiment the ESR1 nucleic acid is derived from a breast cancer that is $ER^+$ and resistant to treatment, e.g., treatment with a first or second line therapy, e.g., a SERM, e.g., a SERM described herein, e.g., tamoxifen.

Accordingly, in one aspect, the invention features a method of making a reaction mixture comprising:

combining a detection reagent, or purified or isolated preparation thereof, described herein with a target nucleic acid derived from a tumor cell which comprises a sequence having an interrogation position for a mutation described herein.

In another aspect, the invention features, a reaction mixture comprising:

a detection reagent, or purified or isolated preparation thereof, described herein; and a target nucleic acid derived from a tumor cell which comprises a sequence having an interrogation position for a mutation described herein.

In an embodiment of the reaction mixture, or the method of making the reaction mixture:

the detection reagent comprises a nucleic acid, e.g., a DNA, RNA or mixed DNA/RNA, molecule which is complementary with a nucleic acid sequence on a target nucleic acid (the detection reagent binding site) wherein the detection reagent binding site is disposed in relationship to the interrogation position such that binding of the detection reagent to the detection reagent binding site allows differentiation of mutant and reference sequences for a mutant described herein.

In an embodiment of the reaction mixture, or the method of making the reaction mixture:

the tumor is a tumor described herein, e.g., an ER+ cancer or a breast cancer, e.g., a breast cancer that is one, two or all of ER+, malignant, or resistant to treatment, e.g., treatment with a first or second line therapy, e.g., a SERM, e.g., a SERM described herein, e.g., tamoxifen. In an embodiment the ESR1 nucleic acid is derived from a breast cancer that is ER+ and resistant to treatment, e.g., treatment with a first or second line therapy, e.g., a SERM, e.g., a SERM described herein, e.g., tamoxifen.

In an embodiment of the reaction mixture, or the method of making the reaction mixture: the mutation is a mutation described herein, including: a 6 nucleotide deletion of nucleotides 1046-1051 (TGGCAG) according to SEQ ID NO:1 or other deletion, e.g., an in-frame deletion, that includes one or more of nucleotides 1046-1051; a mutation at a position identified as mutated in Table 3, e.g., any of the mutations described in Table 3; or, an associated mutation.

In an embodiment of the reaction mixture, or the method of making the reaction mixture: the mutation is at position 537 or 538 of the amino acid sequence of SEQ ID NO:2 (FIGS. 2A-2B).

In an embodiment of the reaction mixture, or the method of making the reaction mixture the mutation is selected from:
  a missense mutation at amino acid 537 of SEQ ID NO:2;
  a missense mutation at nucleotide 1610 of SEQ ID NO:
  a tyrosine to asparagine substitution at position 537 (a Y537N);
  a tyrosine to cysteine substitution at position 537 (a Y537C);
  a T to A replacement at nucleotide 1609; or
  an A to G replacement at nucleotide 1610.

In an embodiment of the reaction mixture, or the method of making the reaction mixture: the mutation is selected from:
  a missense mutation at amino acid 538 of SEQ ID NO:2;
  a missense mutation at nucleotide 1613 of SEQ ID NO:1;
  an aspartate to glycine substitution at position 538 (a D538G), of SEQ ID NO:2; or
  an A to G replacement at nucleotide 1613, of SEQ ID NO:1.

A mutation described herein, can be distinguished from a reference, e.g., a non-mutant or wildtype sequence, by reaction with an enzyme that reacts differentially with the mutation and the reference. E.g., they can be distinguished by cleavage with a restriction enzyme that has differing activity for the mutant and reference sequences. E.g., the invention includes a method of contacting a nucleic acid comprising a mutation described herein with a such an enzyme and determining if a product of that cleavage which can distinguish mutant form reference sequence is present.

In one aspect, the inventions provides, a purified preparation of a restriction enzyme cleavage product which can distinguish between mutant and reference sequence, wherein one end of the cleavage product is defined by an enzyme that cleaves differentially between mutant and reference sequence. In an embodiment the cleavage product includes the interrogation position.

Protein-Based Detection Reagents, Methods, Reaction Mixtures and Devices

A mutant protein described herein can be distinguished from a reference, e.g., a non-mutant or wildtype protein, by reaction with a reagent, e.g., a substrate, e.g., a substrate for phosphorylation or other ESR1 activity, or an antibody, that reacts differentially with the mutant and reference protein. In one aspect, the invention includes a method of contacting a sample comprising a mutant protein described herein with a such reagent and determining if the mutant protein is present in the sample.

In another embodiment, the invention features, an antibody that can distinguish a mutant protein described herein, e.g., a mutant protein corresponding to a mutation in Table 3 or an associated mutation from a reference, e.g., a non-mutant or wildtype protein.

Accordingly, in one aspect, the invention features a method of making a reaction mixture comprising:
  combining a detection reagent, or purified or isolated preparation thereof, e.g., a substrate, e.g., a substrate for phosphorylation or other activity, or an antibody, described herein with a target ESR1 protein derived from a tumor cell which comprises a sequence having an interrogation position for a mutation described herein.

In another aspect, the invention features, a reaction mixture comprising:
  a detection reagent, or purified or isolated preparation thereof, e.g., a substrate, e.g., a substrate for phosphorylation or other activity, or an antibody, described herein; and
  a target ESR1 protein derived from a tumor cell which comprises a sequence having an interrogation position for a mutation described herein.

In an embodiment of the reaction mixture, or the method of making the reaction mixture:
  the detection reagent comprises an antibody specific for a mutant ESR1 protien described herein.

In an embodiment of the reaction mixture, or the method of making the reaction mixture:
  the tumor is a tumor described herein, e.g., an ER+ cancer or a breast cancer, e.g., a breast cancer that is one, two or all of ER+, malignant, or resistant to treatment, e.g., treatment with a first or second line therapy, e.g., a SERM, e.g., a SERM described herein, e.g., tamoxifen.

In an embodiment of the reaction mixture, or the method of making the reaction mixture: the mutation is a mutation described herein, including: a 6 nucleotide deletion of nucleotides 1046-1051 (TGGCAG) according to SEQ ID NO:1 or other deletion, e.g., an in-frame deletion, that includes one or more of nucleotides 1046-1051; a mutation at a position identified as mutated in Table 3, e.g., any of the mutations described in Table 3; or, an associated mutation.

In an embodiment of the reaction mixture, or the method of making the reaction mixture: the mutation is at position 537 or 538 of the amino acid sequence of SEQ ID NO:2 (FIGS. 2A-2B).

In an embodiment of the reaction mixture, or the method of making the reaction mixture the mutation is selected from:
  a missense mutation at amino acid 537 of SEQ ID NO:2;
  a missense mutation at nucleotide 1610 of SEQ ID NO:
  a tyrosine to asparagine substitution at position 537 (a Y537N);
  a tyrosine to cysteine substitution at position 537 (a Y537C);
  a T to A replacement at nucleotide 1609; or
  an A to G replacement at nucleotide 1610.

In an embodiment of the reaction mixture, or the method of making the reaction mixture: the mutation is selected from:
  a missense mutation at amino acid 538 of SEQ ID NO:2;
  a missense mutation at nucleotide 1613 of SEQ ID NO:1;

an aspartate to glycine substitution at position 538 (a D538G), of SEQ ID NO:2; or an A to G replacement at nucleotide 1613, of SEQ ID NO:1.

Kits

In another aspect, the invention features a kit comprising a detection reagent described herein.

Method of Evaluating a Cancer or a Subject

In another aspect, the invention features a method of evaluating a subject (e.g., a patient), e.g., for risk of having or developing a cancer, e.g., a breast cancer, a colorectal cancer, a lung cancer, or prostate cancer. The method includes: acquiring information or knowledge of the presence of a mutant ESR1 in a subject (e.g., acquiring genotype information of the subject that identifies a mutant ESR1 as being present in the subject); acquiring a sequence for a nucleic acid molecule identified herein (e.g., a nucleic acid molecule that includes a mutant ESR1 sequence); or detecting the presence of a mutant ESR1 nucleic acid or polypeptide in the subject), wherein the presence of the mutant ESR1 is positively correlated with increased risk for, or having, a cancer associated with the mutant ESR1.

The method can further include the step(s) of identifying (e.g., evaluating, diagnosing, screening, and/or selecting) the subject as being positively correlated with increased risk for, or having, a cancer associated with the mutant ESR1. In one embodiment, the subject is identified or selected as likely or unlikely to respond to a treatment, e.g., a SERM or an aromatase inhibitor treatment as described herein.

The method can further include treating the subject with an anti-cancer agent, e.g., a SERM, an aromatase inhibitor, a SERD, an estrogen receptor modulator, or an mTOR pathway inhibitor, as described herein.

The method can further include acquiring, e.g., directly or indirectly, a sample from a patient and evaluating the sample for the presence of a mutant ESR1 as described herein.

In one embodiment, a subject having a cancer, e.g., a breast cancer, is evaluated for the presence of a mutant ESR1, such as a mutation in the ligand binding domain of ESR1. In one embodiment, the subject has an ER-positive cancer, e.g., an ER-positive breast cancer (detected by, e.g., IHC). A subject identified as not having a mutant ESR1 can be administered a SERM, and the patient can be monitored at regular intervals, e.g., monthly, or once every three, six, 8 or 12 months, or at shorter or longer intervals, for the presence of a mutant ESR1. If during the course of SERM therapy, the subject is found to carry an ESR1 mutation, the subject can stop receiving SERM therapy, or can be administered a decreased dose of the SERM therapy. If the subject is a post-menopausal female patient, the patient may begin treatment with an aromatase therapy. If the subject is a pre-menopausal female patient, the patient may begin treatment with an alternative estrogen receptor blocker, or may receive an oophorectomy. In one embodiment, the subject continues to receive the SERM therapy. A patient who carries a mutation in the ligand binding domain of ESR1, such as a mutation described herein, and who continues to receive the SERM therapy (at the same or at a decreased dosage), may undergo increased monitoring for a worsening in cancer symptoms. In one embodiment, the dose of SERM is decreased over time.

In certain embodiments, the subject is a patient or patient population that has participated in a clinical trial. In one embodiment, the subject has participated in a clinical trial for evaluating an estrogen inhibitor (e.g., a SERM or an aromatase inhibitor). In one embodiment, the estrogen inhibitor was not a SERM. In one embodiment, the clinical trial is discontinued or terminated. In one embodiment, the subject responded favorably to the clinical trial, e.g., experienced an improvement in at least one symptom of a cancer (e.g., decreased in tumor size, rate of tumor growth, increased survival). In other embodiments, the subject did not respond in a detectable way to the clinical trial. In one embodiment, the presence of a mutant ESR1, e.g., an ESR1 comprising a mutation in the ligand binding domain identifies the patient as being a candidate to receive treatment with an agent other than a SERM. In another embodiment, the presence of the mutant ESR1 identifies the patient as being a candidate to receive treatment with an aromatase inhibitor or fulvestrant, or an alternative estrogen receptor blocking agent.

In a related aspect, a method of evaluating a patient or a patient population is provided. The method includes: identifying, selecting, or obtaining information or knowledge that the patient or patient population has participated in a clinical trial;

acquiring information or knowledge of the presence of a mutant ESR1 in the patient or patient population (e.g., acquiring genotype information of the subject that identifies a mutant ESR1 as being present in the subject); acquiring a sequence for a nucleic acid molecule identified herein (e.g., a nucleic acid molecule that includes a mutant ESR1 sequence); or detecting the presence of a mutant ESR1 nucleic acid or polypeptide in the subject), wherein the presence of the mutant ESR1 identifies the patient or patient population as having an increased risk for, or having, a cancer associated with the mutant ESR1.

In certain embodiments, the subject is a patient or patient population that has participated in a clinical trial. In one embodiment, the subject has participated in a clinical trial for evaluating a SERM or an aromatase inhibitor. In one embodiment, the clinical trial is discontinued or terminated. In one embodiment, the subject responded favorably to the clinical trial, e.g., experience an improvement in at least one symptom of a cancer (e.g., decreased in tumor size, rate of tumor growth, increased survival). In other embodiments, the subject did not respond in a detectable way to the clinical trial.

In embodiments, the method further includes treating the subject with a SERM or an aromatase inhibitor, e.g., an aromatase inhibitor as described herein.

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of nucleotide values, the indication of presence or absence of a mutant ESR1 as described herein, or sequence. In one embodiment, a report is generated, such as in paper or electronic form, which identifies the presence or absence of an alteration described herein, and optionally includes an identifier for the patient from which the sequence was obtained. In one embodiment, the report is in web-based form.

The report can also include information on the role of a sequence, e.g., a mutant ESR1 as described herein, or wild-type sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample, from a subject, detecting a mutant ESR1 as described herein in the sample, and selecting a treatment based on the mutation identified. In one embodiment, a report is generated that annotates the selected treatment, or that lists, e.g., in order of preference, two or more treatment options based on the mutation identified. In another embodiment, the subject, e.g., a patient, is further administered the selected method of treatment.

In one embodiment, a report is generated to memorialize each time a patient is tested for an ESR1 mutation. For example, a patient who is determined not to have an ESR1 mutation can be administered a SERM to treat a cancer, such as a breast cancer. The patient can be reevaluated at intervals, such as every month, every two months, every six months or every year, or more or less frequently, to monitor the patient for the development of a mutation in ESR1, e.g., in the ligand binding domain of ESR1. If the patient is subsequently determined to have a mutant ESR1, administration of the SERM to the patient can be stopped, and the patient can be administered an anti-cancer agent that is not a SERM. In one embodiment, the patient is a post-menopausal female patient who administered an aromatase inhibitor or fulvestrant, or an mTOR pathway inhibitor. In another embodiment, the patient is a pre-menopausal female patient who is administered an alternative estrogen receptor blocker, or an oophorectomy. In yet another embodiment, the patient continues to receive treatment with the SERM, or receives a lower dose of the SERM, and optionally the patient is monitored more frequently for a worsening of cancer symptoms. The report can record at least the treatment history of the patient and the corresponding result of each test to assay for an ESR1 mutation in the patient.

Systems or Devices

In another aspect, the invention features a system or a device (e.g., a sequencing device) for producing a report, e.g., a genotype report. The system or device can include a component for containing a sample (e.g., a tumor nucleic acid or polypeptide); a detection component capable of identifying the presence or absence of a mutant ESR1 as described herein; and a means for outputting a report, e.g., a report as described herein.

In one embodiment, the component for containing a tumor sample is configured in a way to contain or hold the sample, e.g., a tumor nucleic acid or polypeptide sample.

In another embodiment, the detection component produces and/or analyzes a signal according to the presence or absence of the mutant ESR1 in the sample.

In another embodiment, the means for outputting a report provides a system for annotating the association of the detected mutant ESR1 to the sample. The report can include, e.g., the identification of nucleotide values, the indication of presence or absence of a mutant ESR1 as described herein, or sequence. In one embodiment, a report is generated, such as in paper or electronic form, which identifies the presence or absence of an alteration described herein, and optionally includes an identifier for the patient from which the sequence was obtained.

The report can also include information on the role of a sequence, e.g., a mutant ESR1 as described herein, or wild-type sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report.

Methods of Reducing a Mutant ESR1 Activity

In another aspect, the invention features a method of reducing an activity of a mutant ESR1. The method includes administering an estrogen inhibitor, such as a SERM, aromatase or fulvestrant. In one embodiment, the estrogen inhibitor is not a SERM.

An "estrogen inhibitor" as used herein is any molecule that interferes with the estrogen signaling pathway, including SERMs and estrogen mimetics, which compete for binding with estrogen in the ligand binding domain of ESR1, and aromatase inhibitors, which interfere with the production of estrogen. An estrogen inhibitor can be an estrogen mimetic, which can interact with estrogen receptor to have a pro-estrogenic (estrogenic) or an anti-estrogenic effect. A pro-estrogenic, or estrogenic, response exaggerates or enhances the effect of an estrogen, such as by increasing transcription of gene under control of an estrogen response element. An anti-estrogenic response inhibits an estrogen-dependent activity, e.g., transcription of a gene under control of an estrogen response element is decreased in response to a molecule that has an anti-estrogenic effect.

An estrogen inhibitor can be a small molecule compound (e.g., a hormone, such as synthetic hormone), a nucleic acid (e.g., antisense, siRNA, aptamer, ribozymes, microRNA), or a protein, such as an antibody molecule (e.g., a full antibody or antigen binding fragment thereof that binds to mutant ESR1). The candidate agent can be obtained from a library (e.g., a commercial library of estrogen inhibitors, such as SERMs or aromatase inhibitors) or can be rationally designed (e.g., based on the ligand binding domain).

In one embodiment, the estrogen inhibitor is administered based on a determination that a mutant ESR1 is present in a subject, e.g., based on its presence in a subject's sample. Thus, treatment can be combined with a mutant ESR1 detection or evaluation method, e.g., as described herein, or administered in response to a determination made by a mutant ESR1 detection or evaluation method, e.g., as described herein. In certain embodiments, the estrogen inhibitor is administered responsive to acquiring knowledge or information of the presence of the mutant ESR1 in a subject. In one embodiment, the estrogen inhibitor is administered responsive to acquiring knowledge or information on the subject's genotype, e.g., acquiring knowledge or information that the patient's genotype has a mutation in the ESR1 gene. In other embodiments, the estrogen inhibitor is administered responsive to receiving a communication (e.g., a report) of the presence of the mutant ESR1 in a subject (e.g., a subject's sample). In yet other embodiments, the estrogen inhibitor is administered responsive to information obtained from a collaboration with another party that identifies the presence of the mutant ESR1 in a subject (e.g., a subject's sample). In other embodiments, the estrogen inhibitor is administered responsive to a determination that the mutant ESR1 is present in a subject. In one embodiment, the determination of the presence of the mutant ESR1 is carried out using one or more of the methods, e.g., the sequencing methods, described herein. In other embodiments, the determination of the presence of the mutant ESR1 includes receiving information on the subject's mutant ESR1 genotype, e.g., from another party or source.

The methods can, optionally, further include the step(s) of identifying (e.g., evaluating, diagnosing, screening, and/or selecting) a subject at risk of having, or having, a mutant ESR1. In one embodiment, the method further includes one or more of: acquiring knowledge or information of the presence of the mutant ESR1 in a subject (e.g., a subject's sample); acquiring knowledge or information on the subject's genotype, e.g., acquiring knowledge or information that the patient's genotype has a mutant ESR1; receiving a communication (e.g., a report) of the presence of the mutant ESR1 in a subject (e.g., a subject's sample); or collaborating with another party that identifies the presence of the mutant ESR1 in a subject.

In one embodiment, the subject treated has a mutant ESR1; e.g., the subject has a tumor or cancer harboring a mutant ESR1, such as a mutation in the ligand binding domain. In other embodiments, the subject has been previously identified as having a mutant ESR1.

In one embodiment, a SERM causes an estrogenic effect on the mutant ESR. In another embodiment, the subject is administered an anti-cancer agent that is not a SERM. For example, the subject is a post-menopausal female patient administered an aromatase inhibitor or fulvestrant. In another embodiment, the aromatase inhibitor or fulvestrant is administered responsive to the determination of the presence of the mutant ESR1 in a tumor sample from the subject.

In one embodiment, the subject was previously tested for the presence of a mutant ESR1 and a mutation in the ligand binding domain of ESR1 was not detected. The subject was further administered a SERM based on the knowledge that a mutation in the ligand binding domain of ESR1 was not detected. In one embodiment, the subject was further tested at intervals (e.g., monthly, or every 3, 4, 6 months, or every year, or more or less frequently) for the presence of a mutant ESR1, and where a mutation in the ligand binding domain of ESR1 was not detected, the subject continued treatment with a SERM based on the knowledge that a mutation in the ligand binding domain of ESR1 was not detected. In one embodiment, the subject was further tested at intervals for the presence of a mutant ESR1, and where a mutation in the ligand binding domain of ESR1 was detected, the subject stopped treatment with the SERM based on the knowledge that a mutation in the ligand binding domain of ESR1 was detected. In another embodiment, the subject further began treatment with an anti-cancer agent that was not a SERM. For example, in one embodiment, the subject was a post-menopausal female patient, and the patient began treatment with an aromatase inhibitor or fulvestrant. In another embodiment, the subject was a pre-menopausal female patient, and the patient was administered an alternative estrogen receptor blocker or an oophorectomy. In another embodiment, the subject maintained treatment with the SERM, or was administered a lower dose of the SERM based on the knowledge that a mutation in the ligand binding domain of ESR1 was detected, and in yet another embodiment, the patient was administered a combination of a lower dose of SERM and a second anti-cancer agent, such as an aromatase inhibitor or fulvestrant. In one embodiment, where the patient was continued to receive treatment with the SERM, the patient received increased monitoring for a worsening of cancer symptoms, such as described herein.

In yet other embodiments, the subject has been previously identified as being likely or unlikely to respond to treatment with a SERM, e.g., a subject that has previously participated in a clinical trial. In other embodiments, the subject has been previously identified as being likely or unlikely to respond to treatment with a SERM, based on the presence of the mutant ESR1.

Methods of reducing an activity of a mutant ESR1 include contacting the mutant ESR1, or a mutant ESR1-expressing cell, with an agent that inhibits an activity or expression of mutant ESR1, e.g., an agent that blocks the transcriptional activation activity of ESR1. In one embodiment, the contacting step can be effected in vitro, e.g., in a cell lysate or in a reconstituted system. Alternatively, the method can be performed on cells in culture, e.g., in vitro or ex vivo. In other embodiments, the method can be performed on mutant ESR1-expressing cells present in a subject, e.g., as part of an in vivo (e.g., therapeutic or prophylactic) protocol. In an embodiment, the method is practiced on an animal subject (e.g., an in vivo animal model). In certain embodiments, the mutant ESR1 is a nucleic acid molecule or a polypeptide as described herein.

In a related aspect, a method of inhibiting, reducing, or treating a hyperproliferative disorder, e.g., a cancer, in a subject is provided. The method includes administering to the subject a preselected therapeutic agent, e.g., an anti-cancer agent (e.g., estrogen inhibitor, such as an aromatase inhibitor or a SERM), as a single agent, or in combination, in an amount sufficient to reduce, inhibit or treat the activity or expression of mutant ESR1 (e.g., a mutant ESR1 described herein), thereby inhibiting, reducing, or treating the hyperproliferative disorder in the subject. "Treatment" as used herein includes, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

In one embodiment, the subject is a mammal, e.g., a human. In one embodiment, the subject has, or is at risk of having a cancer at any stage of disease. In other embodiments, the subject is a patient, e.g., a cancer patient.

In other embodiments, the subject treated is a cancer patient who has participated in a clinical trial. For example, the subject participated in a clinical trial that evaluated a SERM. In one embodiment, the cancer patient responded to the SERM evaluated.

In certain embodiments, the cancer is a solid tumor, a soft tissue tumor, or a metastatic lesion. In one embodiment, the cancer is chosen from a breast cancer, prostate cancer, ovarian cancer, endometrial cancer, colon cancer, or a combination thereof. In one embodiment, the cancer is a metastatic cancer.

In one embodiment, the anti-cancer agent is an estrogen inhibitor, such as an aromatase inhibitor. For example, the aromatase inhibitor is aminoglutethimide, testolactone (Teslac®), anastrozole (Arimidex®), letrozole (Femara®), exemestane (Aromasin®), vorozole (Rivizor), formestane (Lentaron®), fadrozole (Afema); 4-hydroxyandrostene-dione, 1,4,6-androstatrien-3,17-dione (ATD), and 4-Androstene-3,6,17-trione ("6-OXO").

In other embodiments, the anti-cancer agent is a mutant ESR1 antagonist that inhibits the expression of a nucleic acid encoding mutant ESR1. Examples of such mutant ESR1 antagonists include nucleic acid molecules, for example, antisense molecules, ribozymes, RNAi, triple helix molecules that hybridize to a nucleic acid encoding a mutant ESR1, or a transcription regulatory region, and blocks or reduces mRNA expression of mutant ESR1.

In other embodiments, the estrogen inhibitor is administered in combination with a second therapeutic agent or a different therapeutic modality, e.g., anti-cancer agents, and/or in combination with surgical and/or radiation procedures. For example, the second therapeutic agent can be a cytotoxic or a cytostatic agent. Exemplary cytotoxic agents include antimicrotubule agents, topoisomerase inhibitors, or taxanes, anti-metabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon α or γ, or immune cell growth factors such as GM-CSF.

Screening Methods

In another aspect, the invention features a method, or assay, for screening for agents that modulate, e.g., inhibit, the expression or activity of a mutant ESR1, e.g., a mutant ESR1 as described herein. The method includes contacting a mutant ESR1 nucleic acid or polypeptide, or a cell expressing a mutant ESR1 nucleic acid or polypeptide, with a candidate agent; and detecting a change in a parameter associated with a mutant ESR1, e.g., a change in the expression or an activity of the mutant ESR1. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the mutant ESR1 is detected, the candidate agent is identified as an inhibitor. In another embodiment, if an increase in expression or activity of the mutant ESR1 is detected, the candidate agent is identified as an activator. In certain embodiments, the mutant ESR1 is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a mutant ESR1 (e.g., a mammalian cell, a tumor cell or cell line, a recombinant cell). In yet other embodiments, the contacting step is effected in a cell in vivo (a mutant ESR1-expressing cell present in a subject, e.g., an animal subject (e.g., an in vivo animal model).

Exemplary parameters evaluated include one or more of:
(i) a change in binding activity, e.g., direct binding of the candidate agent to a mutant ESR1 polypeptide, e.g., an ESR1 carrying a mutation in the ligand binding domain; a binding competition between a known ligand (e.g., estrogen or an estrogen mimic) and the candidate agent to a mutant ESR1 polypeptide;
(ii) a change in transcriptional activation activity, e.g., expression levels of a reporter gene under control of an estrogen response element; or a change in DNA binding activity, such as binding at an estrogen response element; In certain embodiments, a change in DNA binding activity is detected by gel shift analysis, or by assaying expression from a reporter gene;
(iii) a change in an activity of a cell containing a mutant ESR1 (e.g., a tumor cell or a recombinant cell), e.g., a change in proliferation, morphology or tumorigenicity of the cell;
(iv) a change in a tumor present in an animal subject, e.g., size, appearance, proliferation, of the tumor; or
(v) a change in the level, e.g., expression level, of a mutant ESR1 polypeptide or nucleic acid molecule.

In one embodiment, a change in a cell free assay in the presence of a candidate agent is evaluated. For example, an activity of a mutant ESR1, or interaction of a mutant ESR1 with a ligand can be detected. In one embodiment, a mutant ESR1 polypeptide is contacted with a ligand, e.g., in solution, and a candidate agent is monitored for an ability to modulate, e.g., inhibit, an interaction, e.g., binding, between the mutant ESR1 polypeptide and the ligand (e.g., estrogen or an estrogen mimic).

In other embodiments, a change in an activity of a cell is detected in a cell in culture, e.g., a cell expressing a mutant ESR1 (e.g., a mammalian cell, a tumor cell or cell line, a recombinant cell). In one embodiment, the cell is a recombinant cell that is modified to express a mutant ESR1 nucleic acid, e.g., is a recombinant cell transfected with a mutant ESR1 nucleic acid. The transfected cell can show a change in response to the expressed mutant ESR1, e.g., increased proliferation, changes in morphology, increased tumorigenicity, and/or an acquired transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a mutant ESR1. In other embodiments, a change in binding activity or phosphorylation as described herein is detected.

In yet other embodiments, a change in a tumor present in an animal subject (e.g., an in vivo animal model) is detected. In one embodiment, the animal model is a tumor containing animal or a xenograft comprising cells expressing a mutant ESR1 (e.g., tumorigenic cells expressing a mutant ESR1). The candidate agent can be administered to the animal subject and a change in the tumor is detected. In one embodiment, the change in the tumor includes one or more of a change in tumor growth, tumor size, tumor burden, and survival. A decrease in one or more of tumor growth, tumor size, tumor burden, or an increased survival is indicative that the candidate agent is an inhibitor.

In other embodiments, a change in expression of a mutant ESR1 can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is a small molecule compound, e.g., an estrogen inhibitor, such as a SERM or an aromatase inhibitor, a nucleic acid (e.g., antisense, siRNA, aptamer, ribozymes, microRNA), an antibody molecule (e.g., a full antibody or antigen binding fragment thereof that binds to mutant ESR1). The candidate agent can be obtained from a library (e.g., a commercial library of estrogen inhibitors, such as SERMs or aromatase inhibitors) or rationally designed (e.g., based on the ligand binding domain).

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF DRAWINGS

FIGS. 2A and 2B are the cDNA (SEQ ID NO:1) and amino acid (SEQ ID NO:2) sequence alignment for wildtype ESR1 (RefSeq. NM_000125.3, Oct. 2, 2011). The deleted nucleotides at positions 1046-1051 and amino acids at positions 349-351 in the novel mutation are underlined and indicated in bold type in FIG. 2B. Underlined codons and amino acids indicate the sites of point mutations identified in Table 3.

FIG. 3 discloses SEQ ID NOs: 7-11, respectively, in order of appearance.

FIGS. 4A-4B are the cDNA (SEQ ID NO:3) and amino acid (SEQ ID NO:4) sequence alignments for the novel mutation in ESR1. The fusion junction created by the deletion, and the subsequent substation of H for the deleted amino acids LAD are indicated in bold type and by underlining in FIG. 4B. A bar ("|") marks the fusion junction.

DETAILED DESCRIPTION

Figure 1:
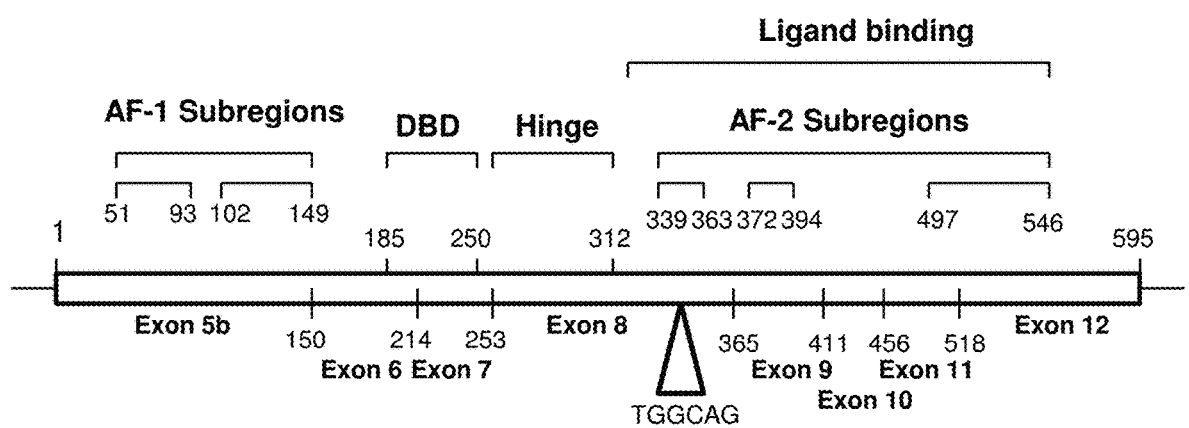
FIG. 1 is a schematic diagram of the structure of the ESR1 protein. The DNA-binding domain (DBD), hinge region and ligand binding domain are indicated. The Activation Function (AF) domains and exon boundaries are also indicated. Exons are numbered according to the numbering in RefSeq. NM_001122742 (Oct. 2, 2011).
Figure 3:
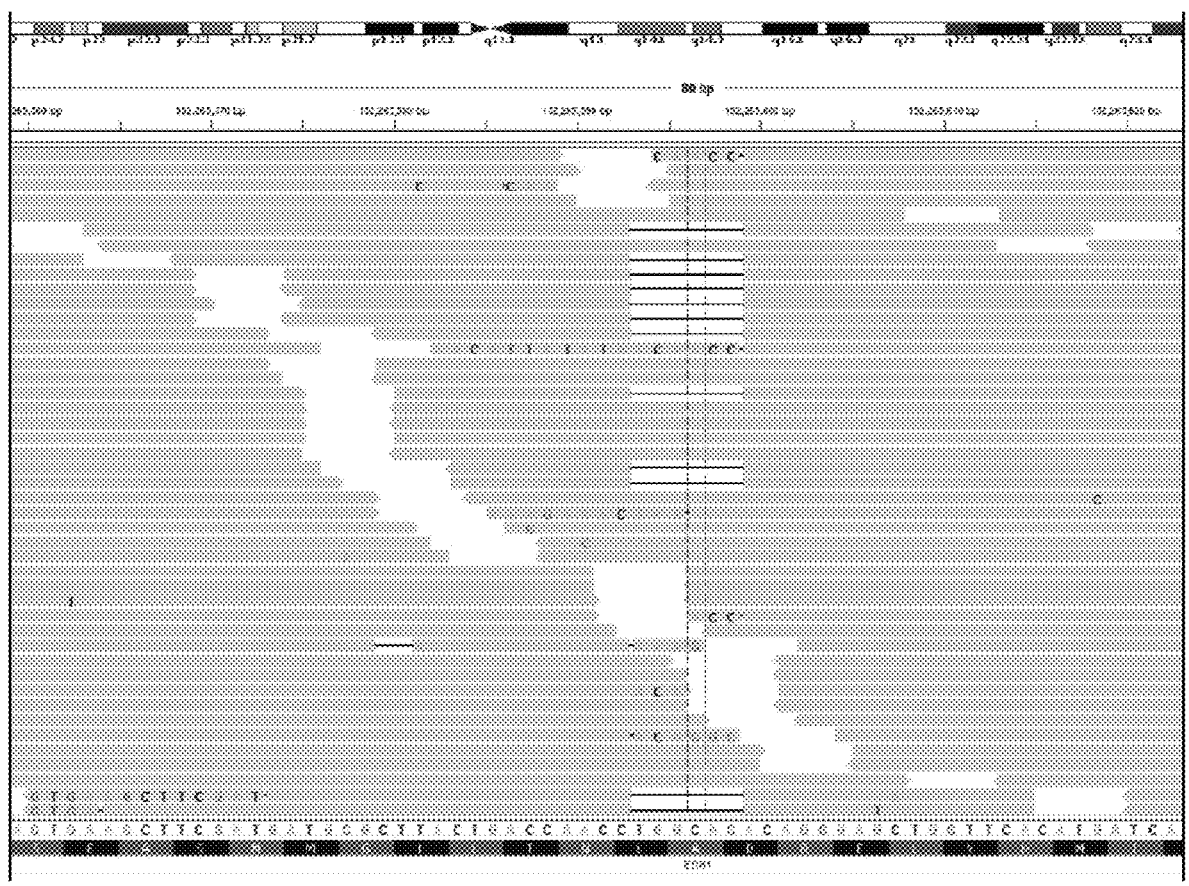
FIG. 3 is a snapshot of the sequencing reads illustrating that there is a 6 nucleotide deletion (TTGCAG) in the ESR1 gene, which causes replacement of amino acids LAD at positions 349-351 of the ESR1 protein, with H (See FIG. 2B).

The invention is based, at least in part, on the discovery of a novel mutation in the ligand binding domain of the estrogen receptor a gene (ESR1) and its association with cancer, e.g., breast cancer. In one embodiment, Applicants have discovered a novel deletion on chromosome 6 that results in deletion of 6 nucleotides and subsequently the substitution of a histidine for a leucine-adenine-aspartic acid deletion in the ligand binding domain of ESR1.

The ESR1 gene is associated with cancerous phenotypes, including breast cancer, ovarian cancer, endometrial cancer, prostate cancer and colon cancer, among others. For example, point mutations in ESR1 associated with breast cancer include the following alterations: S47T, N69K, and A86V, each individually in the AF-1 domain; L296P, and K303R in the region between the hinge and AF-2 domains, and E352V, M396V, 437stop, K531E, and Y537N in the hormone binding domain in AF-2 (Herynk and Fuqua, *Endocrine Reviews* 25:869-898, 2004). A breast cancer patient carrying the E352V mutation responded to adjuvant tamoxifen therapy (Id.). A naturally occurring mutation in the ligand binding domain was discovered in the tamoxifen-resistant MCF7/MT2 xenografted tumor line. The D351Y mutation was the primary form of ESR1 identified in this particular tumor, and while this mutation has not been identified in humans, research has indicated that this mutation, or a D351E mutation, causes many SERMs, including raloxifene, EM652, GW7604, keoxifene and tamoxifen, to have an estrogenic response. A mutation featured in the invention, e.g., a mutation in the ligand binding domain in the vicinity of D351 may therefore indicate that a SERM should not be administered for treatment of the cancer, and an aromatase inhibitor should be administered instead.

Other cancer-associated mutations identified in the ligand binding domain are believed to arise in response to treatment of a tumor with an estrogen mimetic, called a SERM ("Selective Estrogen Receptor Moldulator"), such as tamoxifen. For example, a D351Y or D351E mutation results in a receptor that exhibits an estrogenic response to therapy with SERMs including raloxifene (Evista®), EM652, GW7604, keoxifene, toremifene (Fareston®) and tamoxifen (Nolvadex®). Certain mutations in the ligand binding domain have been found to result in resistance of the tumor to estrogen mimetic therapy (e.g., tamoxifen resistance). Thus, the identification of the 6 nucleotide deletion described herein, or an overlapping mutation or a new mutation in the ligand binding domain of ESR1 can indicate the need to change therapies for a patient currently on a SERM therapy, or to alter the standard of care for the patient.

The identification of an ESR1 mutation as described herein may suggest that a SERM should not be administered to a subject or that a subject receiving, or continuing to receive treatment with the SERM should be monitored more frequently for worsening of cancer symptoms. In some embodiments, such as when the subject is a post-menopausal female patient, an anti-cancer agent that is not a SERM, e.g., an aromatase inhibitor, should be administered to the subject. When a subject is a pre-menopausal female patient, identification of an ESR1 mutation as described herein may suggest that the patient should receive an alternative estrogen receptor blocking agent or an oophorectomy.

In one embodiment, a subject, e.g., a cancer patient, is already receiving therapy with a SERM, e.g., tamoxifen, and the identification of a mutation in ESR1 may indicate that the patent should stop receiving treatment with a SERM, or should receive a lower dose of SERM, or that the dose should be tapered (lowered over time).

A patient with a six nucleotide deletion as described herein, or a non-frameshift mutation that similarly deletes one or more of Leu, Ala, or Asp, at amino acid positions 349, 350 or 351 of SEQ ID NO:4, respectively, can be determined to not be a candidate to receive a SERM for treatment of a cancer, or can be determined to be a candidate for treatment with a lower dose of a SERM. A subject receiving or continuing to receive treatment with the SERM can optionally be monitored more frequently for worsening of cancer symptoms. A post-menopausal patient with a six nucleotide deletion as described herein, or a non-frameshift mutation that similarly deletes one or more of Leu, Ala, or Asp, at amino acid positions of 349, 350 or 351 of SEQ ID NO:4, can be determined to be a candidate for treatment with an aromatase inhibitor.

Aromatase is the enzyme that synthesizes estrogen, and thus aromatase inhibitors are used to inhibit synthesis of estrogen in cancers that require estrogen for growth. Exemplary aromatase inhibitors include non-selective inhibitors, such as aminoglutethimide and testolactone (Teslac®); selective inhibitors, such as anastrozole (Arimidex®), letrozole (Femara®), exemestane (Aromasin®), vorozole (Rivizor), formestane (Lentaron®), and fadrozole (Afema); and the inhibitors 4-hydroxyandrostenedione, 1,4,6-androstatrien-3, 17-dione (ATD), 4-Androstene-3,6,17-trione ("6-OXO"). Aromatase inhibitors include irreversible steroidal inhibitors, such as exemestane and non-steroidal inhibitors, such as anastrozole.

In another embodiment, the identification of the 6 nucleotide deletion described herein, or a similar mutation, can indicate that the patient should stop administration with the current SERM therapy, and should be administered the antiestrogen fulvestrant (Faslodex®), which has not been associated with SERM-resistant mutations in the region of amino acid D351 of ESR1 (Herynk and Fuqua, *Endocrine Reviews* 25:869-898, 2004).

In another embodiment, the identification of the 6 nucleotide deletion described herein, or a similar mutation, can indicate that the patient should stop administration with the current SERM therapy, and should be administered the antiestrogen fulvestrant (Faslodex®) in combination with an aromatase therapy.

A pre-menopausal patient with a six nucleotide deletion as described herein, or a non-frameshift mutation that similarly deletes one or more of Leu, Ala, or Asp, at amino acid positions of 349, 350 or 351 of SEQ ID NO:4, can be determined to be a candidate for treatment with an oophorectomy (removal of the ovaries).

A novel mutation described herein is a 6 nucleotide deletion in the ligand-binding domain of the ESR1 gene. The six nucleotide deletion is the deletion of TGGCAG at nucleotides 1046-1051 of SEQ ID NO:1, which results in the deletion of amino acids LAD at position 349-351 of SEQ ID NO:1, and the insertion of histidine at postion 349 of SEQ ID NO:2.

ESR1 is also known as estrogen receptor 1, estrogen receptor, estrogen receptor a, estradiol receptor, Era, ER, ERα, ESR, ESRA, NR3A1, Nuclear receptor subfamily 3 group A member 1, RP1-130E4_1, and DKFZp686N23123. The mRNA sequence is provided at NM_000125.3.

ESR1 is a nuclear hormone receptor that binds estrogen. The main function of the estrogen receptor is as a DNA binding transcription factor that regulates gene expression. A schematic diagram of the ESR1 polypeptide is provided in FIG. 1. ESR1 contains two activation function domains (AF-1 and AF-2), a DNA binding domain, a hinge domain and a ligand binding domain. AF-1 domain is phosphorylated at Ser116 and Ser167, the DNA-binding domain is phosphorylated at Ser236, and the AF-2 domain is phosphorylated at Tyr537. The AF-1 domain is a ligand-independent transactivation domain, but the activation from AF-1 is weak and more selective compared to the activation provided by the hormone-inducible transactivating function of AF-2. The AF-2 domain contains the estrogen binding domain, as well as binding sites for coactivator and corepressor proteins (Benecke et al., *EMBO Reports* 1:151-157, 2000). Tamoxifen inhibits ESR1 activity by binding to the AF-2 domain (Id.). The DNA binding domain binds estrogen response elements in DNA. At least six different ESR1 mRNA isoforms are generated by alternative splicing and differ in their 5' untranslated regions as a consequence of alternative splicing of several upstream exons (1B-1F) to a common site 5' to the translation initiation codon and therefore result in the generation of a common ER-α protein that is 66 kDa in size (Flouriot et al., *EMBO J.* 19:4688-4700, 1998). A seventh isoform (hERα46) lacks the N-terminal 173 amino acids of the full-length hERα66 isoform, and inhibits hERα66 activity in a cell context where the transactivating function of AF-1 predominates over AF-2.

In one embodiment, a mutation in the ligand binding domain includes an in-frame deletion that eliminates the aspartic acid at position 351 of the wildtype ESR1 protein. The in-frame deletion can delete three, six, nine, or twelve nucleotides or more, that results in the deletion of one, two, three, four or five or more amino acids including the aspartic acid at position 351 of SEQ ID NO:2. The nucleotide deletion can include nucleotides between and including 1030-1068 of SEQ ID NO:1, e.g., between and including 1033-1065 of SEQ ID NO:1, e.g., between and including nucleotides 1036-1062 of SEQ ID NO:1. The deletion can result in the deletion of amino acids, and optionally, the insertion of new amino acids in the mutant ESR1 protein. For example, amino acids at positions from 344-356 of SEQ ID NO:2 can be deleted, e.g., from positions 346-354 of SEQ ID NO:2, e.g., from 349-351 of SEQ ID NO:2. The deletion can further result in an amino acid insertion or substitution, e.g., at a position between 344-356 of SEQ ID NO:2, e.g., from positions 346-354 of SEQ ID NO:2, e.g., from 349-351 of SEQ ID NO:2. In one embodiment, a histidine is inserted at position 349.

Estrogen and estrogen receptor a have been implicated in breast cancer, ovarian cancer, endometrial cancer, prostate cancer and colon cancer.

Accordingly, the invention provides, at least in part, isolated ESR1 nucleic acid molecules containing a mutation in the ligand binding domain, e.g., a 6 nucleotide deleting in the ligand binding domain as described herein, nucleic acid constructs, host cells containing the nucleic acid molecules; purified mutant ESR1 polypeptides comprising a mutation in the ligand binding domain, e.g., a deleting of the LAD at positions 349-351 of SEQ ID NO:2 and the insertion of histidine at position 349, and binding agents, e.g., antibodies and small molecule compounds that specifically bind the mutant protein. The invention also provides detection reagents (e.g., probes, primers, antibodies, kits); screening assays for identifying novel ESR1 inhibitors; as well as methods, assays and kits for evaluating, identifying, assessing and/or treating a subject having a cancer, e.g., a cancer having an ESR1 mutation disclosed herein. The compositions and methods identified herein can be used, for example, to identify new ESR1 inhibitors; to treat or prevent a cancer; as well as in methods or assays for evaluating a cancer (e.g., evaluating one or more of: cancer progression, cancer treatment response or resistance to cancer treatment; selecting a treatment option, stratifying a patient population, and/or more effectively monitoring, treating or preventing a cancer).

Other novel mutations are described in Table 1 and 2. The invention therefore also provides, at least in part, isolated nucleic acid molecules containing a mutation in Table 1 or Table 1, nucleic acid constructs, and host cells containing the nucleic acid molecules; purified mutant polypeptides comprising a mutation described in Table 1 or Table 2, and binding agents, e.g., antibodies and small molecule compounds that specifically bind the mutant proteins. The invention also provides detection reagents (e.g., probes, primers, antibodies, kits); screening assays for identifying novel inhibitors; as well as methods, assays and kits for evaluating, identifying, assessing and/or treating a subject having a cancer, e.g., a cancer having a mutation disclosed herein.

Certain terms are first defined. Additional terms are defined throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies an ESR1 mutation disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent, that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

As used herein, "estrogen receptor (ER) positive (+)" refers to a sample that contains an estrogen receptor, e.g., an ER detected by protein or nucleic acid levels. In one embodiment, a score of Estrogen Receptor positive (ER+) means that estrogen is causing a detectable response in a tumor, e.g., estrogen is causing a tumor to grow. In other embodiments, a score of Estrogen Receptor negative (ER−), means that estrogen is not causing a tumor to grow. ER+ status can reflect an increased level or activity of an ER relative to a reference sample (e.g., an ER− sample).

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a SERM or an aromatase inhibitor, alone or in combination, has an increased probability of responding to treatment with the SERM or the aromatase inhibitor alone or in combination, relative to a reference subject or group of subjects.

"Unlikely to" refers to a decreased probability that an event, item, object, thing or person will occur with respect to a reference. Thus, a subject that is unlikely to respond to treatment with a SERM, alone or in combination, has a decreased probability of responding to treatment with a SERM, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule are determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a mutation in the ESR1 gene. In certain embodiments, the reference or control nucleic acid sample is a wildtype or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Adjacent to the interrogation position," as used herein, means that a site sufficiently close such that a detection reagent complementary with the site can be used to distinguish between a mutation, e.g., a mutation described herein, and a reference sequence, e.g., a non-mutant or wild-type sequence, in a target nucleic acid. Directly adjacent, as used herein, is where 2 nucleotides have no intervening nucleotides between them.

"Associated mutation," as used herein, refers to a mutation within a preselected distance, in terms of nucleotide or primary amino acid sequence, from a definitional mutation, e.g., a mutant as described herein, e.g., a mutation in Table 3. In embodiments, the associated mutation is within n, wherein n is 2, 5, 10, 20, 30, 50, 100, or 200 nucleotides from the definitional mutation (n does not include the nucleotides defining the associated and definitional mutations). In embodiments the associated mutation is a missense mutation or an in-frame deletion or insertion.

"Interrogation position," as used herein, comprises at least one nucleotide (or, in the case of polypeptides, an amino acid residue) which corresponds to a nucleotide (or amino acid residue) that is mutated in a mutation of interest, e.g., a mutation being identified, or in a nucleic acid (or protein) being analyzed, e.g., sequenced, or recovered. By way of example the interrogation position in the T311M mutation described herein includes nucleotide position 932 and the interrogation position in the deletion at 1046-1051 includes one or more of nucleotide positions 1046-1051.

A "reference sequence," as used herein, e.g., as a comparator for a mutant sequence, is a sequence which has a different nucleotide or amino acid at an interrogation position than does the mutant(s) being analyzed. In an embodiment the reference sequence is wild-type for at least the interrogation position.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects of the invention are described in further detail below. Additional definitions are set out throughout the specification.

Isolated Nucleic Acid Molecules

One aspect of the invention pertains to isolated nucleic acid molecules that include an ESR1 mutation, including nucleic acids which encode an ESR1 polypeptide that contains a mutation in the ligand binding domain, or a portion of such an ESR1 polypeptide. The nucleic acid molecules include those nucleic acid molecules which reside in genomic regions identified herein. As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

Isolated nucleic acid molecules also include nucleic acid molecules sufficient for use as hybridization probes or primers to identify nucleic acid molecules that contain a mutation in an ESR1 gene, e.g., in the ligand binding domain of an ESR1 gene, e.g., nucleic acid molecules suitable for use as PCR primers for the amplification or mutation of nucleic acid molecules.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A nucleic acid molecule containing a mutation in the ESR1 gene can be isolated using standard molecular biology techniques and the sequence information in the database records described herein. Using all or a portion of such nucleic acid sequences, mutant ESR1 nucleic acid molecules can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule containing a mutation in the ESR1 gene, e.g., in the ligand binding domain of ESR1 can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In one embodiment, a nucleic acid molecule containing an ESR1 mutation comprises a nucleic acid molecule which has a nucleotide sequence complementary to the nucleotide sequence of a mutant ESR1 nucleic acid molecule or to the nucleotide sequence of a nucleic acid encoding a mutant ESR1 protein. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule containing a mutation in the ESR1 gene, e.g., in the ligand binding domain of the ESR1 gene, can comprise only a portion of a nucleic acid sequence, wherein the full length nucleic acid sequence encodes a mutant ESR1 polypeptide. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, at least about 15, at least about 25, at least about 50, at least about 75, at least about 100, at least about 125, at least about 150, at least about 175, at least about 200, at least about 250, at least about 300, at least about 350, at least about 400, at least about 500, at least about 600, at least about 700, at least about 800, at least about 900, at least about 1 kb, at least about 2 kb, at least about 3 kb, at least about 4 kb, at least about 5 kb, at least about 6 kb, at least about 7 kb, at least about 8 kb, at least about 9 kb, at least about 10 kb, at least about 15 kb, at least about 20 kb, at least about 25 kb, at least about 30 kb, at least about 35 kb, at least about 40 kb, at least about 45 kb, at least about 50 kb, at least about 60 kb, at least about 70 kb, at least about 80 kb, at least about 90 kb, at least about 100 kb, at least about 200 kb, at least about 300 kb, at least about 400 kb, at least about 500 kb, at least about 600 kb, at least about 700 kb, at least about 800 kb, at least about 900 kb, at least about 1 mb, at least about 2 mb, at least about 3 mb, at least about 4 mb, at least about 5 mb, at least about 6 mb, at least about 7 mb, at least about 8 mb, at least about 9 mb, at least about 10 mb or more consecutive nucleotides of a mutant ESR1 nucleic acid. The mutant nucleic acid can include a fusion junction created from the deletion of part of the ESR1 gene, e.g., part of the ligand binding domain of the ESR1 gene.

The invention further encompasses nucleic acid molecules that are substantially identical to the gene mutations and/or gene products described herein, e.g., a mutant ESR1 gene having a nucleotide sequence of SEQ ID NO:3 (or an amino acid sequence of SEQ ID NO: 4) such that they are at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater. In other embodiments, the invention further encompasses nucleic acid molecules that are substantially homologous to the ESR1 mutant gene and/or gene products described herein, such that they differ by only or at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 200, at least 300, at least 400, at least 500, at least 600 nucleotides or any range in between.

In another embodiment, an isolated mutant ESR1 nucleic acid molecule is at least 7, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 550, at least 650, at least 700, at least 800, at least 900, at least 1000, at least 1200, at least 1400, at least 1600, at least 1800, at least 2000, at least 2200, at least 2400, at least 2600, at least 2800, at least 3000, or more nucleotides in length and hybridizes under stringent conditions to a mutant ESR1 nucleic acid molecule or to a nucleic acid molecule encoding a protein corresponding to a marker of the invention.

As used herein, the term "hybridizes under stringent conditions" is intended to describe conditions for hybridization and washing under which nucleotide sequences at least 60%, at least 65%, at least 70%, at least 75%, at least 80%, or at least 85% identical to each other typically remain hybridized to each other. Such stringent conditions are known to those skilled in the art and can be found in sections 6.3.1-6.3.6 of Current Protocols in Molecular Biology, John Wiley & Sons, N.Y. (1989). Another, non-limiting example of stringent hybridization conditions are hybridization in 6× sodium chloride/sodium citrate (SSC) at about 45° C., followed by one or more washes in 0.2× SSC, 0.1% SDS at 50-65° C.

The invention also includes molecular beacon nucleic acid molecules having at least one region which is complementary to a mutant ESR1 nucleic acid molecule, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

Probes

The invention also provides isolated ESR1 mutant nucleic acid molecules useful as probes.

Probes based on the sequence of a mutant ESR1 nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor. Such probes can be used as part of a test kit for identifying cells or tissues which express the mutant ESR1 protein, such as by measuring levels of a nucleic acid molecule encoding the protein in a sample of cells from a subject, e.g., detecting mRNA levels or determining whether a gene encoding the protein has been mutated or deleted.

Probes featured in the invention include those that will specifically hybridize to a gene sequence described in the Example, e.g., an ESR1 gene having a six nucleotide deletion in the ligand binding domain. Typically these probes are 12 to 20, e.g., 17 to 20 nucleotides in length (longer for large insertions) and have the nucleotide sequence corresponding to the region of the mutations at their respective nucleotide locations on the gene sequence. Such molecules can be labeled according to any technique known in the art, such as with radiolabels, fluorescent labels, enzymatic labels, sequence tags, biotin, other ligands, etc. As used herein, a probe that "specifically hybridizes" to an ESR1 mutant gene sequence will hybridize under high stringency conditions.

A probe will typically contain one or more of the specific mutations described herein. Typically, a nucleic acid probe will encompass only one mutation. Such molecules may be labeled and can be used as allele-specific probes to detect the mutation of interest.

In one aspect, the invention features a probe or probe set that specifically hybridizes to a nucleic acid comprising a deletion in the ligand binding domain of ESR1.

Isolated pairs of allele specific oligonucleotide probes are also provided, where the first probe of the pair specifically hybridizes to the mutant allele, and the second probe of the pair specifically hybridizes to the wildtype allele. For example, in one exemplary probe pair, one probe will recognize the junction created by the deletion in the ligand binding domain of the ESR1 gene, and the other probe will recognize a sequence downstream or upstream of the deletion. These allele-specific probes are useful in detecting an ESR1 somatic mutation in a tumor sample, e.g., a breast tumor sample.

Primers

The invention also provides isolated nucleic acid molecules useful as primers.

The term "primer" as used herein refers to a sequence comprising two or more deoxyribonucleotides or ribonucleotides, e.g., more than three, and more than eight, or at least 20 nucleotides of a gene described in the Example, where the sequence corresponds to a sequence flanking one of the mutations or a wildtype sequence of a gene identified in the Example, e.g., an ESR1 gene. Primers may be used to initiate DNA synthesis via the PCR (polymerase chain reaction) or a sequencing method. Primers featured in the invention include the sequences recited and complementary sequences which would anneal to the opposite DNA strand of the sample target. Since both strands of DNA are complementary and mirror images of each other, the same segment of DNA will be amplified.

Primers can be used to sequence a nucleic acid, e.g., an isolated nucleic acid described herein, such as by an NGS method, or to amplify a gene described in the Example, such as by PCR. The primers can specifically hybridize, for example, to the ends of the exons or to the introns flanking the exons. The amplified segment can then be further analyzed for the presence of the mutation such as by a sequencing method, or by a size separation technique such as by electrophoresis on a gel. The primers are useful in directing amplification of a target polynucleotide prior to sequencing. In another aspect, the invention features a pair of oligonucleotide primers that amplify a region that contains or is adjacent to a fusion junction identified in FIG. 4B. Such primers are useful in directing amplification of a target region that includes a fusion junction identified in the FIG. 4B, e.g., prior to sequencing. The primer typically contains 12 to 20, or 17 to 20, or more nucleotides, although a primer may contain fewer nucleotides.

A primer is typically single stranded, e.g., for use in sequencing or amplification methods, but may be double stranded. If double stranded, the primer may first be treated to separate its strands before being used to prepare extension products. A primer must be sufficiently long to prime the synthesis of extension products in the presence of the inducing agent for polymerization. The exact length of primer will depend on many factors, including applications (e.g., amplification method), temperature, buffer, and nucleotide composition. A primer typically contains 12-20 or more nucleotides, although a primer may contain fewer nucleotides.

Primers are typically designed to be "substantially" complementary to each strand of a genomic locus to be amplified. Thus, the primers must be sufficiently complementary to specifically hybridize with their respective strands under conditions which allow the agent for polymerization to perform. In other words, the primers should have sufficient complementarity with the 5' and 3' sequences flanking the mutation to hybridize therewith and permit amplification of the genomic locus.

The term "substantially complementary to" or "substantially the sequence" refers to sequences that hybridize to the sequences provided under stringent conditions and/or sequences having sufficient homology with a sequence comprising a fusion junction identified in FIG. 4B, or the wildtype counterpart sequence, such that the allele specific oligonucleotides hybridize to the sequence. In one embodiment, a sequence is substantially complementary to a fusion junction created by a deletion event, e.g., to a fusion junction in SEQ ID NO:3. "Substantially the same" as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant gene sequence identified in the Example.

In one aspect, the invention features a primer or primer set for amplifying a nucleic acid comprising a deletion resulting in a ESR1 mutation.

Isolated pairs of allele specific oligonucleotide primer are also provided, where the first primer of the pair specifically hybridizes to the mutant allele, and the second primer of the pair specifically hybridizes to a sequence upstream or downstream of a mutation, or a fusion junction resulting from, e.g., an inversion, duplication, deletion, insertion or translocation. For example, in one exemplary primer pair, one probe will recognize an ESR1 mutation, such as by hybridizing to a sequence at the fusion junction resulting from the nucleotide(s) deletion, and the other primer will recognize a sequence upstream or downstream of the fusion junction. These allele-specific primers are useful for amplifying a mutant ESR1 sequence from a tumor sample, e.g., a breast tumor sample.

Primers can be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, (1981). One method for synthesizing oligonucleotides on a modified solid support is described in U.S. Pat. No. 4,458,066.

An oligonucleotide probe or primer that hybridizes to a mutant or wildtpe allele is said to be the complement of the allele. As used herein, a probe exhibits "complete complementarity" when every nucleotide of the probe is complementary to the corresponding nucleotide of the allele. Two polynucleotides are said to be "minimally complementary" if they can hybridize to one another with sufficient stability to permit them to remain annealed to one another under at least conventional "low-stringency" conditions. Similarly, the polynucleotides are said to be "complementary" if they can hybridize to one another with sufficient stability to permit them to remain annealed to one another under conventional "high-stringency" conditions. Conventional stringency conditions are known to those skilled in the art and can be found, for example in *Molecular Cloning: A Laboratory Manual,* 3rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of a probe to hybridize to an allele. Thus, in order for a polynucleotide to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0× SSC at 50° C. Such conditions are known to those skilled in the art and can be found, for example in *Current Protocols in Molecular Biology,* John Wiley & Sons, N.Y. (1989). Salt concentration and temperature in the wash step can be adjusted to alter hybridization stringency. For example, conditions may vary from low stringency of about 2.0× SSC at 40° C. to moderately stringent conditions of about 2.0× SSC at 50° C. to high stringency conditions of about 0.2× SSC at 50° C.

ESR1 Mutant Proteins and Antibodies

One aspect of the invention pertains to purified ESR1 mutant polypeptides, and biologically active portions thereof. In one embodiment, the native ESR1 mutant polypeptide can be isolated from cells or tissue sources by an appropriate purification scheme using standard protein purification techniques. In another embodiment, an ESR1 mutant polypeptide is produced by recombinant DNA techniques. Alternative to recombinant expression, a mutant ESR1 polypeptide can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein or biologically active portion thereof is recombinantly produced, it can be substantially free of culture medium, i.e., culture medium represents less than about 20%, less than about 10%, or less than about 5% of the volume of the protein preparation. When the protein is produced by chemical synthesis, it can be substantially free of chemical precursors or other chemicals, i.e., it is separated from chemical precursors or other chemicals which are involved in the synthesis of the protein. Accordingly such preparations of the protein have less than about 30%, less than about 20%, less than about 10%, less than about 5% (by dry weight) of chemical precursors or compounds other than the polypeptide of interest.

Biologically active portions of an ESR1 mutant polypeptide include polypeptides comprising amino acid sequences sufficiently identical to or derived from the amino acid sequence of the mutant ESR1 protein, which include fewer amino acids than the full length protein, and exhibit at least one activity of the corresponding full-length protein, e.g., a ligand-binding activity. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide.

In certain embodiments, the ESR1 mutant polypeptide has an amino acid sequence of a protein encoded by a nucleic acid molecule disclosed herein. Other useful proteins are substantially identical (e.g., at least 60, at least 65, at least 70, at least 75, at least 80, at least 85, at least 86, at least 87, at least 88, at least 89, at least 90, at least 91, at least 92, at least 93, at least 94, at least 95, at least 96, at least 97, at least 98, at least 99, at least 99.5% or greater) to one of these sequences and retain the functional activity of the protein of the corresponding full-length protein yet differ in amino acid sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. Another, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An isolated ESR1 mutant polypeptide, or a fragment thereof, can be used as an immunogen to generate antibodies using standard techniques for polyclonal and monoclonal antibody preparation. The full-length ESR1 mutant polypeptide can be used or, alternatively, the invention provides antigenic peptide fragments for use as immunogens. The antigenic peptide of a protein of the invention comprises at least 8 (or at least 10, at least 15, at least 20, or at least 30 or more) amino acid residues of the amino acid sequence of one of the polypeptides of the invention, and encompasses an epitope of the protein such that an antibody raised against the peptide forms a specific immune complex with a marker of the invention to which the protein corresponds. Exemplary epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect of the invention pertains to antibodies directed against a mutant ESR1 polypeptide. In one embodiment, the antibody molecule specifically binds to the junction created by the deletion in the ligand binding domain, e.g., specifically binds to an epitope formed as a result of the nucleotide deletion. In some embodiments the antibody can distinguish wildtype ESR1 from mutant ESR1.

The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition," as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. Antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions can be made using standard recombinant DNA techniques. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

Completely human antibodies can be produced using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

An antibody directed against a mutant ESR1 polypeptide (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g., in a tumor cell-containing body fluid) as part of a clinical testing procedure, e.g., to, for example, determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}I$, $^{131}I$, $^{35}S$ or $^{3}H$.

Antigens and Vaccines

Embodiments of the invention include preparations, e.g., antigenic preparations, of the entire mutant ESR1 or a fragment thereof, e.g., a fragment capable of raising antibodies specific to the fusion junction created by the deletion in the ligand binding domain of ESR1 (collectively referred to herein as a mutant specific polypeptides or MSP). The preparation can include an adjuvant or other component.

An MSP can be used as an antigen or vaccine. For example, an MSP can be used as an antigen to immunize an animal, e.g., a rodent, e.g., a mouse or rat, rabbit, horse, goat, dog, or non-human primate, to obtain antibodies, e.g., mutant protein specific antibodies. In an embodiment a mutant specific antibody molecule is an antibody molecule described herein, e.g., a polyclonal. In other embodiments a mutant specific antibody molecule is monospecific, e.g., monoclonal, human, humanized, chimeric or other monospecific antibody molecule. The mutant protein specific antibody molecules can be used to treat a subject having cancer, e.g., a cancer described herein.

Embodiments of the invention include vaccine preparations that comprise an MSP capable of stimulating an immune response in a subject, e.g., by raising, in the subject, antibodies specific to the mutant protein. The vaccine preparation can include other components, e.g., an adjuvant. The vaccine preparations can be used to treat a subject having cancer, e.g., a cancer described herein.

In other embodiments, the preparations include the entire mutant ESR1 gene, or a fragment comprising the mutation in ESR1. The mutation can be an amino acid substitution or insertion as well as a deletion.

Expression Vectors, Host Cells and Recombinant Cells

In another aspect, the invention includes vectors (e.g., expression vectors), containing a nucleic acid encoding a mutant ESR1 polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a mutant ERS1 nucleic acid in a form suitable for expression of the nucleic acid in a host cell. Typically, the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors can be introduced into host cells to thereby produce the mutant ESR1 polypeptide, including proteins or polypeptides encoded by nucleic acids as described herein, mutant forms thereof, and the like).

The term "recombinant host cell" (or simply "host cell" or "recombinant cell"), as used herein, is intended to refer to a cell into which a recombinant expression vector has been introduced. It should be understood that such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein.

The recombinant expression vectors can be designed for expression of a mutant ESR1 polypeptide in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either mutant or wildtype proteins. Mutant vectors add a number of amino acids to a protein encoded therein, usually to the amino terminus of the recombinant protein. Such mutant vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the added amino acids and the recombinant protein to enable separation of the recombinant protein from the fusion moiety subsequent to purification of the mutant protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified mutant ESR1 polypeptides can be used in activity assays (e.g., direct assays or competitive assays described in detail below), or to generate antibodies specific for mutant ESR1 polypeptides.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The mutant ESR1 polypeptide expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) Cell 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a mutant ESR1 nucleic acid molecule within a recombinant expression vector or a mutant ESR1 nucleic acid molecule containing sequences which allow it to homologous recombination into a specific site of the host cell's genome.

A host cell can be any prokaryotic or eukaryotic cell. For example, a mutant ESR1 polypeptide can be expressed in bacterial cells (such as *E. coli*), insect cells, yeast or mammalian cells (such as Chinese hamster ovary cells (CHO) or COS cells, e.g., COS-7 cells, CV-1 origin SV40 cells; Gluzman (1981) *Cell* 23:175-182). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell can be used to produce (e.g., express) a mutant ESR1 polypeptide. Accordingly, the invention further provides methods for producing a mutant ESR1 polypeptide using the host cells. In one embodiment, the method includes culturing the host cell of the invention (into which a recombinant expression vector encoding a mutant ESR1 polypeptide has been introduced) in a suitable medium such that a mutant ESR1 polypeptide is produced. In another embodiment, the method further includes isolating a mutant ESR1 polypeptide from the medium or the host cell.

In another aspect, the invention features, a cell or purified preparation of cells which include a mutant ESR1 transgene, or which otherwise misexpress mutant ESR1. The cell preparation can consist of human or non-human cells, e.g., rodent cells, e.g., mouse or rat cells, rabbit cells, or pig cells. In embodiments, the cell or cells include a mutant ESR1 transgene, e.g., a heterologous form of the mutant ESR1, e.g., a gene derived from humans (in the case of a non-human cell). The mutant ESR1 transgene can be misexpressed, e.g., overexpressed or underexpressed. In other embodiments, the cell or cells include a gene that misexpresses an endogenous mutant ESR1, e.g., a gene the expression of which is disrupted, e.g., a knockout. Such cells can serve as a model for studying disorders that are related to mutated or mis-expressed ESR1 alleles (e.g., cancers) or for use in drug screening, as described herein.

Therapeutic Methods

Alternatively, or in combination with the methods described herein, the invention features a method of treating a cancer or tumor harboring a mutant ESR1 gene as described herein. The methods include administering an anti-cancer agent, e.g., an SERM or an aromatase, alone or in combination, e.g., in combination with other chemotherapeutic agents or procedures, in an amount sufficient to reduce or inhibit the tumor cell growth, and/or treat or prevent the cancer(s), in the subject.

"Treat," "treatment," and other forms of this word refer to the administration of a SERM or an aromatase, alone or in combination with a second agent to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of a compound is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of a compound is an amount sufficient to prevent re-growth of the cancer, or one or more symptoms associated with the cancer, or prevent its recurrence. A prophylactically effective amount of a compound means an amount of the compound, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g, infant, child, adolescent) or adult patient (e.g., young adult, middle-aged adult or senior adult) or other mammal, such as a primate (e.g., cynomolgus monkey, rhesus monkey); commercially relevant mammals such as cattle, pigs, horses, sheep, goats, cats, and/or dogs; and/or birds, including commercially relevant birds such as chickens, ducks, geese, and/or turkeys, that will be or has been the object of treatment, observation, and/or experiment. When the term is used in conjunction with administration of a compound or drug, then the patient has been the object of treatment, observation, and/or administration of the compound or drug.

In certain embodiments, the cancer includes, but is not limited to, a solid tumor, a soft tissue tumor, and a metastatic lesion (e.g., a cancer as described herein). In one embodiment, the cancer is chosen from a breast cancer, a prostate cancer, an endometrial cancer, an ovarian cancer, and a colon cancer.

In other embodiments, the cancer is chosen from lung cancer, thyroid cancer, colorectal cancer, adenocarcinoma, melanoma, B cell cancer, bronchus cancer, cancer of the oral cavity or pharynx, cancer of hematological tissues, cervical cancer, esophageal cancer, esophageal-gastric cancer, gastric cancer, kidney cancer, liver cancer, multiple myeloma, pancreatic cancer, salivary gland cancer, small bowel or appendix cancer, stomach cancer, testicular cancer, urinary bladder cancer, uterine cancer, inflammatory myofibroblastic tumors, gastrointestinal stromal tumor (GIST), and the like.

In one embodiment, the anti-cancer agent is an SERM ("Selective Estrogen Receptor Modulator"). For example, the SERM can be chosen from raloxifene (Evista®), EM652, GW7604, keoxifene, toremifene (Fareston®), tamoxifen (Nolvadex®), lasofoxifene, levormeloxifene, bazedoxifene, or arzoxifene. In another embodiment the anti-cancer agent is the estrogen antagonist fulvestrant (ICI 182, 780; Faslodex®), which also acts to promote degradation of the estrogen rector.

In another embodiment the anti-cancer agent is an aromatase inhibitor chosen from aminoglutethimide, testolactone (Teslac®), anastrozole (Arimidex®), letrozole (Femara®), exemestane (Aromasin®), vorozole (Rivizor), formestane (Lentaron®), fadrozole (Afema); 4-hydroxyandrostenedione, 1,4,6-androstatrien-3, 17-dione (ATD), and 4-Androstene-3,6,17-trione ("6-OXO").

In other embodiments, the anti-cancer agent is an ESR1 antagonist that inhibits the expression of nucleic acid encoding a mutant ESR1, such as a mutant ESR1 described herein. Examples of such antagonists include nucleic acid molecules, for example, antisense molecules, ribozymes, RNAi, triple helix molecules that hybridize to a nucleic acid encoding ESR1, or a transcription regulatory region, and blocks or reduces mRNA expression of mutant ESR1.

In other embodiments, the SERM, aromatase inhibitor or other estrogen inhibitor is administered in combination with a second therapeutic agent or a different therapeutic modality, e.g., anti-cancer agents, and/or in combination with surgical and/or radiation procedures. In other embodiments, the SERM, aromatase inhibitor or other estrogen inhibitor is administered in combination with a second therapeutic agent or a different therapeutic modality, e.g., to treat a symptom of chemotherapy such as for treatment of nausea or headache.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. It will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

For example, the second therapeutic agent can be a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon α or γ, or immune cell growth factors such as GM-CSF.

Anti-cancer agents, e.g., estrogen inhibitors such as SERMs and aromatase inhibitors, used in the therapeutic methods featured in the invention can be evaluated using the screening assays described herein. In one embodiment, the anti-cancer agents are evaluated in a cell-free system, e.g., a cell lysate or in a reconstituted system. In other embodiments, the anti-cancer agents are evaluated in a cell in culture, e.g., a cell expressing a mutant ESR1 gene (e.g., a mammalian cell, a tumor cell or cell line, a recombinant cell). In yet other embodiments, the anti-cancer agents are evaluated cell in vivo (a mutant ESR1-expressing cell present in a subject, e.g., an animal subject (e.g., an in vivo animal model).

Exemplary parameters evaluated include one or more of:
(i) a change in binding activity, e.g., direct binding of the candidate agent to a mutant ESR1 polypeptide; a binding competition between a known ligand (e.g., estrogen or an estrogen inhibitor, such as tamoxifen) and the candidate agent to a mutant ESR1 polypeptide;
(ii) a change in estrogen receptor activity, e.g., binding of estrogen to the mutant ESR1 receptor polypeptide (e.g., an increased or decreased binding of estrogen); or a change in Activation Function activity, e.g., decreased or increased transcription activation activity; or a change in DNA binding activity;

(iii) a change in an activity of a cell containing a mutant ESR1 (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a mutant ESR1 polypeptide or nucleic acid molecule.

In one embodiment, a change in a cell free assay in the presence of a candidate agent is evaluated. For example, an activity of a mutant ESR1 polypeptide, or interaction of a mutant ESR1 polypeptide with a ligand (e.g., estrogen or tamoxifen, or a DNA target sequence) can be detected.

In other embodiments, a change in an activity of a cell is detected in a cell in culture, e.g., a cell expressing a mutant ESR1 polypeptide (e.g., a mammalian cell, a tumor cell or cell line, a recombinant cell). In one embodiment, the cell is a recombinant cell that is modified to express a mutant ESR1 nucleic acid, e.g., is a recombinant cell transfected with a mutant ESR1 nucleic acid. The transfected cell can show a change in response to the expressed mutant ESR1, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, or transformed morphology, in the presence of the candidate agent can be indicative of an inhibitor of a mutant ESR1. In other embodiments, a change in binding activity or phosphorylation as described herein is detected.

In yet other embodiments, a change in a tumor present in an animal subject (e.g., an in vivo animal model) is detected. In one embodiment, the animal model is a tumor containing animal or a xenograft comprising cells expressing a mutant ESR1 (e.g., tumorigenic cells expressing a mutant ESR1). The anti-cancer agents can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

The screening methods and assays are described in more detail herein below.

Screening Methods

In another aspect, the invention features a method, or assay, for screening for agents that modulate, e.g., inhibit, the expression or activity of a mutant ESR1, e.g., a mutant ESR1 as described herein. The method includes contacting a mutant ESR1 polypeptide, or a cell expressing a mutant ESR1, with a candidate agent; and detecting a change in a parameter associated with the mutant ESR1, e.g., a change in the expression or an activity of the mutant ESR1. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the mutant ESR1 is detected, the candidate agent is identified as an inhibitor. In another embodiment, if an increase in expression or activity of the mutant ESR1 is detected, the candidate agent is identified as an activator. In certain embodiments, the mutant ESR1 is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a mutant ESR1 (e.g., a mammalian cell, a tumor cell or cell line, a recombinant cell). In yet other embodiments, the contacting step is effected in a cell in vivo (a mutant ESR1-expressing cell present in a subject, e.g., an animal subject (e.g., an in vivo animal model).

Exemplary parameters evaluated include one or more of:

(i) a change in binding activity, e.g., direct binding of the candidate agent to a mutant ESR1 polypeptide; a binding competition between a known ligand (e.g., estrogen, or an estrogen inhibitor, such as tamoxifen) and the candidate agent to a mutant ESR1 polypeptide;

(ii) a change in transcriptional activation activity or DNA binding activity as measured, for example, by fusing an estrogen response element (ERE) to a reporter gene; DNA binding activity can also be measure by gel-shift assay;

(iii) a change in an activity of a cell containing a mutant ESR1 (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a mutant ESR1 polypeptide or nucleic acid molecule.

In one embodiment, a change in a cell free assay in the presence of a candidate agent is evaluated. For example, an activity of a mutant ESR1 polypeptide, or interaction of a mutant ESR1 polypeptide with a ligand can be detected. In one embodiment, a mutant ESR1 polypeptide is contacted with a ligand, e.g., in solution, and a candidate agent is monitored for an ability to modulate, e.g., inhibit, an interaction, e.g., binding, between the mutant ESR1 polypeptide and the ligand. In one exemplary assay, purified ESR1 protein is contacted with a ligand, e.g., in solution, and a candidate agent is monitored for an ability to inhibit interaction of the protein with the ligand, or to inhibit activity (e.g., DNA binding activity) of the mutant ESR1 protein. An effect on an interaction between the mutant protein and a ligand can be monitored by methods known in the art, such as by absorbance, and an effect on ESR1 activity levels, e.g., DNA binding or transcription activation activity of the mutant ESR1 can be assayed, e.g., by gel-shift assays, reporter gene assays, and other methods known in the art.

In other embodiments, a change in an activity of a cell is detected in a cell in culture, e.g., a cell expressing a mutant ESR1 polypeptide (e.g., a mammalian cell, a tumor cell or cell line, a recombinant cell). In one embodiment, the cell is a recombinant cell that is modified to express a mutant ESR1 nucleic acid, e.g., is a recombinant cell transfected with a mutant ESR1 nucleic acid. The transfected cell can show a change in response to the expressed mutant ESR1, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a mutant ESR1. In other embodiments, a change in binding activity or phosphorylation as described herein is detected.

In an exemplary cell-based assay, a nucleic acid comprising a mutant ESR1 can be expressed in a cell, such as a cell (e.g., a mammalian cell) in culture. The cell containing a nucleic acid expressing the mutant ESR1 can be contacted with a candidate agent, and the cell is monitored for an effect of the candidate agent. A candidate agent that causes decreased cell proliferation or cell death can be determined to be a candidate for treating a tumor (e.g., a cancer) that carries a mutant ESR1.

In one embodiment, a cell containing a nucleic acid expressing a mutant ESR1 can be monitored for expression of the mutant ESR1 protein. Protein expression can be monitored by methods known in the art, such as by, e.g., mass spectrometry (e.g., tandem mass spectrometry), a reporter assay (e.g., a fluorescence-based assay), Western blot, and immunohistochemistry. By one method, decreased mutant ESR1 expression is detected. A candidate agent that causes decreased expression of the mutant ESR1 protein as compared to a cell that does not contain the mutant ESR1 nucleic acid can be determined to be a candidate for treating a tumor (e.g., a cancer) that carries a mutant ESR1.

A cell containing a nucleic acid expressing a mutant ESR1 can be monitored for altered DNA binding or transcriptional activation activity. Transcriptional activation activity can be assayed by measuring the effect of a candidate agent on expression of a reporter gene under control of a ERE (estrogen response element). An ERE has the consensus sequence GGTCANNNTGACC (SEQ ID NO: 5) (Klein-Hitpass et al., Cell 46:1053-1061, 1986).

In yet other embodiments, a change in a tumor present in an animal subject (e.g., an in vivo animal model) is detected. In one embodiment, the animal model is a tumor containing animal or a xenograft comprising cells expressing a mutant ESR1 (e.g., tumorigenic cells expressing a ESR1 that carries a mutation in the ligand binding domain). The candidate agent can be administered to the animal subject and a change in the tumor is detected. In one embodiment, the change in the tumor includes one or more of a tumor growth, tumor size, tumor burden, or survival. A decrease in one or more of tumor growth, tumor size, tumor burden, or an increased survival is indicative that the candidate agent is an inhibitor.

In one exemplary animal model, a xenograft is created by injecting cells into a mouse. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. The health of the animal is also monitored, such as to determine if an animal treated with a candidate agent survives longer. A candidate agent that causes growth of the tumor to slow or stop, or causes the tumor to shrink in size, or causes decreased tumor burden, or increases survival time, can be considered to be a candidate for treating a tumor (e.g., a cancer) that carries an ESR1 mutation.

In another exemplary animal assay, cells expressing a mutant ESR1 are injected into the tail vein, e.g., of a mouse, to induce metastasis. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. A candidate agent that inhibits or prevents or reduces metastasis, or increases survival time, can be considered to be a candidate for treating a tumor (e.g., a cancer) that carries a mutant ESR1.

Cell proliferation can be measured by methods known in the art, such as PCNA (Proliferating cell nuclear antigen) assay, 5-bromodeoxyuridine (BrdUrd) incorporation, Ki-67 assay, mitochondrial respiration, or propidium iodide staining. Cells can also be measured for apoptosis, such as by use of a TUNEL (Terminal Deoxynucleotide Transferase dUTP Nick End Labeling) assay. Cells can also be assayed for presence of angiogenesis using methods known in the art, such as by measuring endothelial tube formation or by measuring the growth of blood vessels from subcutaneous tissue, such as into a solid gel of basement membrane.

In other embodiments, a change in expression of a mutant ESR1can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based assay described herein can be further tested in an animal subject.

In one embodiment, the candidate agent is identified and re-tested in the same or a different assay. For example, a test compound is identified in an in vitro or cell-free system, and re-tested in an animal model or a cell-based assay. Any order or combination of assays can be used. For example, a high throughput assay can be used in combination with an animal model or tissue culture.

Candidate agents suitable for use in the screening assays described herein include, e.g., small molecule compounds, nucleic acids (e.g., siRNA, aptamers, short hairpin RNAs, antisense oligonucleotides, ribozymes, antagomirs, microRNA mimics or DNA, e.g., for gene therapy) or polypeptides, e.g., antibodies (e.g., full length antibodies or antigen-binding fragments thereof, Fab fragments, or scFv fragments). The candidate anti-cancer agents can be obtained from a library (e.g., a commercial library), or can be rationally designed, such as to target an active site in a functional domain of ESR1 (e.g., the ligand binding domain of ESR1).

In other embodiments, the method, or assay, includes providing a step based on proximity-dependent signal generation, e.g., a two-hybrid assay that includes a first mutant protein (e.g., a mutant ESR1 protein), and a second protein (e.g., a ligand), contacting the two-hybrid assay with a test compound, under conditions wherein said two hybrid assay detects a change in the formation and/or stability of the complex, e.g., the formation of the complex initiates transcription activation of a reporter gene.

In one non-limiting example, the three-dimensional structure of the ligand binding domain of the mutant ESR1 is determined by crystallizing the complex formed by the mutant ESR1 and a known inhibitor. Rational drug design is then used to identify new test agents by making alterations in the structure of a known inhibitor or by designing small molecule compounds that bind to the ligand binding domain of the ESR1 polypeptide.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means known in the art (e.g., using a fluorimeter).

In another embodiment, determining the ability of the mutant ESR1 protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Nucleic Acid Inhibitors

In yet another embodiment, the mutant ESR1 inhibitor inhibits the expression of nucleic acid encoding a mutant ESR1. Examples of such mutant ESR1 inhibitors include nucleic acid molecules, for example, antisense molecules, ribozymes, siRNA, triple helix molecules that hybridize to a nucleic acid encoding a mutant ESR1, or a transcription regulatory region, and blocks or reduces mRNA expression of the mutant ESR1.

In one embodiment, the nucleic acid antagonist is a siRNA that targets mRNA encoding mutant ESR1. Other types of antagonistic nucleic acids can also be used, e.g., a dsRNA, a ribozyme, a triple-helix former, or an antisense nucleic acid. Accordingly, isolated nucleic acid molecules that are nucleic acid inhibitors, e.g., antisense, RNAi, to a mutant ESR1-encoding nucleic acid molecule are provided.

An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire mutant ESR1 coding strand, or to only a portion thereof. For example, the antisense nucleic acid can be complementary to the sequence in the ligand-binding domain that carries the mutation, e.g., can be complementary to the fusion junction in the ligand-binding domain created by the six-nucleotide deletion described herein. In another embodiment, the antisense nucleic acid molecule is antisense to a "noncoding region" of the coding strand of a nucleotide sequence encoding a mutant ESR1 (e.g., the 5' and 3' untranslated regions). Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding mutant ESR1. The complementary region can extend for between about 8 to about 80 nucleobases. The compounds can include one or more modified nucleobases. Modified nucleobases are known in the art. Descriptions of modified nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The antisense nucleic acid molecules of the invention are typically administered to a subject (e.g., by direct injection at a tissue site), or generated in situ such that they hybridize with or bind to cellular mRNA and/or genomic DNA encoding a mutant ESR1 to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are typical.

In yet another embodiment, the antisense nucleic acid molecule of the invention is an a-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215: 327-330).

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature*. 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

In still another embodiment, an antisense nucleic acid of the invention is a ribozyme. A ribozyme having specificity for a mutant ESR1-encoding nucleic acid can include one or more sequences complementary to the nucleotide sequence of a mutant ESR1 cDNA disclosed herein (i.e., SEQ ID NO:3), and a sequence having known catalytic sequence responsible for mRNA cleavage (see U.S. Pat. No. 5,093, 246 or Haselhoff and Gerlach (1988) *Nature* 334:585-591). For example, a derivative of a *Tetrahymena* L-19 IVS RNA can be constructed in which the nucleotide sequence of the active site is complementary to the nucleotide sequence to be cleaved in a mutant ESR1-encoding mRNA. See, e.g., Cech et al. U.S. Pat. No. 4,987,071; and Cech et al. U.S. Pat. No. 5,116,742. Alternatively, mutant ESR1 mRNA can be used to select a catalytic RNA having a specific ribonuclease activity from a pool of RNA molecules. See, e.g., Bartel, D. and Szostak, J. W. (1993) *Science* 261:1411-1418.

Mutant ESR1 gene expression can be inhibited by targeting nucleotide sequences complementary to the regulatory region of the mutant ESR1 to form triple helical structures that prevent transcription of the mutant ESR1 gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecules. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A mutant ESR1 nucleic acid molecule can be modified at the base moiety, sugar moiety or phosphate backbone to improve, e.g., the stability, hybridization, or solubility of the molecule. For non-limiting examples of synthetic oligonucleotides with modifications see Toulmé (2001) *Nature Biotech.* 19:17 and Faria et al. (2001) *Nature Biotech.* 19:40-44. Such phosphoramidite oligonucleotides can be effective antisense agents.

For example, the deoxyribose phosphate backbone of the nucleic acid molecules can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675.

PNAs of mutant ESR1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of mutant ESR1 nucleic acid molecules can also be used in the analysis of single base pair mutations in a gene (e.g., by PNA-directed PCR clamping); as 'artificial restriction enzymes' when used in combination with other enzymes (e.g., S1 nucleases (Hyrup B. et al. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc.*

Natl. Acad. Sci. USA 84:648-652; WO88/09810) or the blood-brain barrier (see, e.g., WO 89/10134). In addition, oligonucleotides can be modified with hybridization-triggered cleavage agents (see, e.g., Krol et al. (1988) *BioTechniques* 6:958-976) or intercalating agents (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

Evaluation of Subjects

Subjects, e.g., patients, can be evaluated for the presence of a mutant ESR1. A patient can be evaluated, for example, by determining the genomic sequence of the patient, e.g., by an NGS method. Alternatively, or in addition, evaluation of a patient can include directly assaying for the presence of a mutant ESR1 in the patient, such as by an assay to detect a mutant ESR1 nucleic acid (e.g., DNA or RNA), such as by, Southern blot, Northern blot, or RT-PCR, e.g., qRT-PCR. Alternatively, or in addition, a patient can be evaluated for the presence of a mutant ESR1 protein, such as by immunohistochemistry, Western blot, immunoprecipitation, or immunomagnetic bead assay.

Evaluation of a patient can also include a cytogenetic assay, such as by fluorescence in situ hybridization (FISH), to identify the chromosomal rearrangement resulting in the mutant ESR1. For example, to perform FISH, at least a first probe tagged with a first detectable label can be designed to target a sequence in the ligand binding domain of ESR1, e.g., in one or more of exons 8-12 of KIF5B (see FIG. 1).

Additional methods for mutant ESR1 detection are provided below.

In one aspect, the results of a clinical trial, e.g., a successful or unsuccessful clinical trial, can be repurposed to identify agents that target a mutant ESR1. By one exemplary method, a candidate agent used in a clinical trial can be reevaluated to determine if the agent in the trial targets a mutant ESR1, or is effective to treat a tumor containing a mutant ESR1. For example, subjects who participated in a clinical trial for an agent, such as an estrogen inhibitor, can be identified. Patients who experienced an improvement in symptoms, e.g., cancer (e.g., breast cancer) symptoms, such as decreased tumor size, or decreased rate of tumor growth, can be evaluated for the presence of a mutation in the ligand binding domain of ESR1. Patients who did not experience an improvement in cancer symptoms can also be evaluated for the presence of an ESR1 mutation. Where patients carrying a mutation in the ligand binding domain of ESR1 are found to have been more likely to respond to the test agent than patients who did not carry a mutation in the ligand binding domain, then the agent is determined to be an appropriate treatment option for a patient carrying the mutant ESR1.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of an ESR1 mutation in the patient, such as by an assay to detect a mutant ESR1 nucleic acid (e.g., RNA), such as by RT-PCR, e.g., qRT-PCR. Alternatively, or in addition, a patient can be evaluated for the presence of a mutant ESR1 protein, such as by immunohistochemistry, Western blot, immunoprecipitation, or immunomagnetic bead assay.

Clinical trials suitable for repurposing as described above include trials that tested estrogen receptor inhibitors, or estrogen mimics, SERMs or aromatase inhibitors.

Methods for Detection of Mutant ESR1 Nucleic Acids and Polypeptides

Methods for evaluating an ESR1 gene, mutations and/or gene products are known to those of skill in the art. In one embodiment, the mutant ESR1 is detected in a nucleic acid molecule by a method chosen from one or more of: nucleic acid hybridization assays, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In certain embodiments, the evaluation methods include the probes/primers described herein.

In one embodiment, probes/primers can be designed to detect a mutation in ESR1. The ESR1 probes/primers can be from nucleotides 1-1788 of SEQ ID NO:1, or from nucleotides 1-1782 of SEQ ID NO:3 (e.g., can hybridize to the nucleotides encoding exons 5b-12 of the ESR1 protein). In some embodiments, the ESR1 probes/primers can be from nucleotides 934-1638 of SEQ ID NO:1 or nucleotides 934-1632 of SEQ ID NO:3 (e.g., can hybridize to the nucleotides encoding exons 8-12 of the ESR1 protein). These probes/primers are suitable, e.g., for PCR amplification. For PCR, e.g., to amply the region including the ligand binding domain of ESR1, forward primers can be designed to hybridize to ESR1 sequence from nucleotide 761 of SEQ ID NO:1, and reverse primers can be designed to hybridize from nucleotide 2158 of SEQ ID NO:1.

In one embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used in the methods of the invention. In fluorogenic quantitative PCR, quantitation is based on amount of fluorescence signals, e.g., TaqMan® and SYBR® green.

In one embodiment, a TaqMan® assay is used to identify a deletion in the ER gene, e.g., a 6 nucleotide deletion as described herein, such as by utilizing a probe that binds specifically to the fusion junction created by the deletion, and a control probe that binds to the wildtype sequence, and probes that bind outside of the mutated sequence for PCR amplification.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Chromosomal probes are typically about 50 to about $10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromsome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

Additional exemplary methods include, traditional "direct probe" methods such as Southern blots or in situ hybridization (e.g., fluorescence in situ hybridization (FISH) and FISH plus SKY), and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

Additional protocols for FISH detection are described below.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe. Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)-or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin(BIO)-11-dUTP, Digoxygenin(DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2× SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2× SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the chromosomal probes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation from a tissue sample are known in the art. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods can further include isolating a nucleic acid sample to provide a library (e.g., a nucleic acid library). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, less than 500 ng, less than 200 ng, less than 100 ng, less than 50 ng or less than 20 ng (e.g., 10 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample (e.g., DNA or RNA sample) by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit). Alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, or 20 ng or less of nucleic acid sample. For example, to prepare 500 ng of hybridization-ready nucleic acids, one typically begins with 3 µg of genomic DNA. One can start with less, however, if one amplifies the genomic DNA (e.g., using PCR) before the step of solution hybridization. Thus it is possible, but not essential, to amplify the genomic DNA before solution hybridization.

In some embodiments, a library is generated using DNA (e.g., genomic DNA) from a sample tissue, and a corresponding library is generated with RNA (or cDNA) isolated from the same sample tissue.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) Nat Biotechnol. 27(2):182-189, and U.S. Ser. No. 61/428,568, filed Dec. 30, 2010, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Each bait sequence can include a target-specific (e.g., a member-specific) bait sequence and universal tails on each end. As used herein, the term "bait sequence" can refer to the target-specific bait sequence or the entire oligonucleotide including the target-specific "bait sequence" and other nucleotides of the oligonucleotide. In one embodiment, a target-specific bait sequence hybridizes to a nucleic acid sequence comprising a nucleic acid sequence in exons 8, 9, 10, 11, or 12 of ESR1, e.g., in exon 8 of ESR1.

In one embodiment, the bait is an oligonucleotide about 200 nucleotides in length, of which 170 nucleotides are target-specific "bait sequence." The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGT$N_{170}$CACTGCGGCTCCTCA-3' with $N_{170}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

Sequencing

The invention also includes methods of sequencing nucleic acids. In one embodiment, any of a variety of sequencing reactions known in the art can be used to directly sequence at least a portion of a mutant ESR1. In one embodiment, the mutant ESR1 sequence is compared to a corresponding reference (control) sequence.

In one embodiment, the sequence of the mutant ESR1 nucleic acid molecule is determined by a method that includes one or more of: hybridizing an oligonucleotide, e.g., an allele specific oligonucleotide for one alteration described herein to said nucleic acid; hybridizing a primer, or a primer set (e.g., a primer pair), that amplifies a region comprising the mutation or a fusion junction of the allele; amplifying, e.g., specifically amplifying, a region comprising the mutation or a fusion junction of the allele; attaching an adapter oligonucleotide to one end of a nucleic acid that comprises the mutation or a fusion junction of the allele; generating an optical, e.g., a colorimetric signal, specific to the presence of the one of the mutation or fusion junction; hybridizing a nucleic acid comprising the mutation or fusion junction to a second nucleic acid, e.g., a second nucleic acid attached to a substrate; generating a signal, e.g., an electrical or fluorescent signal, specific to the presence of the mutation or fusion junction; and incorporating a nucleotide into an oligonucleotide that is hybridized to a nucleic acid that contains the mutation or fusion junction.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled *DNA Sequencing by Mass Spectrometry Via Exonuclease Degradation* by H. Köster), and U.S. Pat. No. 5,605,798 and International Patent Application No. PCT/US96/03651 entitled *DNA Diagnostics Based on Mass Spectrometry* by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif.; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template Preparation

Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amounts of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adapters containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5): 510-6). MDA is a non-PCR based DNA amplification technique. The reaction involves annealing random hexamer primers to the template and DNA synthesis by high fidelity enzyme, typically Φ29 at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods*, 2007, 4:931-936; Krishnakumar S. et al., *Proc. Natl. Acad. Sci. USA*, 2008, 105:9296-9310; Turner E. H. et al., *Nature Methods*, 2009, 6:315-316), and biotinylated RNA capture sequences (Gnirke A. et al., *Nat. Biotechnol.* 2009; 27(2): 182-9)

Single-molecule templates are another type of templates that can be used for NGS reaction. Spatially separated single molecule templates can be immobilized on solid supports by various methods. In one approach, individual primer molecules are covalently attached to the solid support. Adapters are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and Imaging

Exemplary sequencing and imaging methods for NGS include, but are not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but are not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a 5'-PO$_4$ group for subsequent ligation cycles. Alternatively, a new primer can be hybridized to the template after the old primer is removed. Exemplary SBL platforms include, but are not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platforms include, but are not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms include, but are not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI-COR Biosciences platform, which uses dye-quencher nucleotides in the sequencing reaction.

Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat Biotechnol.* 2008; 26(10):1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics*, 2007, 23:500-501; Butler J. et al., *Genome Res.*, 2008, 18:810-820; and Zerbino D. R. and Birney E., *Genome Res.*, 2008, 18:821-829.

Sequence alignment or assembly can be performed using read data from one or more NGS platforms, e.g., mixing Roche/454 and Illumina/Solexa read data.

Algorithms and methods for data analysis are described in U.S. Ser. No. 61/428,568, filed Dec. 30, 2010, incorporated herein by reference.

Mutant ESR1 Expression Level

In certain embodiments, mutant ESR1 expression levels can also be assayed. Mutant ESR1 expression can be assessed by any of a wide variety of methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. Mutant ESR1expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the mutant ESR1gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the mutant ESR1 cDNA, e.g., using the probes and primers described herein.

In other embodiments, mutant ESR1 expression is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the mutant ESR1, and fragments thereof. cDNA can, optionally, be amplified using any of a variety of polymerase chain reaction methods prior to hybridization with the reference polynucleotide. Expression of mutant ESR1 can likewise be detected using quantitative PCR (QPCR) to assess the level of mutant ESR1 expression.

Detection of Mutant ESR1 Polypeptide

The activity or level of a mutant ESR1 polypeptide can also be detected and/or quantified by detecting or quantifying the expressed polypeptide. The mutant ESR1 polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a mutant ESR1 polypeptide is an antibody molecule capable of binding to a polypeptide corresponding to a marker of the invention, e.g., an antibody with a detectable label. Techniques for generating antibodies are described herein. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair (e.g., biotin-streptavidin)), or an antibody fragment (e.g., a single-chain antibody, an isolated antibody hypervariable domain, etc.) which binds specifically with a mutant ESR1 protein, is used.

Mutant ESR1 polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The mutant ESR1 polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

Kits

In one aspect, the invention features, a kit, e.g., containing an oligonucleotide having a mutation described herein, e.g., an oligonucleiotide that hybridizes specifically to a mutation in the ligand binding domain of ESR1. Optionally, the kit can also contain an oligonucleotide that is the wildtype counterpart of the mutant oligonucleotide.

A kit featured in the invention can include a carrier, e.g., a means being compartmentalized to receive in close confinement one or more container means. In one embodiment the container contains an oligonucleotide, e.g., a primer or probe as described above. The components of the kit are useful, for example, to diagnose identify a mutation in a tumor sample in a patient, and to accordingly identify an appropriate therapeutic agent to treat the cancer. The probe or primer of the kit can be used in any sequencing or nucleotide detection assay known in the art, e.g., a sequencing assay, e.g., an NGS method, RT-PCR, or in situ hybridization.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. When an oligonucleotide, e.g., an oligonucleotide that contains a mutation in ESR1, e.g., a mutation in the ligand binding domain of ESR1 as described herein, or an oligonucleotide complementary to an ESR1 mutation, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in a sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds specifically to a mutant ESR1 polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a nucleic acid containing a mutation described in the Example. The assay provider, e.g., a service provider or healthcare provider, can then conclude that the subject is, or is not, a candidate for a particular drug or a particular cancer treatment regimen.

The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

The invention is further illustrated by the following example, which should not be construed as further limiting.

EXAMPLES

Example 1

Massively Parallel Sequencing Assays to Identify Novel Alterations

The following exemplifies the use of massively parallel sequencing assays to identify novel alterations, such as mutations in the estrogen receptor gene ESR1.

Massively parallel sequencing technology was used to examine eight formalin fixed paraffin embedded (FFPE) samples of breast cancer metastases in bone, lung and liver (Table 1). This assay can identify all classes of DNA alterations (e.g., base substitutions, insertions and deletions, copy number alterations and rearrangements) in a single diagnostic test.

The sequencing analysis identified a 6-nucleotide non-frameshift deletion in the ESR1 gene in the ligand-binding domain (see FIG. 1). The mutation is a deletion of nucleotides 1046-1051 according to SEQ ID NO:1, which results in the deletion of amino acids LAD at positions 349 to 351 of SEQ ID NO:2 (FIG. 2B), and insertion of a histidine at position 349 of SEQ ID NO:4 (FIG. 4B). To our knowledge, this region of the ligand binding domain of ESR1 has not previously been identified as a recurrent site of mutation in human breast cancers.

The novel 6-nucleotide deletion occurs in a region of the ligand binding domain previously associated with resistance to treatment with SERMs (Selective Estrogen Receptor Modulators), such as tamoxifen. For example, a D351Y or D351E mutation results in a receptor that exhibits an estrogenic response to SERMs, including raloxifene, EM652, GW7604, keoxifene and tamoxifen (Herynk and Fuqua, *Endocrine Reviews* 25:869-898, 2004). The effects of the pure antiestrogen fulvestrant (Faslodex®) are unaffected by mutating this site to tyrosine. Experimental mutagenesis of this site to glycine, valine, or phenylalanine does not result in a receptor that responds to antiestrogens in an agonistic manner. The antiestrogenic response of the D351Y mutant to antiestrogens requires the AF-1 domain because mutants with a deleted AF-1 domain lose the ability to increase ER transactivation in response to the antiestrogens tamoxifen and raloxifene. Although the AF-2 domain is not required, D351Y mutants possessing intact AF-1 and AF-2 domains produce a synergistic response to antiestrogens. Further, the D351Y mutant shows decreased interactions with the corepressors NCoR and SMRT (Herynk and Fuqua, *Endocrine Reviews* 25:869-898, 2004).

In vitro assays and crystallographic studies indicated that D351 is critical for the interaction with the antiestrogenic side chains of SERMs. Liu et al. (*J. Biol. Chem.*, 277:9189-9198, 2002) demonstrated that the raloxifene side chain both shields and neutralizes the negative charge at D351.

The location of the 6-nucleotide deletion suggests that this mutation may also cause resistance to SERMs, such as tamoxifen and raloxifene.

Example 2

Methods

The following exemplifies certain embodiments of the methods and experimental conditions used to identify the ESR1 mutation described in Example 1. Additional ESR1 screening can be done using, e.g., qRT-PCR analysis of cDNA prepared from a pre-selected tumor sample.

Massively parallel DNA sequencing was done on hybridization captured, adaptor ligation-based libraries using DNA isolated from archived fixed paraffin-embedded tissue. A combination of analysis tools were used to analyze the data and assign DNA alteration calls.

Genomic DNA Sequencing

Sequencing of cancer genes was done using DNA from archived formalin fixed paraffin embedded (FFPE) tumor specimens from breast cancer patients. Sequencing libraries were constructed by the adapter ligation method using genomic DNA followed by hybridization selection with optimized RNA hybridization capture probes (Agilent SureSelect custom kit). Sequencing on the HiSeq2000 instrument (Illumina) was done using 49×49 paired reads to an average depth of 514 X. Data processing and mutation assignments for base substitutions, indels, copy number alterations and genomic rearrangements were done using a combination of tools optimized for mutation calling from tumor tissue.

The sequencing results are summarized in the Tables below.

TABLE 1

Summary of Sequencing Results

| Tissue ID | DNA extraction yield | Mean exon coverage | Large-scale genomic rearrangements | Significant copy number gains/losses | Novel Variants |
|---|---|---|---|---|---|
| Bone 11 | 80 | 757 | | none | PTCH2:NM_001166292: c.1864C > A_p.H622N (0.40, 617), PTPRD:NM_130393:c.2095A > G_p.I699V (0.66, 589), ATM_c.378T > A_p.D126E (0.30, 759) |

TABLE 1-continued

Summary of Sequencing Results

| Tissue ID | DNA extraction yield | Mean exon coverage | Large-scale genomic rearrangements | Significant copy number gains/losses | Novel Variants |
|---|---|---|---|---|---|
| Bone 12 | 150 | 962 | SPAG5-RARA rearrangement (SPAG5 breakpoint in intron2, RARA breakpoint in exon 4), likely artifact of HER2 amp | ERBB2_gain (2.4x) | DOT1L:NM_032482:c.4210C > T_p.P1404S (0.50, 1939), ERCC2:NM_000400:c.1758 + 1C > G:splice (0.11, 551), ESR1:NM_001122742:c.437C > A_p.P146Q (0.56, 671), LTK:NM_206961:c.680C > T_p.P227L (0.48, 1559), PKHD1:NM_138694:c.10515C > A_p.S3505R (0.42, 866), PTCH1:NM_001083602:c.1610G > A_p.R537H (0.45, 958), PTPRD:NM_130393:c.91G > A_p.V31I (0.47, 754), RPTOR:NM_020761:c.3682G > A_p.V1228M (0.60, 1206), TSC1:NM_001162427:c.1607A > G_p.K536R (0.51, 703), ATM_c.5557G > A_p.D1853N (0.43, 607) |
| Bone 8 | 30 | 53 | | n/a - low coverage | CD79A:NM_001783:c.371G > A_p.R124H (0.20, 35), CDH20:NM_031891:c.1925T > C_p.M642T (0.40, 50), FGFR3:NM_022965:c.1936G > A_p.D646N (0.46, 67), IRS2:NM_003749:c.3098c > G_p.P1033R (0.14, 104), JAK2:NM_004972:c.2538G > C_p.E846D (0.56, 62), KDR:NM_002253:c.1066G > A_p.G356S (0.15, 48), MDM2:NM_002392:c.400C > T_p.H134Y (0.20, 65), MLL:NM_005933:c.2434A > G_p.K812E (0.13, 54), MUTYH:NM_001048171:c.1234C > T_p.R412C (0.42, 31), PAX5:NM_016734:c.39_39delG: frameshift (0.10, 170), PDGFRB:NM_002609:c.1504C > T_p.R502W (0.22, 63), PDGFRB:NM_002609:c.1505G > A_p.R502Q (0.73, 63), PTCH1:NM_001083603:c.131a > G_p.E44G (0.09, 111), ATM_c.5557G > A_p.D1853N (1.00, 55) |
| Bone 1 | 130 | 813 | | CCND1_gain (7.0x) | NF1:NM_001042492:c.2666C > G_p.T889R (0.53, 1063), ATM_c.2119T > C_p.S707P (0.25, 378), ATM_c.5557G > A_p.D1853N (0.72, 401), KIT_c.1621A > C_p.M541L (0.48, 683) |
| Bone 5 | 100 | 814 | | none | CDK4:NM_000075:c.122A > G_p.N41S (0.51, 881), ERBB2:NM_001005862:c.3285T > A_p.D1095E (0.44, 663), NOTCH1:NM_017617:c.3836G > A_p.R1279H (0.48, 1461), PIK3CA:NM_006218:c.716T > G_p.L239R (0.07, 1008), SMO:NM_005631:c.47_48insGCT: nonframeshift (0.18, 1004), TSC2:NM_001114382:c.275A > T_p.E92V (0.47, 841), |

TABLE 1-continued

Summary of Sequencing Results

| Tissue ID | DNA extraction yield | Mean exon coverage | Large-scale genomic rearrangements | Significant copy number gains/losses | Novel Variants |
|---|---|---|---|---|---|
| Bone 6 | 35 | 263 | CTNNB1 truncation | FGFR1_gain (2.3x) PAX5_loss (0.5x) | ATM_c.4138C > T_p.H1380Y (0.50, 867), ATM_c.5557G > A_p.D1853N (0.47, 618) BRCA2:NM_000059:c.4436G > C_p.S1479T (0.64, 346), CDKN2A:NM_001195132:c.254C > A_p.A85D (0.83, 475), DOT1L:NM_032482:c.4327G > T_p.G1443C (0.55, 487), ESR1:NM_001122742:c.1046_1051delTGGCAG: nonframeshift (0.20, 211), ESR1:NM_001122742:c.656A > G_p.Y219C (0.62, 184), LRP1B:NM_018557:c.1105A > G_p.T369A (0.11, 143), LRP1B:NM_018557:c.3259G > A_p.G1087S (0.10, 146), NOTCH1:NM_017617:c.3836G > A_p.R1279H (1.00, 601), NTRK1:NM_002529:c.482G > A_p.R161H (0.49, 147), PTCH2:NM_001166292:c.3269C > T_p.A1090V (0.47, 221), ATM_c.5557G > A_p.D1853N (0.99, 173), MSH2_c.965G > A_p.G322D (0.52, 327) |
| Liver 10 | 40 | 178 | | FGFR1_gain (2.2x), AKT3_gain (2.1) | BCL6:NM_001130845:c.492G > T_p.E164D (0.49, 173), CHEK2:NM_007194:c.480A > G_p.I160M (0.63, 154), FANCA:NM_000135:c.1874G > C_p.C625S (0.63, 123), FGFR1:NM_001174065:c.266A > G_p.Q89R (0.16, 460), FLT4:NM_002020:c.1936G > A_p.E646K (0.50, 145), MCL1:NM_182763:c.134G > A_p.R45Q (0.44, 248), PIK3R1:NM_181504:c.555_560delGTTTCA: nonframeshift (0.25, 362), JAK3_c.2164G > A_p.V722I (0.43, 84) |
| Lung 1 | 30 | 275 | | ERBB2_gain (3.1x), CCND1_gain (2.9x) | BAP1:NM_004656:c.1924G > A_p.E642K (0.11, 273), DDR2:NM_006182:c.1323G > A_p.M441I (0.44, 255), ERBB4:NM_005235:c.1122T > G_p.H374Q (0.47, 221), IKBKE:NM_014002:c.1912G > A_p.V638I (0.57, 268), INHBA:NM_002192:c.41G > T_p.C14F (0.50, 237), LRP1B:NM_018557:c.7420G > A_p.G2474S (0.51, 249), PIK3CG:NM_002649:c.400C > G_p.Q134E (0.53, 314), PTPRD:NM_130393:c.155G > T_p.R52I (0.15, 294), PTPRD:NM_130393:c.3073A > G_p.R1025G (0.06, 217), SMO:NM_005631:c.173C > T_p.P58L (0.45, 355), TET2:NM_001127208:c.100C > T_p.L34F (0.46, 205), USP9X:NM_001039591:c.3322G > A_p.D1108N (0.19, 366), ATM_c.5557G > A_p.D1853N (0.55, 213) |

TABLE 2

Somatic Mutations Identified

| Tissue ID | Somatic Mutations |
|---|---|
| Bone 11 | TP53_c.581T > G_p.L194R (0.27, 480) |
| Bone 12 | |
| Bone 8 | PIK3CA_c.1633G > A_p.E545K (0.44, 87), TP53_c.991C > T_p.Q331* (0.30, 37), CDH1:NM_004360:c.1531C > T_p.Q511* (0.29, 31) |
| Bone 1 | PIK3CA_c.3140A > T_p.H1047L (0.30, 902), CDH1:NM_004360:c.859_866del8:frameshift (0.40, 404) |
| Bone 5 | PIK3CA_c.3132T > A_p.N1044K (0.07, 931) |
| Bone 6 | TP53_c.489C > A_p.Y163* (0.80, 342) |
| Liver 10 | CDH1:NM_004360:c.841_859del19:frameshift (0.14, 152), TP53:NM_001126114:c.634_641del8:frameshift (0.24, 110) |
| Lung 1 | LRP1B:NM_018557:c.11818C > T_p.Q3940* (0.08, 346), TP53:NM_001126114:c.443_444insA:frameshift (0.14, 260) |

Example 3

Mutations Identified in ESR1 Hinge Region and Ligand Binding Domain

Several mutations in the ligand binding domain of ESR1 were identified in large-scale sequencing studies performed using the protocols described herein. These mutations were identified in various tumor samples, including breast, colorectal and non-small cell lung cancer, and are summarized in Table 3.

nucleotide mutations are abbreviated by the following shorthand. For example, a T311M amino acid mutation refers to a change at position 311 of the amino acid sequence of SEQ ID NO:2 (FIG. 2B) from wild-type T or threonine amino acid to a mutant M or methionine amino acid. Similarly, a C932T nucleotide mutation refers to a change at position 932 of the nucleotide sequence of SEQ ID NO:2 (FIG. 2B) from wild-type C nucleotide to a mutant T nucleotide.

Most of the mutations identified were localized in the ligand binding domain of ESR1, with the exception of Residue 311 of SED ID NO:2 (FIG. 2B), which was located near the C-terminal end of the hinge region of ESR1 (as depicted in FIG. 1). Other mutations identified included mutations at positions 341, 350, 394, 414, 433, 503, 537 and 538 of SEQ ID NO:2 (FIG. 2B), and an insertion between amino acids 344 and 345 of SEQ ID NO:2 (FIG. 2B).

Notably, several recurrent mutations at amino acid positions 537 and 538 of the ligand binding domain of ESR1 were identified in the breast cancer samples. More specifically, three mutations of the tyrosine residue at position 537 were identified in the breast cancer samples, for example, Y537N and Y537C. As shown in Table 3, all three mutations are associated with metastatic, ER+ (positive) breast cancer. In two of the three samples, the patients received tamoxifen. The drug treatment in one of the patients is unknown. At least two breast samples had a recurrent mutation at position 538 from D to G (see Table 3). Based on the information available, at least two of the samples were metastatic, ER+. In one of the samples, the patient received tamoxifen and in another sample, the previous treatment is unknown. Each of these mutations is described in more detail below.

TABLE 3

Mutations identified in ESR1 ligand-binding domain.

| Study | Tumor Type | Amino Acid Mutation[a] | Nucleotide Mutation[b] | Cancer Characteristics[c] | Other mutations identified in sample[c] |
|---|---|---|---|---|---|
| A | Colorectal | T311M | C932T | | |
| ? | ? | S341L | C1022T | | |
| ? | ? | A350E | C1049A | | |
| A | Colorectal | R394H | G1181A | | |
| B | Breast | Q414* | C1240T | | |
| C | NSCLC | S433P | T1297C | | |
| D | Breast | R503W | C1507T | Primary breast cancer, ER− | Her2 amp, P53 |
| D | Breast | Y537N | T1609A | Metastatic, ER+, patient received tamoxifen | P53, BRCA, NF1, EGFR/MYC gains |
| E | Breast | Y537C | A1610G | Metastatic, ER+, treatment unknown | PIK3CA, CCND1 |
| D | Breast | Y537C | A1610G | Metastatic, ER+, patient received tamoxifen | BRCA |
| E | Breast | D538G | A1613G | Metastatic, ER+, treatment unknown | CDH1, matching primary tumor sample was ESR1 WT |
| D | Breast | D538G | A1613G | Metastatic, ER+, patient received tamoxifen | BRCA |
| | Breast | C insertion between G344_L345 | GCT insertion between 1033_1034 | Metastatic, ER+ | |

[a] amino acid mutations refer to amino acid positions as defined by SEQ ID NO: 2 (FIG. 2B).
[b] nucleotide mutations refer to nucleotide position as defined by SEQ ID NO: 1 (FIG. 2B).
[c] ER− = estrogen receptor negative; ER+ = estrogen receptor positive, as determined by immunohistochemistry (IHC)); "amp" = amplification In particular, Table 3 summarizes the following: the tumor type, the amino acid and nucleotide positions of the mutations, the cancer characteristics, and other mutations identified in the sample. The position of the amino acid and the 3/12 (25% of metastatic, ER+ (estrogen receptor positive), tamoxifen-treated breast cancers in study D showed mutations at amino acids 537 and 538. Notably, 0/4 metastatic ER−, non-hormone-therapy treated breast cancers in study D showed these mutations; 0/33 primary breast cancers (mixed ER/PR/HER2) in study D showed mutations; and 0/81 primary triple negative breast cancers in study H showed mutations.

2/29 (7%) of metastatic, ER$^+$, treatment unknown breast cancers in study E showed mutations at amino acids 537 or 538. Notably again, 0/5 metastatic, ER$^-$ cases in study E had mutations at amino acids 537 or 538. One ESR1 mutation was observed in a metastatic sample of a primary tumor/metastatic pair where the primary sample was ESR1 wild-type.

At least one D538G mutation occurred after treatment with tamoxifen. In another case, the D538G mutation was found in the metastatic tumor, while the primary tumor showed wild-type ESR1. In particular, sequencing of DNA from the primary tumor sample indicated that the ESR1 gene did not carry the D538G mutation (see Study E result in Table 3 above). Thus, the presence of the D538G mutation can be associated with a response to SERM therapy, and/or be associated with a metastatic transition.

Further analysis of patient tumor (e.g., breast) tumor samples for the presence of the ESR1 mutations disclosed herein is summarized in Table 4. Generally, tumor samples carrying the ESR1 mutations disclosed herein, e.g., ESR1 mutations at amino acids 537 and/or 538, correlated with a late stage (e.g., metastatic) tumor. For example, out of 25 patients with ER+ status, having metastatic cancer, 20% of patients had somatic mutations in ESR1 (e.g., ESR1 mutations at amino acids 537 and/or 538), as shown in Table 4.

ESR1 somatic mutations are rare in breast cancer. The mutations at amino acid 537 and 538 were observed primarily in ER+ samples. Tyrosine 537 and Aspartate 538 are located at the C-terminal portion of the hormone binding domain of ER, which are regions associated with dimerization and AF-2 function. Tyrosine 537 is a target of c-Src phosphorylation, and mutations at position 537, in particular, the Y537N substitution, have been associated with constitutive ER activity, as measured by activation of target gene expression in vitro (Barone et al. (2010) *Clin Cancer Res.* 16(10):2702-8; Zhang et al. (1997) *Cancer Res.* 57:1244-1249).

Activity of the 537 mutant ER was minimally affected by estradiol or tamoxifen, suggesting that phosphorylation of the tyrosine residue at position 537 may regulate ER-α transactivation. Leucine at position 539 of SEQ ID NO:2 is one of the direct amino acid contacts with estrogen ligands, and mutations of L539 impair ER signaling (Shiau et al. (1998) *Cell* 95(7):927-937). Given the location, the mutation at position 538 (e.g., the D538G mutation) can impair one or more of: the phosphorylation of tyrosine 537, e.g., by disrupting a kinase motif, or may impact the binding of a co-activator or a ligand to the ER.

These results described herein suggest that subjects who are ER$^+$ can benefit from further testing to determine the presence or absence of a mutation in the ER ligand binding domain, e.g., mutations at amino acid 537 and/or 538. The presence of these mutations may indicate the presence of constitutive activated ER receptor and/or the presence of a hormone-resistant cancer. Alternative therapies can be administered to such subjects, including an aromatase inhibitor (e.g., anastrozole), a Selective Estrogen Receptor Downregulator (SERD) or an anti-estrogen (e.g., fulvestrant), or an mTOR (mammalian Target of Rapamycin) pathway inhibitor, or a combination thereof. Exemplary mTOR inhibitors include, for example, RAD001 (everolimus), CCI-799 (tensirolimus), and AP23573 (ARIAD).

In other embodiments, the subjects can have mutations in genes other than the ER receptor that can be treated with therapeutic agents specific to the mutations. Examples of such mutations can be found in Table 3, and include a HER2 mutation (e.g., HER2 amplification), a p53 mutation, BRCA, NF1, EGFR/myc gains, PIK3CA, CCND1 and CDH1. Thus, the subjects can receive a therapy that target the ESR1 mutation, alone or in combination with a therapy that targets another mutation identified as part of the cancer, e.g., a drug that targets mutant HER2 mutation (e.g., HER2 amplification), a p53 mutation, BRCA, NF1, EGFR/myc gains, PIK3CA, CCND1 and/or CDH1.

TABLE 4

Further analysis of ESR1 alterations

| # patients | ER status | Specimens sequenced | # of patients with known somatic mutations in ESR1 or amp | % of patients with known somatic mutations in ESR1 or amp | ESR1 alteration |
|---|---|---|---|---|---|
| 17 | + | Primary | 1 | 6% | ESR1 alteration is AMP, estimated CN = 10 |
| 25 | + | Metastasis | 5 | 20% | all ESR1 mutations aa537/538 |
| 16 | − | Primary | 0 | 0% | |
| 5 | − | Metastasis | 0 | 0% | |
| 1 | uncertain | Metastasis | 0 | 0% | |
| 33 | + | Primary/Met. matched set | 2 | 6% | ESR1 aa537 and 538 present in metastases, absent in primary |
| 1 | + | Primary | 0 | 0% | |
| 6 | − | Primary/Met. matched set | 0 | 0% | |

TABLE 4-continued

Further analysis of ESR1 alterations

| # patients | ER status | Specimens sequenced | # of patients with known somatic mutations in ESR1 or amp | % of patients with known somatic mutations in ESR1 or amp | ESR1 alteration |
|---|---|---|---|---|---|
| 3 | − | Primary | 0 | 0% | |
| 16 | + | Primary/Met. matched set | 1 | 6% | ESR1 amp present in all 3 metastatic samples in set, ESR1 Y537N present in 2/3, no matching primary sequenced |
| 3 | + | Primary | 0 | 0% | |
| 118 | unknown in general | mixed | 6 | 5% | 5 ESR1 D538G, 1 AMP; 3/5 with D538G known as mets of ER+ Breast Ca.; matching primary sequenced for 2/5 and confirmed negative |
| 81 | − | Primary (TNBC) | 0 | 0% | |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by the COSMIC database, available on the worldwide web at sanger.ac.uk/genetics/CGP/cosmia; and the Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having a breast cancer, comprising:
   detecting in a sample from the subject:
   (a) a mutant estrogen receptor 1 (ESR1) polypeptide or a nucleic acid molecule encoding the mutant ESR1 polypeptide, and
   (b) an Estrogen Receptor positive (ER+) breast cancer;
   wherein the mutant ESR1 polypeptide, or the nucleic acid molecule encoding the mutant ESR1 polypeptide, comprises one or more of:
   one or more missense mutations at amino acid position 311, 341, 350, 394, 414, 433, 503, or 538 of SEQ ID NO: 2,
   a deletion of nucleotides 1046-1051 of SEQ ID NO: 1, or
   an insertion between amino acid positions 344 and 345 of SEQ ID NO: 2; and
   administering to the subject an effective amount of an anti-cancer agent other than a Selective Estrogen Receptor Modulator (SERM), wherein the anti-cancer agent is a Selective Estrogen Receptor Degrader (SERD),
   thereby treating the breast cancer in the subject.

2. The method of claim 1, wherein the mutant ESR1 polypeptide comprises one or more of:
   an aspartate to glycine substitution at amino acid position 538 (D538G) of SEQ ID NO: 2;
   a deletion of amino acids Leu-Ala-Asp (LAD) at positions 349-351 of SEQ ID NO:2;
   an insertion of a histidine at amino acid position 349 of SEQ ID NO:2;
   a threonine to methionine substitution at amino acid position 311 (T311M) of SEQ ID NO: 2;
   a serine to leucine substitution at amino acid position 341 (S341L) of SEQ ID NO: 2;
   an alanine to glutamate substitution at amino acid position 350 (A350E) of SEQ ID NO: 2;
   an arginine to histidine substitution at amino acid position 394 (R394H) of SEQ ID NO: 2;
   a glutamine substitution at amino acid position 414 of SEQ ID NO: 2;
   a serine to proline substitution at amino acid position 433 (S433P) of SEQ ID NO: 2;
   an arginine to tryptophan substitution at amino acid position 503 (R503W) of SEQ ID NO: 2; or
   an insertion of a cysteine between amino acid positions 344 and 345 of SEQ ID NO:2.

3. The method of claim 1, wherein said subject:
   (i) has previously received a treatment with a SERM;
   (ii) has failed a first or second line of treatment with a SERM;
   (iii) has a late stage, metastatic progressive breast cancer;
   (iv) is postmenopausal or premenopausal;
   (v) stops a treatment with a SERM prior to administration of the anti-cancer agent other than a SERM;
   (vi) is premenopausal and an oophorectomy is performed on the subject;
   or any combination of (i)-(vi).

4. The method of claim 1, wherein the SERM is raloxifene, EM652, GW7604, keoxifene, toremifene, tamoxifen, lasofoxifene, levormeloxifene, bazedoxifene, or arzoxifene.

5. The method of claim 1, wherein the subject is postmenopausal.

6. The method of claim 1, wherein the anti-cancer agent is fulvestrant.

7. The method of claim 1, wherein the anti-cancer agent is administered in combination with a different therapeutic agent or a different therapeutic modality.

8. The method of claim 7, wherein the different therapeutic agent or modality is selected according to a determination of the presence of a mutation other than the mutant ESR1 polypeptide or the nucleic acid molecule encoding the mutant ESR1 polypeptide, and wherein the mutation other than the mutant ESR1 polypeptide or the nucleic acid molecule encoding the mutant ESR1 polypeptide is a HER2 mutation, a p53 mutation, a BRCA mutation, an NF1 mutation, an EGFR/myc mutation, a PIK3CA mutation, a CCND1 mutation, a CDH1 mutation, or any combination thereof.

9. The method of claim 1, wherein the detecting step comprises determining the presence of the mutant ESR1 polypeptide or the nucleic acid molecule encoding the mutant ESR1 polypeptide by sequencing.

10. The method of claim 1, wherein the subject was previously tested for the presence of a mutant ESR1 polypeptide or a nucleic acid molecule encoding the mutant ESR1 polypeptide, wherein the mutant ESR1 polypeptide or the nucleic acid molecule encoding the mutant ESR1 polypeptide was not detected during the previous testing,
   and wherein the subject was administered a SERM based on the knowledge that the mutant ESR1 polypeptide or the nucleic acid molecule encoding the mutant ESR1 polypeptide was not detected during the previous testing.

11. The method of claim 1, wherein the subject was previously tested at intervals for the presence of a mutant ESR1 polypeptide or a nucleic acid molecule encoding the mutant ESR1 polypeptide, wherein the mutant ESR1 polypeptide or the nucleic acid molecule encoding the mutant ESR1 polypeptide was not detected during the previous testing, and wherein the subject continued a treatment with a SERM based on the knowledge that the mutant ESR1 polypeptide or the nucleic acid molecule encoding the mutant ESR1 polypeptide was not detected during the previous testing.

12. The method of claim 1, wherein the subject was previously tested or is being tested for the presence of a mutant ESR1 polypeptide or a nucleic acid molecule encoding the mutant ESR1 polypeptide at 6 month or one-year intervals.

13. The method of claim 1, wherein the subject was previously tested at intervals for the presence of a mutant ESR1 polypeptide or a nucleic acid molecule encoding the mutant ESR1 polypeptide, wherein the mutant ESR1 polypeptide or the nucleic acid molecule encoding the mutant ESR1 polypeptide was detected during the previous testing, and wherein the subject stopped a treatment with a SERM based on the knowledge that the mutant ESR1 polypeptide or the nucleic acid molecule encoding the mutant ESR1 polypeptide was detected during the previous testing.

14. The method of claim 1, further comprising generating a personalized cancer treatment report, by:
    obtaining the sample from the subject,
    detecting the mutant ESR1 polypeptide or the nucleic acid molecule encoding the mutant ESR1 polypeptide in the sample, and
    selecting a treatment based on the ESR1 mutation detected.

15. The method of claim 1, further comprising:
(i) identifying, selecting, or obtaining information or knowledge that the subject has participated in a clinical trial or has been treated for cancer; and
(ii) acquiring genotype information that identifies a mutant ESR1 polypeptide or a nucleic acid molecule encoding the mutant ESR1 polypeptide as being in the subject,
wherein the presence of the mutant ESR1 polypeptide or the nucleic acid molecule encoding the mutant ESR1 polypeptide identifies the subject as having an increased risk for, or having, a cancer associated with the mutant ESR1 polypeptide or the nucleic acid molecule encoding the mutant ESR1 polypeptide.

* * * * *

SEQUENCE LISTING

```
<160> NUMBER OF SEQ ID NOS: 11

<210> SEQ ID NO 1
<211> LENGTH: 1788
<212> TYPE: DNA
<213> ORGANISM: Homo sapiens
<220> FEATURE:
<221> NAME/KEY: CDS
<222> LOCATION: (1)..(1785)

<400> SEQUENCE: 1 atg acc atg acc ctc cac acc aaa gca tct ggg atg gcc cta ctg cat      48
Met Thr Met Thr Leu His Thr Lys Ala Ser Gly Met Ala Leu Leu His
1               5                   10                  15 cag atc caa ggg aac gag ctg gag ccc ctg aac cgt ccg cag ctc aag      96
Gln Ile Gln Gly Asn Glu Leu Glu Pro Leu Asn Arg Pro Gln Leu Lys
            20                  25                  30 atc ccc ctg gag cgg ccc ctg ggc gag gtg tac ctg gac agc agc aag     144
Ile Pro Leu Glu Arg Pro Leu Gly Glu Val Tyr Leu Asp Ser Ser Lys
        35                  40                  45 ccc gcc gtg tac aac tac ccc gag ggc gcc gcc tac gag ttc aac gcc     192
Pro Ala Val Tyr Asn Tyr Pro Glu Gly Ala Ala Tyr Glu Phe Asn Ala
    50                  55                  60
```

|  |  |
|---|---|
| gcg gcc gcc gcc aac gcg cag gtc tac ggt cag acc ggc ctc ccc tac<br>Ala Ala Ala Ala Asn Ala Gln Val Tyr Gly Gln Thr Gly Leu Pro Tyr<br>65                         70                   75                80 | 240 |
| ggc ccc ggg tct gag gct gcg gcg ttc ggc tcc aac ggc ctg ggg ggt<br>Gly Pro Gly Ser Glu Ala Ala Ala Phe Gly Ser Asn Gly Leu Gly Gly<br>                 85                   90                 95 | 288 |
| ttc ccc cca ctc aac agc gtg tct ccg agc ccg ctg atg cta ctg cac<br>Phe Pro Pro Leu Asn Ser Val Ser Pro Ser Pro Leu Met Leu Leu His<br>             100                 105              110 | 336 |
| ccg ccg ccg cag ctg tcg cct ttc ctg cag ccc cac ggc cag cag gtg<br>Pro Pro Pro Gln Leu Ser Pro Phe Leu Gln Pro His Gly Gln Gln Val<br>             115                 120              125 | 384 |
| ccc tac tac ctg gag aac gag ccc agc ggc tac acg gtg cgc gag gcc<br>Pro Tyr Tyr Leu Glu Asn Glu Pro Ser Gly Tyr Thr Val Arg Glu Ala<br>            130                 135              140 | 432 |
| ggc ccg ccg gca ttc tac agg cca aat tca gat aat cga cgc cag ggt<br>Gly Pro Pro Ala Phe Tyr Arg Pro Asn Ser Asp Asn Arg Arg Gln Gly<br>145                   150                 155              160 | 480 |
| ggc aga gaa aga ttg gcc agt acc aat gac aag gga agt atg gct atg<br>Gly Arg Glu Arg Leu Ala Ser Thr Asn Asp Lys Gly Ser Met Ala Met<br>                 165                 170              175 | 528 |
| gaa tct gcc aag gag act cgc tac tgt gca gtg tgc aat gac tat gct<br>Glu Ser Ala Lys Glu Thr Arg Tyr Cys Ala Val Cys Asn Asp Tyr Ala<br>            180                 185              190 | 576 |
| tca ggc tac cat tat gga gtc tgg tcc tgt gag ggc tgc aag gcc ttc<br>Ser Gly Tyr His Tyr Gly Val Trp Ser Cys Glu Gly Cys Lys Ala Phe<br>             195                 200              205 | 624 |
| ttc aag aga agt att caa gga cat aac gac tat atg tgt cca gcc acc<br>Phe Lys Arg Ser Ile Gln Gly His Asn Asp Tyr Met Cys Pro Ala Thr<br>210                   215                 220 | 672 |
| aac cag tgc acc att gat aaa aac agg agg aag agc tgc cag gcc tgc<br>Asn Gln Cys Thr Ile Asp Lys Asn Arg Arg Lys Ser Cys Gln Ala Cys<br>225                   230                 235              240 | 720 |
| cgg ctc cgc aaa tgc tac gaa gtg gga atg atg aaa ggt ggg ata cga<br>Arg Leu Arg Lys Cys Tyr Glu Val Gly Met Met Lys Gly Gly Ile Arg<br>            245                 250              255 | 768 |
| aaa gac cga aga gga ggg aga atg ttg aaa cac aag cgc cag aga gat<br>Lys Asp Arg Arg Gly Gly Arg Met Leu Lys His Lys Arg Gln Arg Asp<br>            260                 265              270 | 816 |
| gat ggg gag ggc agg ggt gaa gtg ggg tct gct gga gac atg aga gct<br>Asp Gly Glu Gly Arg Gly Glu Val Gly Ser Ala Gly Asp Met Arg Ala<br>            275                 280              285 | 864 |
| gcc aac ctt tgg cca agc ccg ctc atg atc aaa cgc tct aag aag aac<br>Ala Asn Leu Trp Pro Ser Pro Leu Met Ile Lys Arg Ser Lys Lys Asn<br>290                   295                 300 | 912 |
| agc ctg gcc ttg tcc ctg acg gcc gac cag atg gtc agt gcc ttg ttg<br>Ser Leu Ala Leu Ser Leu Thr Ala Asp Gln Met Val Ser Ala Leu Leu<br>305                   310                 315              320 | 960 |
| gat gct gag ccc ccc ata ctc tat tcc gag tat gat cct acc aga ccc<br>Asp Ala Glu Pro Pro Ile Leu Tyr Ser Glu Tyr Asp Pro Thr Arg Pro<br>            325                 330              335 | 1008 |
| ttc agt gaa gct tcg atg atg ggc tta ctg acc aac ctg gca gac agg<br>Phe Ser Glu Ala Ser Met Met Gly Leu Leu Thr Asn Leu Ala Asp Arg<br>            340                 345              350 | 1056 |
| gag ctg gtt cac atg atc aac tgg gcg aag agg gtg cca ggc ttt gtg<br>Glu Leu Val His Met Ile Asn Trp Ala Lys Arg Val Pro Gly Phe Val<br>            355                 360              365 | 1104 |
| gat ttg acc ctc cat gat cag gtc cac ctt cta gaa tgt gcc tgg cta<br>Asp Leu Thr Leu His Asp Gln Val His Leu Leu Glu Cys Ala Trp Leu<br>370                   375                 380 | 1152 |

```
gag atc ctg atg att ggt ctc gtc tgg cgc tcc atg gag cac cca gtg      1200
Glu Ile Leu Met Ile Gly Leu Val Trp Arg Ser Met Glu His Pro Val
385                 390                 395                 400 aag cta ctg ttt gct cct aac ttg ctc ttg gac agg aac cag gga aaa      1248
Lys Leu Leu Phe Ala Pro Asn Leu Leu Leu Asp Arg Asn Gln Gly Lys
            405                 410                 415 tgt gta gag ggc atg gtg gag atc ttc gac atg ctg ctg gct aca tca      1296
Cys Val Glu Gly Met Val Glu Ile Phe Asp Met Leu Leu Ala Thr Ser
        420                 425                 430 tct cgg ttc cgc atg atg aat ctg cag gga gag gag ttt gtg tgc ctc      1344
Ser Arg Phe Arg Met Met Asn Leu Gln Gly Glu Glu Phe Val Cys Leu
    435                 440                 445 aaa tct att att ttg ctt aat tct gga gtg tac aca ttt ctg tcc agc      1392
Lys Ser Ile Ile Leu Leu Asn Ser Gly Val Tyr Thr Phe Leu Ser Ser
450                 455                 460 acc ctg aag tct ctg gaa gag aag gac cat atc cac cga gtc ctg gac      1440
Thr Leu Lys Ser Leu Glu Glu Lys Asp His Ile His Arg Val Leu Asp
465                 470                 475                 480 aag atc aca gac act ttg atc cac ctg atg gcc aag gca ggc ctg acc      1488
Lys Ile Thr Asp Thr Leu Ile His Leu Met Ala Lys Ala Gly Leu Thr
            485                 490                 495 ctg cag cag cag cac cag cgg ctg gcc cag ctc ctc ctc atc ctc tcc      1536
Leu Gln Gln Gln His Gln Arg Leu Ala Gln Leu Leu Leu Ile Leu Ser
        500                 505                 510 cac atc agg cac atg agt aac aaa ggc atg gag cat ctg tac agc atg      1584
His Ile Arg His Met Ser Asn Lys Gly Met Glu His Leu Tyr Ser Met
    515                 520                 525 aag tgc aag aac gtg gtg ccc ctc tat gac ctg ctg gag atg ctg           1632
Lys Cys Lys Asn Val Val Pro Leu Tyr Asp Leu Leu Glu Met Leu
530                 535                 540 gac gcc cac cgc cta cat gcg ccc act agc cgt gga ggg gca tcc gtg      1680
Asp Ala His Arg Leu His Ala Pro Thr Ser Arg Gly Gly Ala Ser Val
545                 550                 555                 560 gag gag acg gac caa agc cac ttg gcc act gcg ggc tct act tca tcg      1728
Glu Glu Thr Asp Gln Ser His Leu Ala Thr Ala Gly Ser Thr Ser Ser
            565                 570                 575 cat tcc ttg caa aag tat tac atc acg ggg gag gca gag ggt ttc cct      1776
His Ser Leu Gln Lys Tyr Tyr Ile Thr Gly Glu Ala Glu Gly Phe Pro
        580                 585                 590 gcc aca gtc tga                                                       1788
Ala Thr Val
    595

<210> SEQ ID NO 2
<211> LENGTH: 595
<212> TYPE: PRT
<213> ORGANISM: Homo sapiens

<400> SEQUENCE: 2

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80
```

```
Gly Pro Gly Ser Glu Ala Ala Phe Gly Ser Asn Gly Leu Gly Gly
                85                  90                  95

Phe Pro Pro Leu Asn Ser Val Ser Pro Ser Pro Leu Met Leu Leu His
                100                 105                 110

Pro Pro Pro Gln Leu Ser Pro Phe Leu Gln Pro His Gly Gln Gln Val
                115                 120                 125

Pro Tyr Tyr Leu Glu Asn Glu Pro Ser Gly Tyr Thr Val Arg Glu Ala
        130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
                180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
        210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
                260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
                340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
        370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
                420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
        450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495
```

```
Leu Gln Gln Gln His Gln Arg Leu Ala Gln Leu Leu Leu Ile Leu Ser
                500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
        580                 585                 590

Ala Thr Val
        595

<210> SEQ ID NO 3
<211> LENGTH: 1782
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1779)

<400> SEQUENCE: 3 atg acc atg acc ctc cac acc aaa gca tct ggg atg gcc cta ctg cat     48
Met Thr Met Thr Leu His Thr Lys Ala Ser Gly Met Ala Leu Leu His
1               5                  10                  15 cag atc caa ggg aac gag ctg gag ccc ctg aac cgt ccg cag ctc aag     96
Gln Ile Gln Gly Asn Glu Leu Glu Pro Leu Asn Arg Pro Gln Leu Lys
            20                  25                  30 atc ccc ctg gag cgg ccc ctg ggc gag gtg tac ctg gac agc agc aag    144
Ile Pro Leu Glu Arg Pro Leu Gly Glu Val Tyr Leu Asp Ser Ser Lys
        35                  40                  45 ccc gcc gtg tac aac tac ccc gag ggc gcc gcc tac gag ttc aac gcc    192
Pro Ala Val Tyr Asn Tyr Pro Glu Gly Ala Ala Tyr Glu Phe Asn Ala
    50                  55                  60 gcg gcc gcc gcc aac gcg cag gtc tac ggt cag acc ggc ctc ccc tac    240
Ala Ala Ala Ala Asn Ala Gln Val Tyr Gly Gln Thr Gly Leu Pro Tyr
65                  70                  75                  80 ggc ccc ggg tct gag gct gcg gcg ttc ggc tcc aac ggc ctg ggg ggt    288
Gly Pro Gly Ser Glu Ala Ala Ala Phe Gly Ser Asn Gly Leu Gly Gly
                85                  90                  95 ttc ccc cca ctc aac agc gtg tct ccg agc ccg ctg atg cta ctg cac    336
Phe Pro Pro Leu Asn Ser Val Ser Pro Ser Pro Leu Met Leu Leu His
            100                 105                 110 ccg ccg ccg cag ctg tcg cct ttc ctg cag ccc cac ggc cag cag gtg    384
Pro Pro Pro Gln Leu Ser Pro Phe Leu Gln Pro His Gly Gln Gln Val
        115                 120                 125 ccc tac tac ctg gag aac gag ccc agc ggc tac acg gtg cgc gag gcc    432
Pro Tyr Tyr Leu Glu Asn Glu Pro Ser Gly Tyr Thr Val Arg Glu Ala
    130                 135                 140 ggc ccg ccg gca ttc tac agg cca aat tca gat aat cga cgc cag ggt    480
Gly Pro Pro Ala Phe Tyr Arg Pro Asn Ser Asp Asn Arg Arg Gln Gly
145                 150                 155                 160 ggc aga gaa aga ttg gcc agt acc aat gac aag gga agt atg gct atg    528
Gly Arg Glu Arg Leu Ala Ser Thr Asn Asp Lys Gly Ser Met Ala Met
                165                 170                 175
```

```
                                                          -continued gaa tct gcc aag gag act cgc tac tgt gca gtg tgc aat gac tat gct    576
Glu Ser Ala Lys Glu Thr Arg Tyr Cys Ala Val Cys Asn Asp Tyr Ala
            180                 185                 190 tca ggc tac cat tat gga gtc tgg tcc tgt gag ggc tgc aag gcc ttc    624
Ser Gly Tyr His Tyr Gly Val Trp Ser Cys Glu Gly Cys Lys Ala Phe
        195                 200                 205 ttc aag aga agt att caa gga cat aac gac tat atg tgt cca gcc acc    672
Phe Lys Arg Ser Ile Gln Gly His Asn Asp Tyr Met Cys Pro Ala Thr
    210                 215                 220 aac cag tgc acc att gat aaa aac agg agg aag agc tgc cag gcc tgc    720
Asn Gln Cys Thr Ile Asp Lys Asn Arg Arg Lys Ser Cys Gln Ala Cys
225                 230                 235                 240 cgg ctc cgc aaa tgc tac gaa gtg gga atg atg aaa ggt ggg ata cga    768
Arg Leu Arg Lys Cys Tyr Glu Val Gly Met Met Lys Gly Gly Ile Arg
                245                 250                 255 aaa gac cga aga gga ggg aga atg ttg aaa cac aag cgc cag aga gat    816
Lys Asp Arg Arg Gly Gly Arg Met Leu Lys His Lys Arg Gln Arg Asp
            260                 265                 270 gat ggg gag ggc agg ggt gaa gtg ggg tct gct gga gac atg aga gct    864
Asp Gly Glu Gly Arg Gly Glu Val Gly Ser Ala Gly Asp Met Arg Ala
        275                 280                 285 gcc aac ctt tgg cca agc ccg ctc atg atc aaa cgc tct aag aag aac    912
Ala Asn Leu Trp Pro Ser Pro Leu Met Ile Lys Arg Ser Lys Lys Asn
    290                 295                 300 agc ctg gcc ttg tcc ctg acg gcc gac cag atg gtc agt gcc ttg ttg    960
Ser Leu Ala Leu Ser Leu Thr Ala Asp Gln Met Val Ser Ala Leu Leu
305                 310                 315                 320 gat gct gag ccc ccc ata ctc tat tcc gag tat gat cct acc aga ccc   1008
Asp Ala Glu Pro Pro Ile Leu Tyr Ser Glu Tyr Asp Pro Thr Arg Pro
                325                 330                 335 ttc agt gaa gct tcg atg atg ggc tta ctg acc aac cac agg gag ctg   1056
Phe Ser Glu Ala Ser Met Met Gly Leu Leu Thr Asn His Arg Glu Leu
            340                 345                 350 gtt cac atg atc aac tgg gcg aag agg gtg cca ggc ttt gtg gat ttg   1104
Val His Met Ile Asn Trp Ala Lys Arg Val Pro Gly Phe Val Asp Leu
        355                 360                 365 acc ctc cat gat cag gtc cac ctt cta gaa tgt gcc tgg cta gag atc   1152
Thr Leu His Asp Gln Val His Leu Leu Glu Cys Ala Trp Leu Glu Ile
    370                 375                 380 ctg atg att ggt ctc gtc tgg cgc tcc atg gag cac cca gtg aag cta   1200
Leu Met Ile Gly Leu Val Trp Arg Ser Met Glu His Pro Val Lys Leu
385                 390                 395                 400 ctg ttt gct cct aac ttg ctc ttg gac agg aac cag gga aaa tgt gta   1248
Leu Phe Ala Pro Asn Leu Leu Leu Asp Arg Asn Gln Gly Lys Cys Val
                405                 410                 415 gag ggc atg gtg gag atc ttc gac atg ctg ctg gct aca tca tct cgg   1296
Glu Gly Met Val Glu Ile Phe Asp Met Leu Leu Ala Thr Ser Ser Arg
            420                 425                 430 ttc cgc atg atg aat ctg cag gga gag gag ttt gtg tgc ctc aaa tct   1344
Phe Arg Met Met Asn Leu Gln Gly Glu Glu Phe Val Cys Leu Lys Ser
        435                 440                 445 att att ttg ctt aat tct gga gtg tac aca ttt ctg tcc agc acc ctg   1392
Ile Ile Leu Leu Asn Ser Gly Val Tyr Thr Phe Leu Ser Ser Thr Leu
    450                 455                 460 aag tct ctg gaa gag aag gac cat atc cac cga gtc ctg gac aag atc   1440
Lys Ser Leu Glu Glu Lys Asp His Ile His Arg Val Leu Asp Lys Ile
465                 470                 475                 480 aca gac act ttg atc cac ctg atg gcc aag gca ggc ctg acc ctg cag   1488
Thr Asp Thr Leu Ile His Leu Met Ala Lys Ala Gly Leu Thr Leu Gln
                485                 490                 495
```

```
cag cag cac cag cgg ctg gcc cag ctc ctc ctc atc ctc tcc cac atc      1536
Gln Gln His Gln Arg Leu Ala Gln Leu Leu Leu Ile Leu Ser His Ile
            500                 505                 510 agg cac atg agt aac aaa ggc atg gag cat ctg tac agc atg aag tgc      1584
Arg His Met Ser Asn Lys Gly Met Glu His Leu Tyr Ser Met Lys Cys
        515                 520                 525 aag aac gtg gtg ccc ctc tat gac ctg ctg ctg gag atg ctg gac gcc      1632
Lys Asn Val Val Pro Leu Tyr Asp Leu Leu Leu Glu Met Leu Asp Ala
530                 535                 540 cac cgc cta cat gcg ccc act agc cgt gga ggg gca tcc gtg gag gag      1680
His Arg Leu His Ala Pro Thr Ser Arg Gly Gly Ala Ser Val Glu Glu
545                 550                 555                 560 acg gac caa agc cac ttg gcc act gcg ggc tct act tca tcg cat tcc      1728
Thr Asp Gln Ser His Leu Ala Thr Ala Gly Ser Thr Ser Ser His Ser
            565                 570                 575 ttg caa aag tat tac atc acg ggg gag gca gag ggt ttc cct gcc aca      1776
Leu Gln Lys Tyr Tyr Ile Thr Gly Glu Ala Glu Gly Phe Pro Ala Thr
        580                 585                 590 gtc tga                                                              1782
Val

<210> SEQ ID NO 4
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
```

```
                210                 215                 220
        Asn Gln Cys Thr Ile Asp Lys Asn Arg Arg Lys Ser Cys Gln Ala Cys
        225                 230                 235                 240

Arg Leu Arg Lys Cys Tyr Glu Val Gly Met Met Lys Gly Gly Ile Arg
                            245                 250                 255

Lys Asp Arg Arg Gly Gly Arg Met Leu Lys His Lys Arg Gln Arg Asp
                        260                 265                 270

Asp Gly Glu Gly Arg Gly Glu Val Gly Ser Ala Gly Asp Met Arg Ala
                    275                 280                 285

Ala Asn Leu Trp Pro Ser Pro Leu Met Ile Lys Arg Ser Lys Lys Asn
        290                 295                 300

Ser Leu Ala Leu Ser Leu Thr Ala Asp Gln Met Val Ser Ala Leu Leu
        305                 310                 315                 320

Asp Ala Glu Pro Pro Ile Leu Tyr Ser Glu Tyr Asp Pro Thr Arg Pro
                            325                 330                 335

Phe Ser Glu Ala Ser Met Met Gly Leu Leu Thr Asn His Arg Glu Leu
                        340                 345                 350

Val His Met Ile Asn Trp Ala Lys Arg Val Pro Gly Phe Val Asp Leu
                    355                 360                 365

Thr Leu His Asp Gln Val His Leu Leu Glu Cys Ala Trp Leu Glu Ile
        370                 375                 380

Leu Met Ile Gly Leu Val Trp Arg Ser Met Glu His Pro Val Lys Leu
        385                 390                 395                 400

Leu Phe Ala Pro Asn Leu Leu Leu Asp Arg Asn Gln Gly Lys Cys Val
                            405                 410                 415

Glu Gly Met Val Glu Ile Phe Asp Met Leu Leu Ala Thr Ser Ser Arg
                        420                 425                 430

Phe Arg Met Met Asn Leu Gln Gly Glu Glu Phe Val Cys Leu Lys Ser
                    435                 440                 445

Ile Ile Leu Leu Asn Ser Gly Val Tyr Thr Phe Leu Ser Ser Thr Leu
        450                 455                 460

Lys Ser Leu Glu Glu Lys Asp His Ile His Arg Val Leu Asp Lys Ile
        465                 470                 475                 480

Thr Asp Thr Leu Ile His Leu Met Ala Lys Ala Gly Leu Thr Leu Gln
                            485                 490                 495

Gln Gln His Gln Arg Leu Ala Gln Leu Leu Leu Ile Leu Ser His Ile
                        500                 505                 510

Arg His Met Ser Asn Lys Gly Met Glu His Leu Tyr Ser Met Lys Cys
                    515                 520                 525

Lys Asn Val Val Pro Leu Tyr Asp Leu Leu Leu Glu Met Leu Asp Ala
        530                 535                 540

His Arg Leu His Ala Pro Thr Ser Arg Gly Gly Ala Ser Val Glu Glu
        545                 550                 555                 560

Thr Asp Gln Ser His Leu Ala Thr Ala Gly Ser Thr Ser Ser His Ser
                            565                 570                 575

Leu Gln Lys Tyr Tyr Ile Thr Gly Glu Ala Glu Gly Phe Pro Ala Thr
                        580                 585                 590

Val

<210> SEQ ID NO 5
        <211> LENGTH: 13
        <212> TYPE: DNA
        <213> ORGANISM: Artificial Sequence
        <220> FEATURE:
```

```
<223> OTHER INFORMATION: Description of Artificial Sequence: Synthetic
      consensus sequence
<220> FEATURE:
<221> NAME/KEY: modified_base
<222> LOCATION: (6)..(8)
<223> OTHER INFORMATION: a, c, t, g, unknown or other

<400> SEQUENCE: 5
ggtcannntg acc                                                          13

<210> SEQ ID NO 6
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(185)
<223> OTHER INFORMATION: a, c, t, g, unknown or other

<400> SEQUENCE: 6
atcgcaccag cgtgtnnnnn nnnnnnnnnn nnnnnnnnnn nnnnnnnnnn nnnnnnnnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnnnnnnnn nnnnnnnnnn nnnnnnnnnn       180
nnnnncactg cggctcctca                                                   200

<210> SEQ ID NO 7
<211> LENGTH: 17
<212> TYPE: DNA
<213> ORGANISM: Homo sapiens

<400> SEQUENCE: 7
aacattatat aacaacc                                                      17

<210> SEQ ID NO 8
<211> LENGTH: 11
<212> TYPE: DNA
<213> ORGANISM: Homo sapiens

<400> SEQUENCE: 8
aaagaaacaa a                                                            11

<210> SEQ ID NO 9
<211> LENGTH: 13
<212> TYPE: DNA
<213> ORGANISM: Homo sapiens

<400> SEQUENCE: 9
gtgaagcttc gat                                                          13

<210> SEQ ID NO 10
<211> LENGTH: 64
<212> TYPE: DNA
<213> ORGANISM: Homo sapiens
<220> FEATURE:
<221> NAME/KEY: CDS
<222> LOCATION: (1)..(63)

<400> SEQUENCE: 10 agt gaa gct tcg atg atg ggc tta ctg acc aac ctg gca gac agg gag         48
Ser Glu Ala Ser Met Met Gly Leu Leu Thr Asn Leu Ala Asp Arg Glu
1               5                   10                  15
```

```
ctg gtt cac atg atc a                                              64
Leu Val His Met Ile
        20

<210> SEQ ID NO 11
<211> LENGTH: 21
<212> TYPE: PRT
<213> ORGANISM: Homo sapiens

<400> SEQUENCE: 11

Ser Glu Ala Ser Met Met Gly Leu Leu Thr Asn Leu Ala Asp Arg Glu
1               5                   10                  15

Leu Val His Met Ile
        20
```